(12) United States Patent
Fawaz et al.

(10) Patent No.: US 12,378,194 B2
(45) Date of Patent: Aug. 5, 2025

(54) N, N-DIMETHYLTRYPTAMINE SALTS AND CRYSTALLINE SALT FORMS

(71) Applicant: ATAI Therapeutics, Inc., Encinitas, CA (US)

(72) Inventors: Majed Fawaz, Foxborough, MA (US); Nicholas Morra, Ontario (CA); Setu Kasera, Berlin (DE)

(73) Assignee: Atai Therapeutics, Inc., New York, NY (US)

( * ) Notice: Subject to any disclaimer, the term of this patent is extended or adjusted under 35 U.S.C. 154(b) by 0 days.

(21) Appl. No.: 17/824,861

(22) Filed: May 25, 2022

(65) Prior Publication Data

US 2022/0388956 A1    Dec. 8, 2022

Related U.S. Application Data

(60) Provisional application No. 63/192,938, filed on May 25, 2021.

(51) Int. Cl.
    *C07D 209/16* (2006.01)
(52) U.S. Cl.
    CPC ........ *C07D 209/16* (2013.01); *C07B 2200/13* (2013.01)
(58) Field of Classification Search
    CPC ............................ C07D 209/16; C07B 2200/13
    See application file for complete search history.

(56) References Cited

U.S. PATENT DOCUMENTS

| | | |
|---|---|---|
| 3,499,003 A | 3/1970 | Welstead, Jr. |
| 5,340,838 A | 8/1994 | Gidda et al. |
| 5,347,029 A | 9/1994 | Johnson |
| 5,637,593 A | 6/1997 | Porter et al. |
| 5,705,527 A | 1/1998 | Ishihara et al. |
| 6,201,025 B1 | 3/2001 | Dax et al. |
| 6,436,950 B1 | 8/2002 | Achari et al. |
| 6,500,456 B1 | 12/2002 | Capella |
| 8,268,856 B2 | 9/2012 | Hamann et al. |
| 9,388,395 B2 | 7/2016 | Nazor et al. |
| 10,550,140 B2 | 2/2020 | Wiles et al. |
| 11,242,318 B2 | 2/2022 | Nivorozhkin et al. |
| 11,332,441 B2 | 5/2022 | Chadeayne |
| 11,591,353 B2 | 2/2023 | Slassi et al. |
| 11,602,521 B2 | 3/2023 | Rao et al. |
| 11,643,391 B2 | 5/2023 | Perni et al. |
| 12,012,381 B2 | 6/2024 | Perni et al. |
| 12,065,405 B2 | 8/2024 | Perni |
| 12,128,027 B2 | 10/2024 | Rao et al. |
| 2002/0052370 A1 | 5/2002 | Barber et al. |
| 2002/0115715 A1 | 8/2002 | Dax et al. |
| 2003/0079301 A1 | 5/2003 | Sauter et al. |
| 2004/0235899 A1 | 11/2004 | Maria Assunta et al. |
| 2005/0152858 A1 | 7/2005 | Bertz et al. |
| 2005/0245594 A1 | 11/2005 | Sutter et al. |
| 2005/0250839 A1 | 11/2005 | Marnett et al. |
| 2007/0099909 A1 | 5/2007 | Chen et al. |
| 2008/0248511 A1 | 10/2008 | Daily et al. |
| 2008/0306025 A1 | 12/2008 | Yu et al. |
| 2008/0318957 A1 | 12/2008 | Glinka et al. |
| 2009/0221549 A1 | 9/2009 | Gerber et al. |
| 2010/0113539 A1 | 5/2010 | Scott et al. |
| 2012/0028995 A1 | 2/2012 | Ansorge et al. |
| 2015/0071994 A1 | 3/2015 | Schentag et al. |
| 2015/0346226 A1 | 12/2015 | McConnell et al. |
| 2016/0002195 A1 | 1/2016 | Makriyannis et al. |
| 2016/0074411 A1 | 3/2016 | Krumpl |
| 2016/0106694 A1 | 4/2016 | Roberts et al. |
| 2019/0315689 A1 | 10/2019 | Chen et al. |
| 2020/0325124 A1 | 10/2020 | Lavoie et al. |
| 2020/0390746 A1 | 12/2020 | Rands et al. |
| 2020/0397752 A1 | 12/2020 | Perez Castillo et al. |
| 2021/0015738 A1 | 1/2021 | LaRosa et al. |
| 2021/0085671 A1 | 3/2021 | Chadeayne |
| 2021/0108238 A1 | 4/2021 | Protzko |
| 2021/0145851 A1 | 5/2021 | Stamets |
| 2021/0236523 A1 | 8/2021 | Schindler et al. |
| 2021/0277433 A1 | 9/2021 | Protzko |
| 2021/0322306 A1 | 10/2021 | Espinoza et al. |
| 2021/0346347 A1 | 11/2021 | Witowski et al. |
| 2021/0353615 A1 | 11/2021 | Chadeayne |
| 2021/0363104 A1 | 11/2021 | Nivorozhkin et al. |
| 2021/0378969 A1 | 12/2021 | Rands et al. |
| 2021/0395201 A1 | 12/2021 | Rands et al. |
| 2022/0024956 A1 | 1/2022 | Slassi et al. |
| 2022/0031662 A1 | 2/2022 | Terwey |
| 2022/0071958 A1 | 3/2022 | Terwey |
| 2022/0079881 A1 | 3/2022 | Modi |
| 2022/0259147 A1 | 8/2022 | Feilding-Mellen |
| 2022/0267267 A1 | 8/2022 | Feilding-Mellen |
| 2022/0273628 A1 | 9/2022 | Liechti et al. |

(Continued)

FOREIGN PATENT DOCUMENTS

| | | |
|---|---|---|
| EP | 1336602 A1 | 8/2003 |
| WO | WO-9506638 A1 | 3/1995 |

(Continued)

OTHER PUBLICATIONS

Melting Point Determination, Melting Range (Year: 2012).*
The product Item No. 33586 of Cayman Chemical (Apr. 26, 2021) (Year: 2021).*
ACS Chem. Neurosci. 2018, 9, 1582-1590 (Year: 2018).*
Synthesis and Characterization of 5-MeO-DMT Succinate for Clinical Use ACS Omega 2020, 5, 49, 32067-32075 (Year: 2020).*
Sigma Succinic acid—Butanedioic acid (Year: 2023).*
Berge et al., J. Pharm. Sci. 1977, vol. 66 1-18.*
"Safety Data Sheet", Caymanchem.com, Cayman Chemical, Apr. 21, 2021, 6 pages., https://cdn.caymanchem.com/cdn/msds/33586m.pdf.
Brito-Da-Costa, et al., Toxicokinetics and toxicodynamics of ayahuasca alkaloids N, N-dimethyltryptamine (DMT), harmine, harmaline and tetrahydroharmine: Clinical and forensic impact, Pharmaceuticals, Oct. 23, 2020, 36 pages, vol. 13, No. 334.
Dalgleish, et al., Transdiagnostic approaches to mental health problems: Current status and future directions, J. Consult Clin Psychology, Mar. 2020, pp. 179-195Mar, vol. 88, No. 3.

(Continued)

*Primary Examiner* — Ana Z Muresan
(74) *Attorney, Agent, or Firm* — COOLEY LLP

(57) ABSTRACT

A N,N-dimethyltryptamine (DMT) succinate crystalline form.

16 Claims, 24 Drawing Sheets

(56) References Cited

U.S. PATENT DOCUMENTS

| | | |
|---|---|---|
| 2022/0304980 A1 | 9/2022 | Arnold et al. |
| 2022/0339139 A1 | 10/2022 | Rao et al. |
| 2023/0041584 A1 | 2/2023 | Perni et al. |
| 2023/0066720 A1 | 3/2023 | Perni et al. |
| 2023/0099972 A1 | 3/2023 | Rao et al. |
| 2023/0136824 A1 | 5/2023 | Rao et al. |
| 2023/0227407 A1 | 7/2023 | Perni et al. |
| 2023/0227421 A1 | 7/2023 | Perni et al. |
| 2023/0310374 A1 | 10/2023 | Rao et al. |
| 2023/0321039 A1 | 10/2023 | Rao et al. |
| 2023/0322735 A1 | 10/2023 | Kruegel |
| 2023/0357146 A1 | 11/2023 | Perni |
| 2024/0116896 A1 | 4/2024 | Khan et al. |
| 2024/0199544 A1 | 6/2024 | Fawaz et al. |
| 2024/0287107 A1 | 8/2024 | Khan |
| 2024/0400511 A1 | 12/2024 | Perni et al. |

FOREIGN PATENT DOCUMENTS

| | | |
|---|---|---|
| WO | WO-9617842 A1 | 6/1996 |
| WO | WO-0041755 A1 | 7/2000 |
| WO | WO-0051672 A1 | 9/2000 |
| WO | WO-0211800 A2 | 2/2002 |
| WO | WO-02068029 A2 | 9/2002 |
| WO | WO-02068030 A2 | 9/2002 |
| WO | WO-02068031 A2 | 9/2002 |
| WO | WO-02068032 A2 | 9/2002 |
| WO | WO-03000310 A2 | 1/2003 |
| WO | WO-03020350 A1 | 3/2003 |
| WO | WO-03026559 A2 | 4/2003 |
| WO | WO-03082393 A1 | 10/2003 |
| WO | WO-03084591 A1 | 10/2003 |
| WO | WO-03090812 A2 | 11/2003 |
| WO | WO-2006099416 A1 | 9/2006 |
| WO | WO-2010151258 A1 | 12/2010 |
| WO | WO-2011041870 A1 | 4/2011 |
| WO | WO-2013063492 A1 | 5/2013 |
| WO | WO-2018094106 A2 | 5/2018 |
| WO | WO-2019081764 A1 | 5/2019 |
| WO | WO-2019213551 A1 | 11/2019 |
| WO | WO-2020037372 A1 | 2/2020 |
| WO | WO-2020176597 A1 | 9/2020 |
| WO | WO-2020181194 A1 | 9/2020 |
| WO | WO-2020212951 A1 | 10/2020 |
| WO | WO-2021226041 A1 | 11/2021 |
| WO | WO-2021226416 A1 | 11/2021 |
| WO | WO-2021244831 A1 | 12/2021 |
| WO | WO-2021250434 A1 | 12/2021 |
| WO | WO-2021250435 A1 | 12/2021 |
| WO | WO-2022051670 A1 | 3/2022 |
| WO | WO-2022061242 A1 | 3/2022 |
| WO | WO-2022082058 A1 | 4/2022 |
| WO | WO-2022109050 A1 | 5/2022 |
| WO | WO-2022123232 A1 | 6/2022 |
| WO | WO-2022150675 A1 | 7/2022 |
| WO | WO-2022160056 A1 | 8/2022 |
| WO | WO-2022170442 A1 | 8/2022 |
| WO | WO-2022232179 A1 | 11/2022 |
| WO | WO-2022235514 A1 | 11/2022 |
| WO | WO-2022235529 A1 | 11/2022 |
| WO | WO-2022246572 A1 | 12/2022 |
| WO | WO-2022251351 A1 | 12/2022 |
| WO | WO-2022261383 A1 | 12/2022 |
| WO | WO-2023283386 A2 | 1/2023 |
| WO | WO-2023021112 A1 | 2/2023 |
| WO | WO-2023036473 A1 | 3/2023 |
| WO | WO-2023055992 A1 | 4/2023 |
| WO | WO-2023078604 A1 | 5/2023 |
| WO | WO-2023111544 A2 | 6/2023 |
| WO | WO-2023129956 | 7/2023 |
| WO | WO-2024054866 A2 | 3/2024 |
| WO | WO-2024092106 A2 | 5/2024 |
| WO | WO-2024/130140 A2 | 6/2024 |
| WO | WO-2024118767 A2 | 6/2024 |
| WO | WO-2024119075 A1 | 6/2024 |
| WO | WO-2024227149 A2 | 10/2024 |

OTHER PUBLICATIONS

International Search Report and Written Opinion for International Application No. PCT/US2022/030912, mailed Oct. 5, 2022, 20 pages.

Sherwood, A.M., et al., "Synthesis and Characterization of 5-MeO-DMT Succinate for Clinical Use", Dec. 2, 2020, ACS Omega 2020, 5, 49, 32067-32075, https://doi.org/10.1021/acsomega.0c05099; entire document, especially abstract.

Abiero et al., "Four Novel Synthetic Tryptamine Analogs Induce Head—Twitch Responses and Increase 5-HTR2a in the Prefrontal Cortex in Mice", Biomol Ther (Seoul). Jan. 1, 2020; 28(1): 83-91.

Andersson et al., "Psychoactive substances as a last resort—a qualitative study of self-treatment of migraine and cluster headaches", Harm Reduction Journal, Dec. 2017, 10 pages.

Archer et al., "5-Methoxy-N, N-dimethyltryptamine-induced analgesia is blocked by alpha-adrenoceptor antagonists in rats", British J. Pharmac., Oct. 1986, pp. 293-298.

Baker et al., "Neurochemical and neuropharmacological investigation of N-cyanoethyltryptamine, a potential prodrug of tryptamine", Proc West Pharmacol Soc., 1987; 30: 307-11.

Barker, "Administration of N,N-dimethyltryptamine (DMT) in psychedelic therapeutics and research and the study of endogenous DMT", Psychopharmacology (Berl). Jun. 2022; 239(6): 1749-1763. Epub Jan. 22, 2022, with erratum, 16 pages.

Barsuglia et al., "Intensity of mystical experiences occasioned by 5-MeO-DMT and comparison with a prior psilocybin study", Front. Psychol., Dec. 2018, 6 pages.

Benneyworth et al., "Complex discriminative stimulus properties of (+)lysergic acid diethylamide (LSD) in C57Bl/6J mice", Psychopharmacology (2005) 179, 854-862.

Berge, S.M. et al., "Pharmaceutical Salts", Journal of Pharmaceutical Sciences, Jan. 1977, vol. 66, No. 1, pp. 1-19.

Buchwald, Peter, "Soft drugs: design principles, success stories, and future perspectives", Expert Opin Drug Metab Toxicol. Aug. 2020; 16(8): 645-650. Epub Jun. 20, 2020.

Bugaenko et al., "Synthesis of indoles: recent advances", Russ. Chem. Rev., 2019, 88 (2)99-159, 62 pages.

Cameron et al. "A non-hallucinogenic psychedelic analogue with therapeutic potential", Nature; (2021), 589(7842): 474-479.

Carhart-Harris et al., "Psilocybin for treatment-resistant depression: fMRI-measured brain mechanisms", Scientific Reports, Oct. 2017, 7: 13187, 11 pages.

Carhart-Harris et al., "The Therapeutic Potential of Psychedelic Drugs: Past, Present and Future", Neuropsychopharmacology; 42, 2105-2113 (2017).

Carter et al., "Modulating the rate and rhythmicity of perceptual rivalry alternations with the mixed 5-HT2A and 5-HT1A agonist psilocybin", Neuropsychopharmacology, Jun. 2005, pp. 1154-1162.

CAS Registry No. 1152718-19-8, Benzenemethanamine, N-[4-(1,1-dimethylethyl)cyclohexyl]-2,4-difluoro-α-methyl-, Jun. 5, 2009, 1 page.

CAS Registry No. 1152826-22-6, Benzenemethanamine, 5-bromo-N-[4-(1,1-dimethylpropyl)cyclohexyl]-2-fluoro-, Jun. 7, 2009, 1 page.

CAS Registry No. 1154138-59-6, Benzenemethanamine, N-[4-(1,1-dimethylpropyl)cyclohexyl]-2,5-difluoro-, Jun. 9, 2009, 1 page.

CAS Registry No. 127456-43-3, Phenol, 2-[[[4-(1,1-dimethylethyl)cyclohexyl]amino]methyl]-4-(1,1-dimethylpropyl)-, trans- (9CI), Jun. 1, 1990, 1 page.

CAS Registry No. 127456-44-4, 1H-Inden-5-ol, 6-[[[4-(1,1-dimethylethyl)cyclohexyl]amino]methyl]-2,3-dihydro-, trans- (9CI), Jun. 1, 1990, 1 page.

CAS Registry No. 127456-45-5, Phenol, 4-(1,1-dimethylethyl)-2-[[[4-(1,1-dimethylethyl) cyclohexyl]amino]methyl]-, trans- (9CI), Jun. 1, 1990, 1 page.

(56) References Cited

OTHER PUBLICATIONS

CAS Registry No. 127456-46-6, Phenol, 4-(1,1-dimethylethyl)-2-[[[4-(1,1-dimethylethyl)cyclohexyl]amino]methyl]-6-methyl-, hydrochloride, trans-(9CI), Jun. 1, 1990, 1 page.
CAS Registry No. 127456-52-4, Phenol, 2-[[[4-(1,1-dimethylethyl)cyclohexyl]amino]methyl]-4-(1-methylethyl)-, cis-(9CI), Jun. 1, 1990, 1 page.
CAS Registry No. 127456-56-8, Phenol, 4-chloro-2-[[[4-(1,1-dimethylethyl)cyclohexyl]amino]methyl]-, trans-(9CI), Jun. 1, 1990, 1 page.
CAS Registry No. 127456-57-9, Phenol, 2-[[[4-(1,1-dimethylethyl)cyclohexyl]amino]methyl]-4-fluoro-, trans-(9CI), Jun. 1, 1990, 1 page.
CAS Registry No. 1308467-14-2, 1,2-Benzenediol, 3-[[[4-(1,1-dimethylpropyl)cyclohexyl]amino]methyl]-, Jun. 10, 2011, 1 page.
CAS Registry No. 1405571-87-0, Benzenemethanamine, 2-bromo-N-[4-(1,1-dimethylpropyl)cyclohexyl]-5-fluoro-, Nov. 23, 2012, 1 page.
CAS Registry No. 1406541-63-6, Phenol, 2-chloro-4-[[[4-(1,1-dimethylpropyl)cyclohexyl]amino]methyl]-, Nov. 25, 2012, 1 page.
CAS Registry No. 1411655-23-6, Benzenemethanamine, N-[4-(1,1-dimethylpropyl)cyclohexyl]-2,3-difluoro-, Dec. 5, 2012, 1 page.
CAS Registry No. 1456349-79-3, Benzenemethanamine, 2,3-dichloro-N-[4-(1,1-dimethylpropyl)cyclohexyl]-, Oct. 6, 2013, 1 page.
CAS Registry No. 1458497-71-6, Benzenemethanamine, 2,4-dichloro-N-[4-(1,1-dimethylethyl)cyclohexyl]-α-methyl-, Oct. 15, 2013, 1 page.
CAS Registry No. 1459328-13-2, Phenol, 2-bromo-4-[[[4-(1,1-dimethylpropyl)cyclohexyl]amino]methyl]-, Oct. 16, 2013, 1 page.
CAS Registry No. 1490220-45-5, Benzenemethanamine, 2-bromo-5-chloro-N-[4-(1,1-dimethylpropyl)cyclohexyl]-, Dec. 8, 2013, 1 page.
CAS Registry No. 1515984-46-9, Benzamide, N-(4-aminocyclohexyl)-3-chloro-N,5-dimethyl-, Jan. 10, 2014, 1 page.
CAS Registry No. 1542027-51-9, Phenol, 3-chloro-2-[[[4-(1,1-dimethylpropyl)cyclohexyl]amino]methyl]-, Feb. 11, 2014, 1 page.
CAS Registry No. 1624268-56-9, Benzamide, 4-[[[4-(1,1-dimethylethyl)cyclohexyl]amino]methyl]-N-methyl-, Sep. 22, 2014, 1 page.
CAS Registry No. 1712122-27-4, Benzenemethanamine, 5-chloro-N-[4-(1,1-dimethylpropyl)cyclohexyl]-2-fluoro-, May 25, 2015, 1 page.
CAS Registry No. 1772618-27-5, Phenol, 3-[[[4-(1,1-dimethylpropyl)cyclohexyl]amino]methyl]-5-fluoro-, Jun. 3, 2015, 1 page.
CAS Registry No. 1775706-37-0, Phenol, 2-chloro-6-[[[4-(1,1-dimethylpropyl)cyclohexyl]amino]methyl]-, Jun. 8, 2015, 1 page.
CAS Registry No. 1858436-76-6, Bicyclo[3.1.0]hexan-2-amine, N-[(3-chloro-5-methylphenyl)methyl]-, Feb. 3, 2016, 1 page.
CAS Registry No. 1931388-10-1, Benzenemethanamine, 2,5-dichloro-N-[4-(1,1- dimethylpropyl)cyclohexyl]-, Jun. 14, 2016, 1 page.
CAS Registry No. 1939264-55-7, Phenol, 4-[[[4-(1,1-dimethylpropyl)cyclohexyl]amino]methyl]-2-fluoro-, Jun. 26, 2016, 1 page.
CAS Registry No. 1939792-99-0, Benzenemethanamine, 5-bromo-2-chloro-N-[4-(1,1-dimethylpropyl)cyclohexyl]-, Jun. 27, 2016, 1 page.
CAS Registry No. 1962333-15-8, Benzenemethanamine, N-[4-(1,1-dimethylpropyl)cyclohexyl]-5-fluoro-2-methyl-, Jul. 29, 2016, 1 page.
CAS Registry No. 2032268-58-7, Cyclohexanecarboxylic acid, 4-[[[(3-chloro-5-methylphenyl)methyl]amino]-, Nov. 15, 2016, 1 page.
CAS Registry No. 2199998-08-6, Cyclohexanecarboxylic acid, 2-[[(3-chloro-5-methylphenyl)methyl]amino]-1-methyl-, Mar. 27, 2018, 1 page.
CAS Registry No. 2202151-69-5, Cyclohexanecarboxylic acid, 3-[[(3-chloro-5-methylphenyl)methyl]amino]-, Mar. 30, 2018, 1 page.
CAS Registry No. 2322790-81-6, Benzenemethanamine, N-[4-(1,1-dimethylethyl)cyclohexyl]-3-(trifluoromethyl)-, Jun. 2, 2019, 1 page.
CAS Registry No. 2419600-39-6, Benzenemethanamine, 3-chloro-N-[4-(1,1-dimethylpropyl)cyclohexyl]-5-methyl-, Jun. 5, 2020, 1 page.
CAS Registry No. 415970-94-4, Benzenemethanamine, N-[4-(1,1-dimethylethyl)cyclohexyl]-3,5-dimethoxy-, May 15, 2002, 1 page.
CAS Registry No. 744981-83-7, Phenol, 2,6-dibromo-4-[[[4-(1,1-dimethylethyl)cyclohexyl]amino]methyl]-, Sep. 15, 2004, 1 page.
CAS Registry No. 793633-39-3, Phenol, 4-(1,1-dimethylethyl)-2-[[[trans-4-(1,1-dimethylethyl)cyclohexyl]amino]methyl]-6-methyl-, Dec. 6, 2004, 1 page.
Chegaev, et al., "NO-donor melatonin derivatives: synthesis and in vitro pharmacological characterization", Journal of pineal research, May 2007, pp. 371-385.
Chen, et al., "Structure-activity relationships in a series of 5-[(2, 5-dihydroxybenzyl) amino] salicylate inhibitors of EGF-receptor-associated tyrosine kinase: importance of additional hydrophobic aromatic interactions", Journal of Medicinal Chemistry, Mar. 1994, pp. 845-859.
ClinicalTrials.gov, Effects of Dimethyltryptamine in Healthy Subjects (DMT), Apr. 20, 2020, 9 pages, entire document, especially p. 2 table, p. 4 table row 1. Retrieved on Jun. 24, 2022 from https://clinicaltrials.gov/ct2/show/NCT04353024.
Cocchi et al., "Novel Psychoactive Phenethylamines: Impact on Genetic Material", International Journal of Molecular Sciences, 2020, 17 pages.
Corne, "A Possible Correlation between Drug-Induced Hallucinations in Man and a Behavioural Response in Mice", Psychopharmacologia. 1967; 11(1): 65-78.
Custodio et al., "25B-NBOMe, a novel N-2-methoxybenzyl-phenethylamine (NBOMe) derivative, may induce rewarding and reinforcing effects via a dopaminergic mechanism: evidence of abuse potential", Addiction Biology, Nov. 2019, 12 pages.
Dakic et al., "Short term changes in the proteome of human cerebral organoids induced by 5-MeO-DMT", Scientific Reports, 2017, 13 pages.
Davis et al., "5-methoxy-N, N-dimethyltryptamine (5-MeO-DMT) used in a naturalistic group setting is associated with unintended improvements in depression and anxiety", The American Journal of Drug and Alcohol Abuse, 2019, 10 pages.
Davis, et al., "The epidemiology of 5-methoxy- N, N-dimethyltryptamine (5-MeO-DMT) use: Benefits, consequences, patterns of use, subjective effects, and reasons for consumption", J Psychopharmacol, Jul. 2018; 32(7): 779-792. Epub Apr. 30, 2018.
de Barros et al., "Synthesis of 25X-BOMes and 25X-NBOHs (X=H, I, Br) for pharmacological studies and as reference standards for forensic purposes", Tetrahedron Letters, Mar. 2021, 4 pages.
Dunlap et al., "Identification of psychoplastogenic N, N-dimethylaminoisotryptamine (isoDMT) analogues through structure-activity relationship studies", J. Med. Chem. 2020, pp. 1142-1155.
Durham, "Regulation of calcitonin gene-related peptide secretion by a serotonergic antimigraine drug", The Journal of Neuroscience, May 1, 1999, pp. 3423-3429.
Glennon et al., "Influence of amine substituents on 5-HT2A versus 5-HT2C binding of phenylalkyl-and indolylalkylamines", Journal of Medicinal Chemistry, 1994, pp. 1929-1935.
Glennon et al., "Synthesis and evaluation of a novel series of N,N-dimethylisotryptamines", J Med Chem. Jan. 1984; 27(1): 41-5.
Gonzalez-Maeso et al., "Hallucinogens Recruit Specific Cortical 5-HT2A Receptor-Mediated Signaling Pathways to Affect Behavior", Neuron, Feb. 2007, 53, 439-452.
Gribble, "Recent developments in indole ring synthesis-methodology and applications", Journal of the Chemical Society, Perkin Transactions, 2000, pp. 1045-1075.
Grundke et al., "Photochemical α-Aminonitrile Synthesis Using Zn-Phthalocyanines as Near-Infrared Photocatalysts", J Org Chem. May 6, 2022; 87(9): 5630-5642. Epub Apr. 14, 2022. With supporting information, 60 pages.
Gurevich and Gurevich, "GPCR Signaling Regulation: The Role of GRKs and Arrestins", Front Pharmacol. Feb. 19, 2019: 10: 125. eCollection 2019, 11 pages.
Halberstadt et al., "Differential contributions of serotonin receptors to the behavioral effects of indoleamine hallucinogens in mice", J Psychopharmacol., Nov. 2011, pp. 1548-1561.

(56) References Cited

OTHER PUBLICATIONS

Halberstadt, "Recent Advances in the Neuropsychopharmacology of Serotonergic Hallucinogens", Behav. Brain Res., 2015, pp. 99-120.
Hamada et al., "Water-soluble prodrugs of dipeptide HIV protease inhibitors based on O→N intramolecular acyl migration: Design, synthesis and kinetic study", Bioorg Med Chem., Jan. 2004, pp. 159-170.
Hansen et al., "Synthesis and pharmacological evaluation of N-benzyl substituted 4-bromo-2,5-dimethoxyphenethylamines as 5-HT2A/2C partial agonists", Bioorganic & Medicinal Chemistry, 2015, pp. 3933-3937.
Hansen et al., "Synthesis and Structure-Activity Relationships of N-Benzyl Phenethylamines as 5-HT2A/2C Agonists", ACS Chemical Neuroscience, 2014, pp. 243-249.
Harriott et al., "Animal models of migraine and experimental techniques used to examine trigeminal sensory processing", J Headache Pain. Aug. 29, 2019; 20(1): 91. 15 pages.
Healthline, "How Long Does DMT Last?", Nov. 2019, 12 pages, entire document, especially p. 1 para 1-3. Retrieved om Jun. 24, 2022 from https://www.healthline.com/health/how-long-does-dmt-last.
Humphrey, et al., "Practical methodologies for the synthesis of indoles", Chem. Review, Jul. 2006, pp. 2875-2911.
Huttunen, et al., "Prodrugs-from Serendipity to Rational Design", Pharmacal Rev., Sep. 2011, pp. 750-771.
International Preliminary Report on Patentability for International Application No. PCT/US2022/026396 dated Nov. 9, 2023, 8 pages.
International Search Report and Written Opinion for International Application No. PCT/US2022/026396, mailed Jul. 28, 2022, 10 pages.
International Search Report and Written Opinion for International Application No. PCT/US2022/032918, mailed Oct. 12, 2022, 10 pages.
International Search Report and Written Opinion for International Application No. PCT/US2022/045336 dated Jan. 13, 2023, 14 pages.
Invitation to Pay Additional Fees for International Application No. PCT/US2022/030912, mailed Jul. 28, 2022, 8 pages.
Invitation to Pay Additional Fees for International Application No. PCT/US2022/032918, mailed Aug. 12, 2022, 2 pages.
Invitation to pay additional fees for International Application No. PCT/US2023/073574, dated Nov. 6, 2023, 2 pages.
Invitation to Pay Fee for International Application No. PCT/US2022/082465 dated Mar. 16, 2023, 3 pages.
Kaminska et al., "25C-NBOMe short characterization", Forensic Toxicology, 2020, pp. 490-495.
Klein, et al, "Structure-activity relationships in potentially hallucinogenic N, N-dialkyltryptamines substituted in the benzene moiety", J. Med. Chen, Aug. 1982, pp. 908-913.
Klein et al., "Toward selective drug development for the human 5-hydroxytryptamine 1E receptor: a comparison of 5-hydroxytryptamine 1E and 1F receptor structure-affinity relationships", J Pharmacol Exp Ther. Jun. 2011; 337(3): 860-7. Epub Mar. 21, 2011.
Kraehenmann et al., "Dreamlike effects of LSD on waking imagery in humans depend on serotonin 2A receptor activation", Psychopharmacology, 2017, pp. 2031-2046.
Kraehenmann et al., "LSD Increases Primary Process Thinking via Serotonin 2A Receptor Activation", Front. Pharmacol., 2017, 9 pages.
Krise, J. P., et al., "Novel prodrug approach for tertiary amines: synthesis and preliminary evaluation of N-phosphonooxymethyl prodrugs", J Med Chem. Aug. 12, 1999; 42(16): 3094-100.
Kucklander, et al., "Darstellung und Oxidation von 2-(2, 5-Dihydroxyphenyl)-ethylamin-Derivaten, II/Synthesis and Oxidation of 2-(2, 5-Dihydroxyphenyl)-ethylamine Derivatives, II", Zeitschrift für Naturforschung B, 1987, pp. 1567-1577 (with English abstract).
Li et al., "Treatment of breast and lung cancer cells with a N-7 benzyl guanosine monophosphate tryptamine phosphoramidate pronucleotide (4Ei-1) results in chemosensitization to gemcitabine and induced elF4E proteasomal degradation", Mol Pharm., Feb. 2013, pp. 523-531.
Lima da Cruz et al., "Corrigendum: A Single Dose of 5-MeO-DMT Stimulates Cell Proliferation, Neuronal Survivability, Morphological and Functional Changes in Adult Mice Ventral Dentate Gyrus", Front. Mol. Neurosci., 2018, 11 pages.
Lyon et al., "Indolealkylamine analogs share 5-HT2 binding characteristics with phenylalkylamine hallucinogens", European Journal of Pharmacology, 1988, pp. 291-297.
Madsen et al., "Psilocybin-induced reduction in chronic cluster headache attack frequency correlates with changes in hypothalamic functional connectivity", medRxiv. Jul. 10, 2022: Jul. 2022.
Madsen et al., "Psychedelic effects of psilocybin correlate with serotonin 2A receptor occupancy and plasma psilocin levels", Neuropsychopharmacology (2019) 44: 1328- 1334.
McBride, "Bufotenine: Toward an Understanding of Possible Psychoactive Mechanisms", Journal of Psychoactive Drugs, Jul.-Sep. 2000, pp. 321-331.
McClure-Begley and Roth, "The promises and perils of psychedelic pharmacology for psychiatry", Nat Rev Drug Discov. Jun. 2022; 21(6): 463-473. Epub Mar. 17, 2022.
Mertens and Preller, "Classical Psychedelics as Therapeutics in Psychiatry—Current Clinical Evidence and Potential Therapeutic Mechanisms in Substance Use and Mood Disorders", Pharmacopsychiatry. Jul. 2021; 54(4): 176-190. Epub Jan. 20, 2021.
Milne et al., "Metabolic engineering of *Saccharomyces cerevisiae* for the de novo production of psilocybin and related tryptamine derivatives", Metabolic Engineering, Jul. 2020, pp. 25-36.
Mithoefer et al., "The safety and efficacy of ±3, 4-methylenedioxymethamphetamine-assisted psychotherapy in subjects with chronic, treatment-resistant posttraumatic stress disorder: the first randomized controlled pilot study", Journal of Psychopharmacology, Apr. 2010, pp. 439-452.
National Center for Biotechnology Information (2023). PubChem Substance Record for SID 309311543, SID 309311543, Source: Aurora Fine Chemicals LLC. Modified Jan. 30, 2016, retrieved Nov. 7, 2023, from https://pubchem.ncbi.nlm.nih.gov/substance/309311543, 5 pages.
Nichols, "Hallucinogens", Pharmacol. Ther., 2004, pp. 131-181.
Nichols, "Structure-Activity Relationships of Phenethylamine Hallucinogens", J. Pharm. Sciences, 1981, pp. 839-849.
Olson, David E., "The Subjective Effects of Psychedelics May Not Be Necessary for Their Enduring Therapeutic Effects", ACS Pharmacol Transl Sci. Apr. 9, 2021; 4(2): 563-567. Published online Dec. 10, 2020.
Ott, J., "Pharmepena-psychonautics: human intranasal, sublingual and oral pharmacology of 5-methoxy-N, N-dimethyl-tryptamine", Journal of Psychoactive Drugs, Dec. 2001, pp. 403-407.
Ott, J., "Pharmañopo-Psychonautics: Human intranasal, sublingual, intrarectal, pulmonary and oral pharmacology of bufotenine", Journal of Psychoactive Drugs, Sep. 2001, pp. 273-281.
Pandy-Szekeres et al., "GPCRdb in 2023: state-specific structure models using AlphaFold2 and new ligand resources", Nucleic Acids Res. Jan. 6, 2023; 51(D1): D395-D402.
Pokorny et al., "Modulatory effect of the 5-HT1A agonist buspirone and the mixed non-hallucinogenic 5-HT1A/2A agonist ergotamine on psilocybin-induced psychedelic experience", Eur. Neuropsychopharmacol., Apr. 2016, pp. 756-766.
Pottie, et al., "Identification of psychedelic new psychoactive substances (NPS) showing biased agonism at the 5-HT2AR through simultaneous use of β-arrestin 2 and miniGαq bioassays", Biochemical pharmacology, Dec. 2020, 38 pages.
Preller et al., "Effects of serotonin 2A/1A receptor stimulation on social exclusion processing", PNAS, May 3, 2016, vol. 113, No. 18, 5119-5124.
Preller et al., "Role of the 5-HT2A Receptor in Self- and Other-Initiated Social Interaction in Lysergic Acid Diethylamide-Induced States: A Pharmacological fMRI Study", J. Neurosci., Apr. 2018, 38(14): 3603-3611.
Preller et al., "The Fabric of Meaning and Subjective Effects in LSD-Induced States Depend on Serotonin 2A Receptor Activation", Current Biology, Feb. 2017, pp. 451-457.

(56) References Cited

OTHER PUBLICATIONS

PubChem SID 385740476, 2-(2,5-dimethoxy-4-(propan-2-yt)phenyl)-N-(2methoxybenzyl)ethanamine, Sep. 23, 2019, 6 pages, retrieved from https://pubchem.ncbi.nlm.nih.gov/substance/385740476.
Pubchem, SID 627609, Sep. 2004, 8 pages. Retrieved from the Internet: https://pubchem.ncbi.nlm.nih.gov/substance/627609.
PubChem-SID-310331158, Modify Date: Feb. 15, 2015, p. 2.
PubChem-SID-369863280, Modify Date: May 25, 2018, p. 2.
Puledda et al., "An update on migraine: current understanding and future directions", J Neurol (2017) 264:2031-2039.
Ray, T., "Psychedelics and the Human Receptorome", PLoS One (2010) 5(2): e9019, 17 pages.
Riba, et al., "Metabolism and urinary disposition of N,N-dimethyltryptamine after oral and smoked administration: a comparative study", Drug Test Anal. May 2015;7(5): 401-6. Epub Jul. 28, 2014.
Roth et al., "High-affinity Agonist Binding Is Not Sufficient for Agonist Efficacy at 5-Hydroxytryptamine2A Receptors: Evidence in Favor of a Modified Ternary Complex Model", The Journal of Pharmacology and Experimental Therapeutics, 1997, vol. 280, No. 2, pp. 576-583.
Ruiz et al., "Routes of Drug Administration: Dosage, Design, and Pharmacotherapy Success", Routes of Drug Administration, Chapter 6, Jan. 2018, 43 pages.
Sargent et al., "Radiohalogen-Labeled Imaging Agents. 3. Compounds for Measurement of Brain Blood Flow by Emission Tomography", Journal of Medicinal Chemistry (1984), 27(8), 1071-1077.
Schifano et al., "New psychoactive substances (NPS) and serotonin syndrome onset: A systematic review", Experimental Neurology (2021), 339, 113638 (Author manuscript, 29 pages).
Schindler et al., "Exploratory Controlled Study of the Migraine-Suppressing Effects of Psilocybin", Neurotherapeutics, Jan. 2021; 18(1): 534-543. doi: 10.1007/s13311-020-00962-y. Epub Nov. 12, 2020.
Shen et al., "Psychedelic 5-Methoxy-N,N-dimethyltryptamine: Metabolism, Pharmacokinetics, Drug Interactions, and Pharmacological Actions", Curr Drug Metab., Oct. 2010 ; 11(8): 659-666.
Sizemore, T.R, and Dacks, A.M., "Circadian Clocks: Mosquitoes Master the Dark Side of the Room", Curr Biol. Aug. 17, 2020; 30(16): R932-R934.
Strassman, "Dose-response study of N,N-dimethyltryptamine in humans. I. Neuroendocrine, autonomic, and cardiovascular effects", Arch Gen Psychiatry. Feb. 1994; 51(2): 85-97.
Strassman, "N-dimethyltryptamine in humans: II. Subjective effects and preliminary results of a new rating scale", Arch Gen Psychiatry. Feb. 1994; 51(2): 98-108.
Substance Record for SID 433987242 to PubChem (hereinafter, "PubChem '242"), Sep. 2020, 7 pages.
Terry, Alvin V., "Drugs that target serotonergic receptors", Cognitive Enhancing Drugs, Introduction, pp. 79-80, 2004, 2 pages.
Third Party Observation received for International Application No. PCT/US2022/045336, filed May 24, 2023 and received Jun. 2, 2023, 8 pages.
Tirapegui et al., "Synthesis of N-(halogenated) benzyl analogs of superpotent serotonin ligands", J. Chil. Chem. Soc., (2014) 59, No. 3, pp. 2625-2627.
Titeler et al., "Radioligand binding evidence implicates the brain 5-HT2 receptor as a site of action for LSD and phenylisopropylamine hallucinogens", Psychopharmacology (1988) 94, 213-216.
Tomaszewski et al., "Benzofuran Bioisosteres of Hallucinogenic Tryptamines", J. Med. Chem., 1992, 35, pp. 2061-2064.
United States Patent and Trademark Office, International Search Report and Written Opinion for International Application No. PCT/US2022/082465 dated Jun. 6, 2023, 11 pages.
Uthaug et al., "A single inhalation of vapor from dried toad secretion containing 5-methoxy-N,N-dimethyltryptamine (5-MeO-DMT) in a naturalistic setting is related to sustained enhancement of satisfaction with life, mindfulness-related capacities, and a decrement of psychopathological symptoms", Psychopharmacology (2019) 236: 2653-2666.
Uthaug et al., "Prospective examination of synthetic 5-methoxy-N,N-dimethyltryptamine inhalation: effects on salivary IL-6, cortisol levels, affect, and non-judgment", Psychopharmacology (2020) 237: 773-785.
Valle et al., "Inhibition of alpha oscillations through serotonin-2A receptor activation underlies the visual effects of ayahuasca in humans", Eur. Neuropsychopharm (2016) 26, 1161-1175 (Author-edited version, 23 pages).
Vollenweider et al., "Psilocybin induces schizophrenia-like psychosis in humans via a serotonin-2 agonist action", Neuroreport (1998) 9, 3897-3902 (8 pages).
Vollenweider et al., "Psychedelic drugs: neurobiology and potential for treatment of psychiatric disorders", Nature Reviews Neuroscience, Nov. 2020, vol. 21, pp. 611-624.
Wang et al., "Anti-inflammatory and analgesic actions of bufotenine through inhibiting lipid metabolism pathway", Biomedicine & Pharmacotherapy (2021) 140: 111749, 11 pages.
Wey, "Structure-based design, synthesis, and biological evaluation of indomethacin derivatives as cyclooxygenase-2 inhibiting nitric oxide donors", Journal of medicinal chemistry, Dec. 2007, pp. 6367-6382.
Wikipedia, "Perfusion", Dec. 29, 2020 (Dec. 29, 2020), retrieved on Jun. 24, 2022 from https://en.wikipedia.org/w/index.php?title=Perfusion&oldid=996968059; entire document, especially p. 1 para 1.
Winter et al., "Psilocybin-induced stimulus control in the rat", Pharmacol. Biochem. Behav. (2007) 87, 472-480 (18 pages).
Winter et al., "The Paradox of 5-Methoxy-N,N-Dimethyltryptamine: An Indoleamine Hallucinogen That Induces Stimulus Control Via 5-HT1A Receptors," Pharmacology Biochemistry and Behavior, 2000, vol. 65, No. 1, pp. 75-82.
Wood et al., "Prevalence of use and acute toxicity associated with the use of NBOMe drugs", Clinical Toxicology, 2015, 53: 85-92.
Yu, A.M., "Indolealkylamines: Biotransformations and Potential Drug-Drug Interactions", The AAPS Journal, Jun. 2008, vol. 10, No. 2, pp. 242-253.
Zamberlan et al., "The Varieties of the Psychedelic Experience: A Preliminary Study of the Association Between the Reported Subjective Effects and the Binding Affinity Profiles of Substituted Phenethylamines and Tryptamines", Front Integr Neurosci. Nov. 8, 2018: 12: 54. eCollection 2018, 22 pages.
Barker, "N, N-Dimethyltryptamine (DMT), an Endogenous Hallucinogen: Past, Present, and Future Research to Determine Its Role and Function," Front Neurosci. Aug. 6, 2018:12: 536. doi: 10.3389/fnins.2018.00536. eCollection 2018. 17 pages.
Bergin, "The structure of the catecholamines. II. The crystal structure of dopamine hydrochloride." Acta Crystallogr B Struct Crystallogr Cryst Chem. Nov. 15, 1968; 24(11): 1506-10. doi: 10.1107/s0567740868004553.
Bibi et al., "Use of Permeapad® for prediction of buccal absorption: A comparison to in vitro, ex vivo and in vivo method," Eur J Pharm Sci. Oct. 10, 2016: 93: 399-404. doi:10.1016/j.ejps.2016.08.041. Epub Aug. 24, 2016.
Brandt et al., "Analytical methods for psychoactive N,N-dialkylated tryptamines," Trends in Analytical Chemistry, vol. 29, No. 8, 2010, pp. 858-869.
Carvalho et al., "Mucoadhesive drug delivery systems," BJPS, vol. 46, n. 1, Jan./Mar. 2010. 18 pages.
Falkenberg et al., "The crystal and molecular structure of (N,N)-dimethyltryptamine." Acta Crystallogr., Sect B28, 3075-3083, https://doi.org/10.1107/S0567740872007435. 9 pages.
Gaujac et al. "Determination of N,N-dimethyltryptamine in beverages consumed in religious practices by headspace solid-phase microextraction followed by gas chromatography ion trap mass spectrometry," Talanta. Mar. 15, 2013: 106: 394-8. doi: 10.1016/j.talanta.2013.01.017. Epub Feb. 1, 2013.
Glatfelter G, et al., "Synthesis, Structural Characterization, and Pharmacological Activity of Novel Quaternary Salts of 4-Substituted Tryptamines," ACS Omega, Jul. 2022, vol. 7(28), pp. 24888-24894.
Griffiths, R. R., et al. "Psilocybin produces substantial and sustained decreases in depression and anxiety in patients with life-threatening

(56) References Cited

OTHER PUBLICATIONS cancer: a randomized double-blind trial," Journal of Psychopharmacology 30(12), 1181-1197, 2016.

International Preliminary Report on Patentability for International Application No. PCT/US2022/030912 dated Dec. 7, 2023, 10 pages.

International Preliminary Report on Patentability for International Application No. PCT/US2022/032918 dated Dec. 21, 2023, 7 pages.

International Preliminary Report on Patentability for International Application No. PCT/US2022/045336, mailed Apr. 11, 2024, 7 pages.

International Search Report and Written Opinion for International Application No. PCT/US2023/073574 dated Feb. 16, 2024, 13 pages.

International Search Report and Written Opinion for International Application No. PCT/US2023/077879, mailed Apr. 4, 2024, 11 pages.

International Search Report and Written Opinion for International Application No. PCT/US2023/082080, mailed Apr. 4, 2024, 8 pages.

International Search Report and Written Opinion for PCT Application No. PCT/US2023/084319 mailed May 20, 2024, 13 pages.

Malaca S et al., "Toxicology and Analysis of Psychoactive Tryptamines", International Journal of Molecular Science, Dec. 2020, vol. 21(23), pp. 1-30.

Puri et al., "Thiolation of Biopolymers for Developing Drug Delivery Systems with Enhanced Mechanical and Mucoadhesive Properties: A Review," Polymers (Basel). Aug. 11, 2020; 12(8): 1803. doi: 10.3390/polym12081803. 27 pages.

Shen L, et al., "Bufotenines-loaded liposome exerts antiinflammatory, analgesic effects and reduce gastrointestinal toxicity through altering lipid and bufotenines metabolism", Biomed Pharmacother, Sep. 2022, vol. 153, pp. 1-12.

Banker, G. S., et al., "Prodrugs", Modern Pharmaceutics, Third Edition, Revised, and Expanded, Marcel Dekker, Inc. (1996); pp. 451 and 596.

Bergin, "Preliminary X-ray crystallographic study of some psychoactive indole bases," Department of Medical Physics, Feb. 13, 1968, 1 page.

Declaration of Majed Fawaz under 37 C.F.R. § 1.130, dated Jun. 2024, 2 pages.

Gaujac et al., "Investigations into the polymorphic properties of N, N-dimethyltryptamine by X-ray diffraction and differential scanning calorimetry," Microchemical Journal 110, Mar. 2, 2013, 12 pages.

International Search Report and Written Opinion for International Application No. PCT/US2024/026797 mailed Sep. 6, 2024, 10 pages.

International Search Report and Written Opinion for International Application No. PCT/US2024/049678, mailed Jan. 21, 2025, 9 pages.

International Search Report and Written Opinion for PCT Application No. PCT/US2024/036639 mailed Sep. 23, 2024, 11 pages.

International Search Report and Written Opinion for PCT Application No. PCT/US2024/038804 mailed Dec. 17, 2024, 14 pages.

International Search Report and Written Opinion for PCT Application No. PCT/US2024/039503 mailed Nov. 5, 2024, 17 pages.

International Search Report and Written Opinion for PCT Application No. PCT/US2024/045494 mailed Nov. 15, 2024, 11 pages.

Invitation to Pay Additional Fees for International Application No. PCT/US2024/026797 mailed Jun. 25, 2024, 2 pages.

Invitation to Pay Additional fees for International Application No. PCT/US2024/038804, mailed Sep. 23, 2024, 3 pages.

Invitation to pay additional fees for International Application No. PCT/US2024/039503, dated Sep. 10, 2024, 2 pages.

Pubchem CID 156821129, created Nov. 20, 2021, Modify date Aug. 23, 2024, available at: https://pubchem.ncbi.nlm.nih.gov/compound/156821129, 10 pages.

Pubchem CID 6089, Dimethyltryptamine, Create date: Mar. 26, 2005 (Mar. 26, 2005), 6 pages.

Pubchem CID 88309097, Created date Feb. 12, 2015, Modified date Nov. 9, 2024, available at: https://pubchem.ncbi.nlm.nih.gov/compound/88309097, 8 pages.

Thoai, et al., "Design and Synthesis of Sustain-Acting Melatonin Prodrugs", Sep. 12, 2013 (Sep. 12, 2013), Journal of Chemistry, vol. 2013, Issue 1, pp. 1-6.

Wolff, M., "Burger's Medicinal Chemistry and Drug Discovery", Fifth Edition, John Wiley & Sons (1995); 1: 975-977.

\* cited by examiner

Figure 1: XRPD patterns of DMT fumarate Form A

Figure 2: XRPD for DMT Succinate Form A

Figure 3: XRPD for DMT Malate Form A

Figure 5: XRPD for DMT Ovalate Form A

Figure 6: TGA (top) and DSC (bottom) thermograms for DMT Sulfate Form A

Figure 7: TGA (top) and DSC (bottom) thermograms for DMT Oxalate Form A

Figure 8: TGA (top) and DSC (bottom) thermograms for DMT Fumarate Form A

Figure 9: TGA (top) and DSC (bottom) thermograms for DMT Malate Form A

Figure 10: TGA (top) and DSC (bottom) thermograms for DMT Succinate Form A

Figure 11: DVS isotherm for DMT Fumarate Form A

Figure 12: DVS isotherm for DMT Malate Form A

Figure 13: DVS isotherm for DMT Succinate Form A

Figure 14: Variable temperature XRPD analysis for DMT Succinate Form A

Figure 15: DSC isotherm for DMT Succinate Form A prepared using EtOH as solvent

XRPD for DMT Succinate Form A prepared using EtOH (top) and acetone (bottom)

XRPD data of DMT Succinate Form A prepared at milligram scale (XRPD, top) and scaled up to gram scale (SCXRD, bottom)

DVS isotherm for DMT Succinate Form A from scale up batch

Figure 19: TGA (top) and DSC (bottom) thermograms for DMT Succinate Form A from scale up batch Figure 20: DSC analysis of a physical mixture of DMT Succinate Form A and Succinic acid at an overall composition of 0.34 mole fraction of DMT Figure 21: Hot stage micrographs of DMT Succinate Form A prepared from acetone (small-scale) confirming melt at 142°C Figure 22: Hot stage micrographs of DMT Succinate Form A prepared from EtOH (large scale)

Figure 23: XRPD pattern for DMT Phosphate

Melting points of the five salt forms compared to the free base

N, N-DIMETHYLTRYPTAMINE SALTS AND CRYSTALLINE SALT FORMS

CROSS-REFERENCE TO RELATED APPLICATIONS

The present application claims priority to, and the benefit of, U.S. Provisional Patent Application No. 63/192,938, filed May 25, 2021, the entire contents of which are incorporated herein by reference in its entirety for all purposes.

FIELD

The present disclosure relates to new N,N-dimethyltryptamine salts and crystalline salt forms, their preparation and use thereof. The new salts and salt forms may be incorporated into pharmaceutical compositions for treating neurological diseases and conditions.

BACKGROUND

N,N-dimethyltryptamine (hereinafter "DMT") has therapeutic value as a psychedelic, with intrinsic properties making it an attractive possible medication, especially for neurological diseases and conditions. However, DMT free base, isolated as clear or white crystals, has a low melting point between 44.6° C. and 46.8° C., and extremely low solubility in water. In solution, DMT free base has a fast degradation rate and should be stored at minus 20° C., protected from air and light (Brito-da-Costa et al, Pharmaceuticals 2020, 13, 334). Salts of DMT have been prepared with improved solubility, including the hemihydrate fumarate and hydrochloride salts. However, a need still exists for new DMT salt forms which exhibit physicochemical properties superior to DMT free base, particularly to facilitate improved drug formulation (e.g. solubility, stability) and performance (e.g. bioavailability). The present disclosure solves this need by providing novel DMT salt forms which, when compared to DMT free base, have improved melting point (higher), aqueous solubility (higher) and/or hygroscopicity (lower) characteristics.

SUMMARY

Described herein are new salts and crystalline salt forms of DMT. Specifically, the salt forms DMT fumarate Form A, DMT succinate Form A, DMT malate Form A, DMT oxalate Form A, and DMT sulfate Form A are described herein. Also described herein are DMT succinate salt, DMT malate salt, DMT sulfate salt and DMT phosphate salt.

According to one aspect, the present disclosure provides DMT fumarate Form A.

According to one aspect, the present disclosure provides DMT succinate Form A.

According to one aspect, the present disclosure provides DMT malate Form A.

According to one aspect, the present disclosure provides DMT oxalate Form A.

According to one aspect, the present disclosure provides DMT sulfate Form A.

According to one aspect, the present disclosure provides DMT succinate salt.

According to one aspect, the present disclosure provides DMT malate salt.

According to one aspect, the present disclosure provides DMT sulfate salt.

According to one aspect, the present disclosure provides DMT phosphate salt.

DETAILED DESCRIPTION OF EMBODIMENTS

In one aspect, the present disclosure is directed succinate, malate, sulfate or phosphate salts of DMT.

In one aspect, the present disclosure is directed to DMT succinate salt.

Also included in the present disclosure are any solvates, for example hydrates, complexes and polymorphic forms of the salts of DMT described herein.

The salts of DMT may exist in crystalline or non-crystalline form, or as a mixture thereof. For salts of DMT that are in crystalline form, the skilled artisan will appreciate that pharmaceutically acceptable solvates may be formed wherein solvent molecules are incorporated into the crystalline lattice during crystallization. Solvates may involve non-aqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates". Hydrates include stoichiometric hydrates as well as compositions containing variable amounts of water. As the skilled person will appreciate, the amount of water may depend upon the conditions, for example humidity. For example, as humidity decreases the amount of water may decrease and as humidity increases the amount of water may increase. Such variations in the amount of water are included within the scope of the invention.

In one aspect, the present disclosure is directed to DMT fumarate crystalline Form A.

In one embodiment, the present disclosure is directed to DMT fumarate crystalline Form A characterized in that it provides an XRPD pattern comprising peaks (°2θ) at about 10.78, about 15.38, about 15.73, about 15.97, about 16.93, about 18.33, about 19.61, about 19.75, about 20.49, about 23.55, about 23.91 and/or about 24.94.

In another embodiment, the present disclosure is directed to DMT fumarate crystalline Form A characterized in that it provides an XRPD pattern comprising peaks (°2θ) substantially as set out in Table 6.

In another embodiment, the present disclosure is directed to DMT fumarate crystalline Form A characterized in that it provides an XRPD pattern comprising peaks (°2θ) substantially as set out in Table 5.

Figure 1:
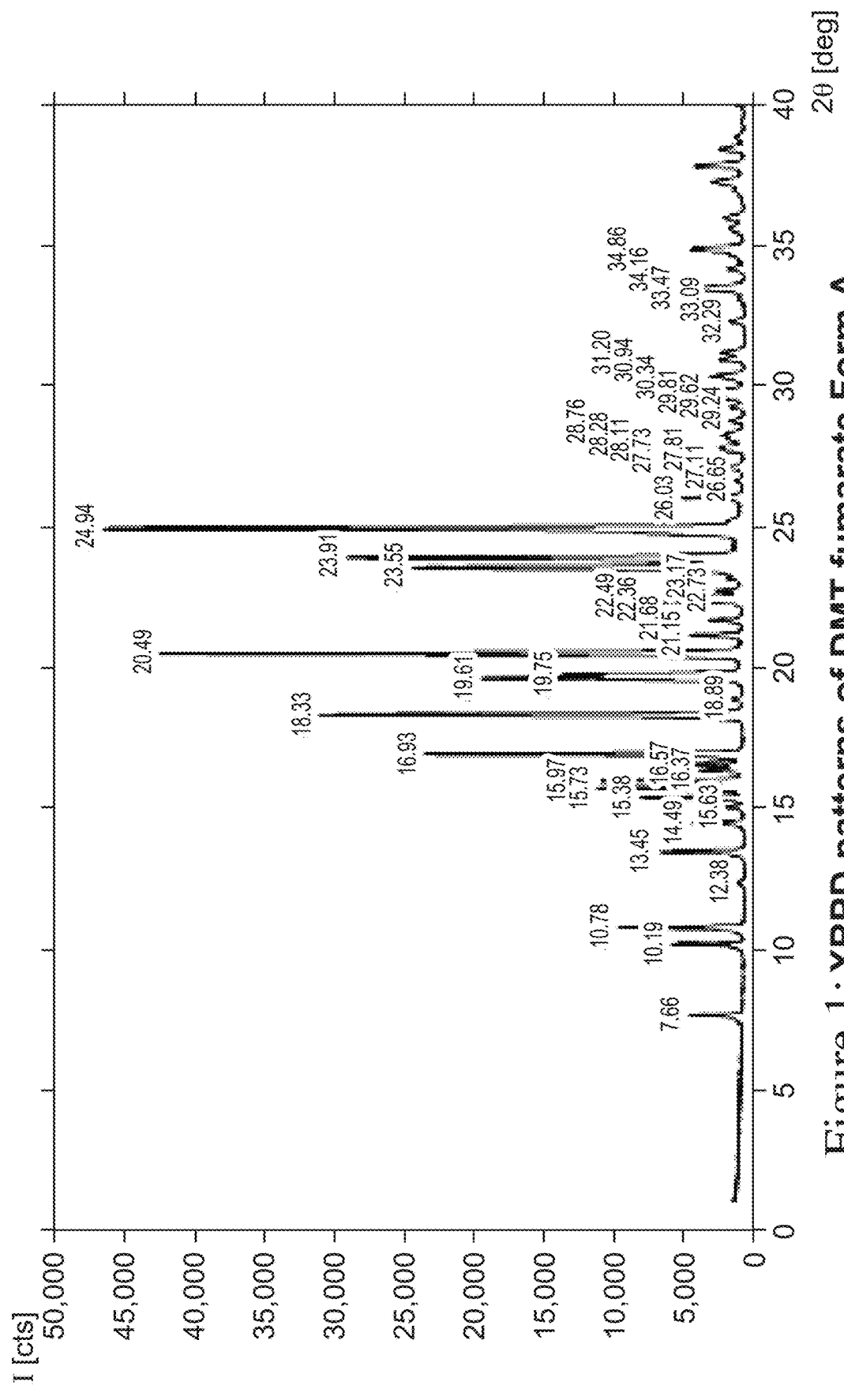
FIG. 1 shows the X-ray powder diffraction (XRPD) for DMT fumarate Form A, including observed peaks.

In a further embodiment, the present disclosure is directed to DMT fumarate crystalline Form A characterized in that it provides an XRPD pattern substantially in accordance with FIG. 1.

Figure 8:
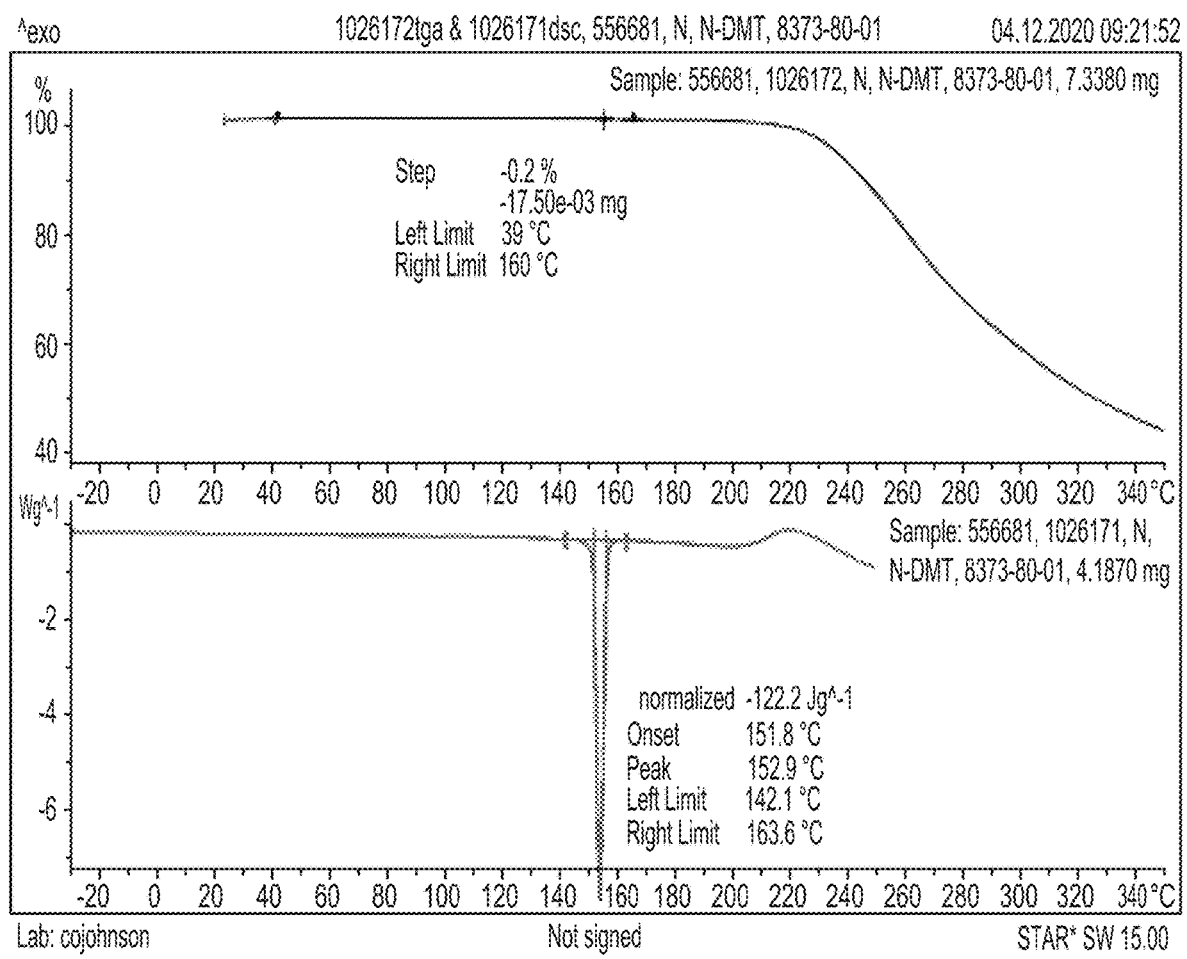
FIG. 8 shows the TGA and DSC thermographs for DMT fumarate Form A.

In one embodiment, the present disclosure is directed to DMT fumarate Form A characterized in that exhibits a TGA thermograph substantially in accordance with FIG. 8.

In one embodiment, the present disclosure is directed to DMT fumarate crystalline Form A characterized in that exhibits a DSC thermograph substantially in accordance with FIG. 8.

Figure 11:
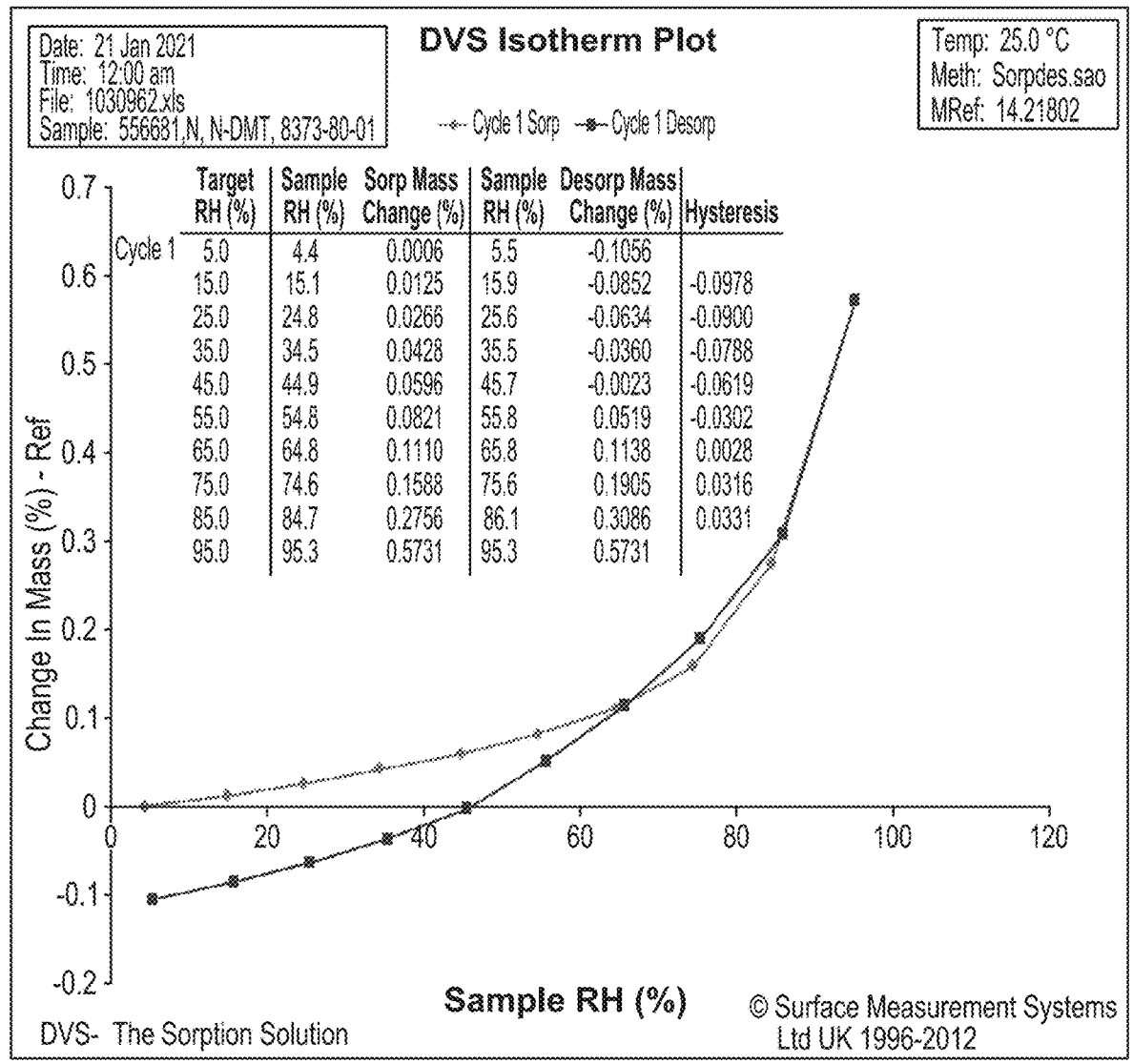
FIG. 11 shows the Dynamic vapor sorption (DVS) isotherm for DMT fumarate Form A.

In one embodiment, the present disclosure is directed to DMT fumarate crystalline Form A characterized in that exhibits a DVS isotherm substantially in accordance with FIG. 11.

In one embodiment, the present disclosure is directed to DMT fumarate crystalline Form A characterized in that it has a melting point of about 151.8° C. when measured under ambient conditions.

In one aspect, the present disclosure is directed to DMT succinate crystalline Form A.

In one embodiment, the present disclosure is directed to DMT succinate crystalline Form A characterized in that it provides an XRPD pattern comprising peaks (°2θ) at about 9.75, about 14.27, about 16.90, about 19.58, about 20.58, about 23.08, about 23.39, about 24.83, about 26.79, and/or about 27.60.

In another embodiment, the present disclosure is directed to DMT succinate crystalline Form A characterized in that it provides an XRPD pattern comprising peaks (°2θ) substantially as set out in Table 8.

In another embodiment, the present disclosure is directed to DMT succinate crystalline Form A characterized in that it provides an XRPD pattern comprising peaks (°2θ) substantially as set out in Table 7.

Figure 2:
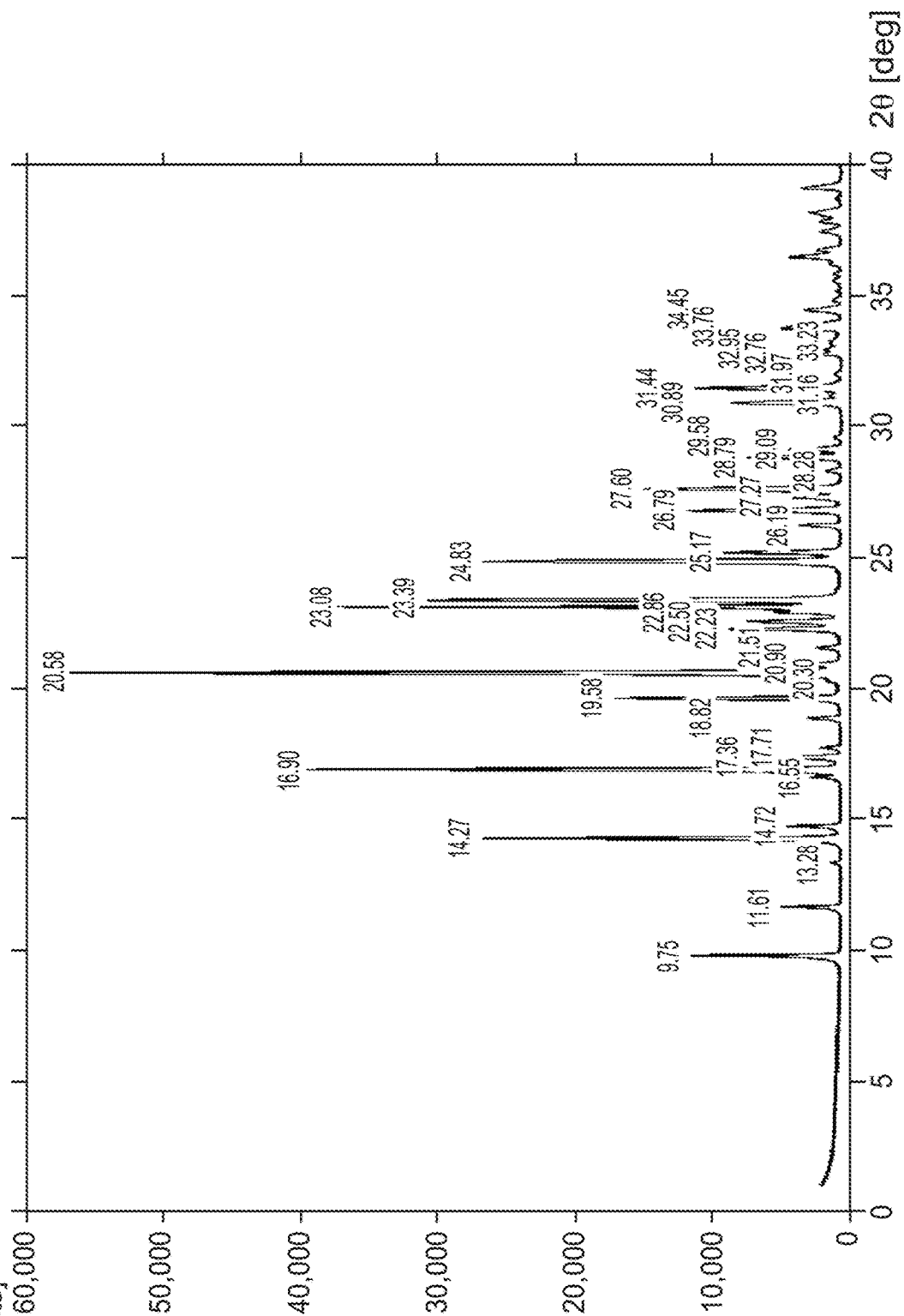
FIG. 2 shows the XRPD for DMT succinate Form A, including observed peaks.

In a further embodiment, the present disclosure is directed to DMT succinate crystalline Form A characterized in that it provides an XRPD pattern substantially in accordance with FIG. 2.

Figure 10:
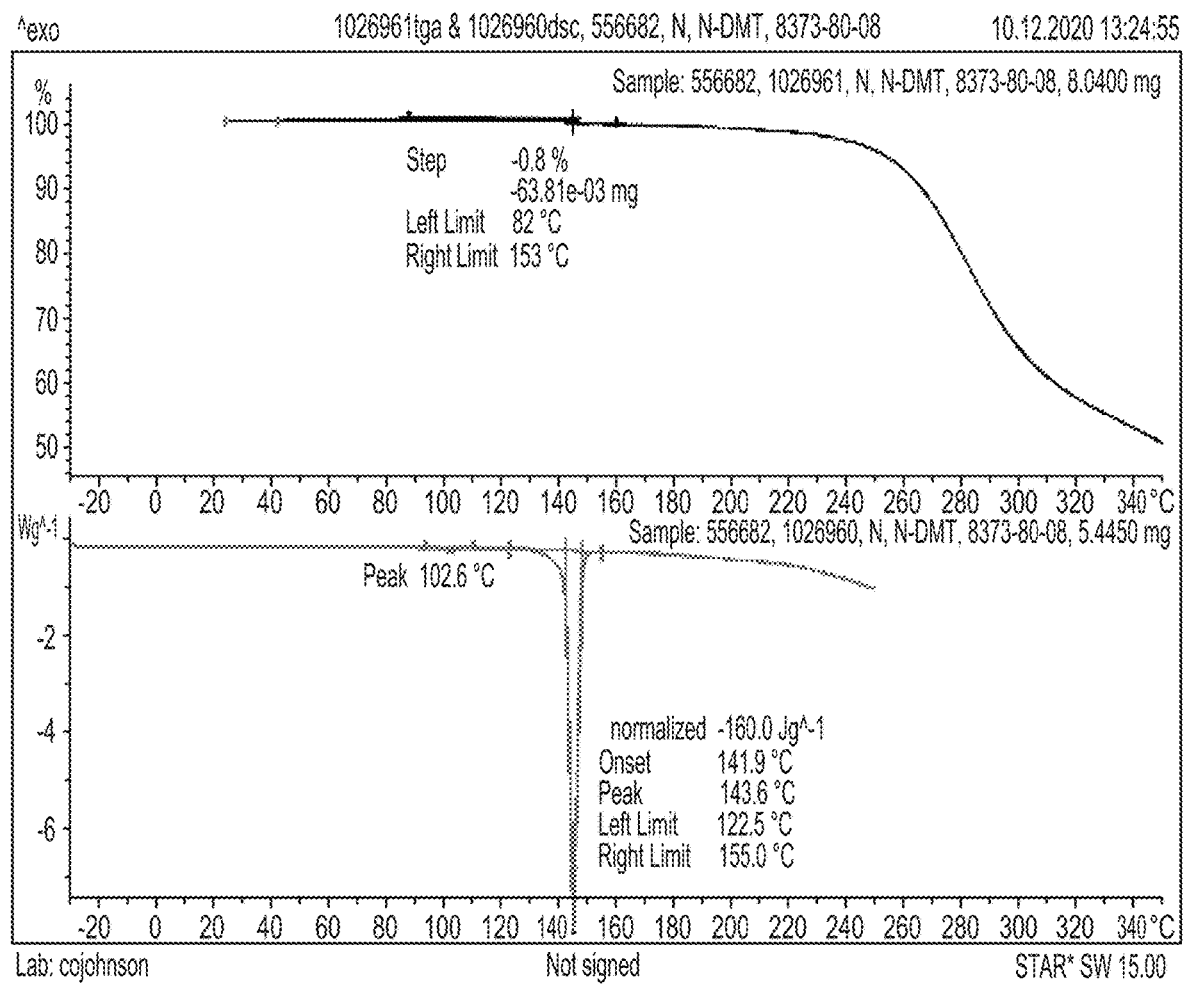
FIG. 10 shows the TGA and DSC thermographs for DMT succinate Form A.

In one embodiment, the present disclosure is directed to DMT succinate crystalline Form A characterized in that exhibits a TGA thermograph substantially in accordance with FIG. 10.

In one embodiment, the present disclosure is directed to DMT succinate crystalline Form A characterized in that exhibits a DSC thermograph substantially in accordance with FIG. 10.

Figure 13:
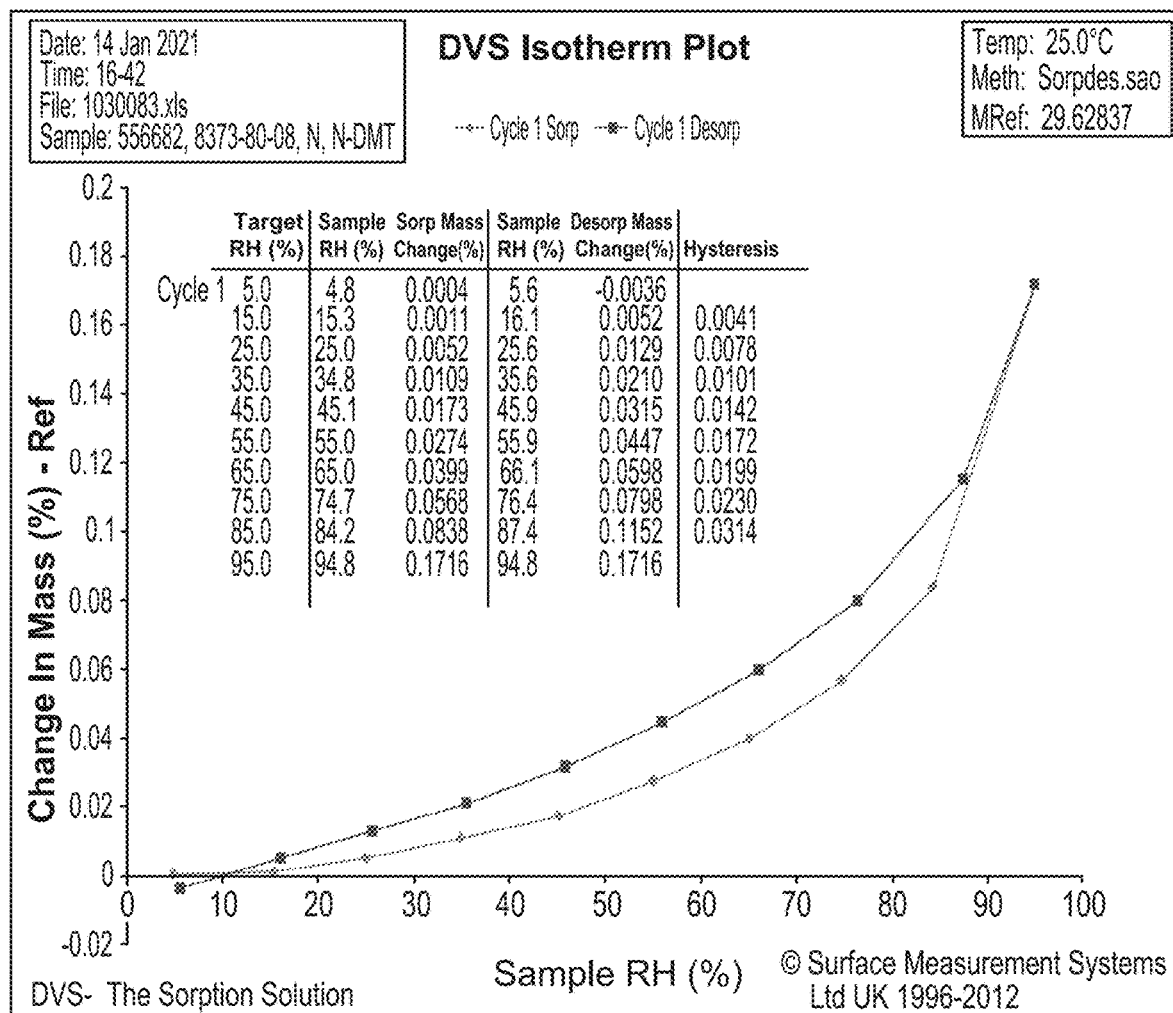
FIG. 13 shows the DVS isotherm for DMT succinate Form A.

In one embodiment, the present disclosure is directed to DMT succinate crystalline Form A characterized in that exhibits a DVS isotherm substantially in accordance with FIG. 13.

Figure 14:
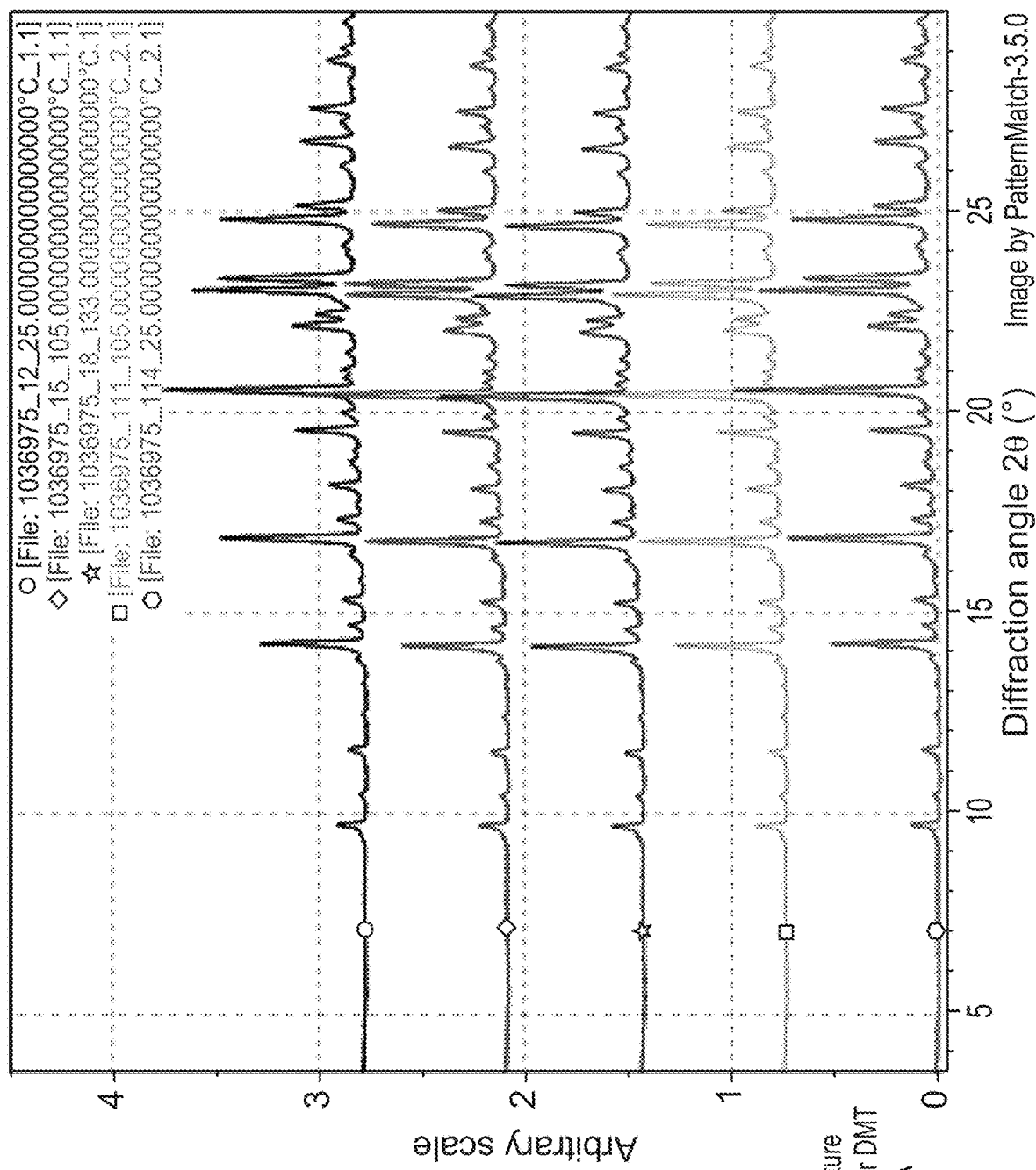
FIG. 14 shows the variable temperature XRPD analysis for DMT succinate Form A.

In a further embodiment, the present disclosure is directed to DMT succinate crystalline Form A characterized in that it provides a variable temperature XRPD pattern substantially in accordance with FIG. 14.

Figure 15:
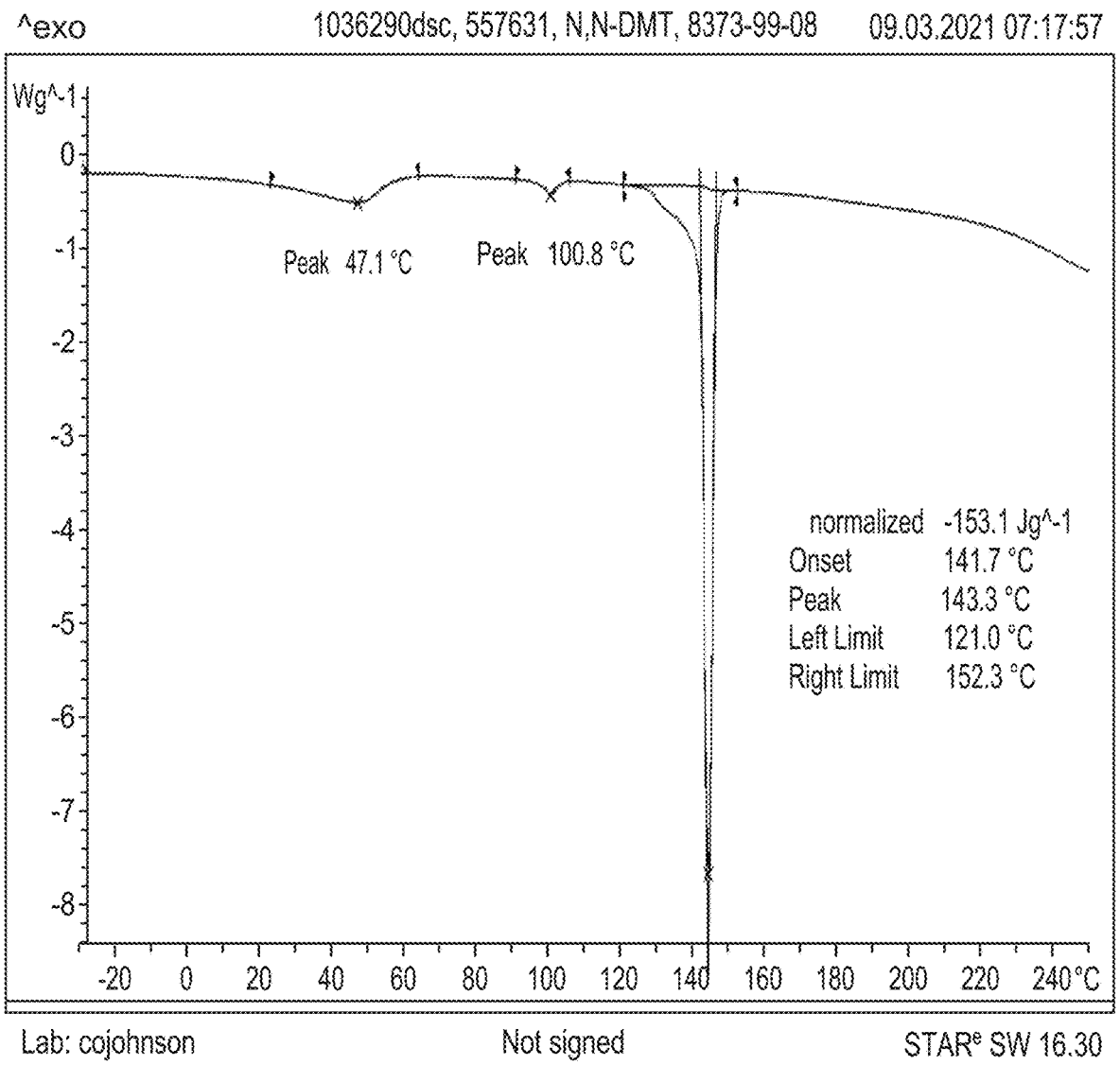
FIG. 15 shows the DSC isotherm for DMT succinate Form A prepared using ethanol as solvent.

In another embodiment, the present disclosure is directed to DMT succinate crystalline Form A characterized in that exhibits a DSC isotherm substantially in accordance with FIG. 15.

Figure 16:
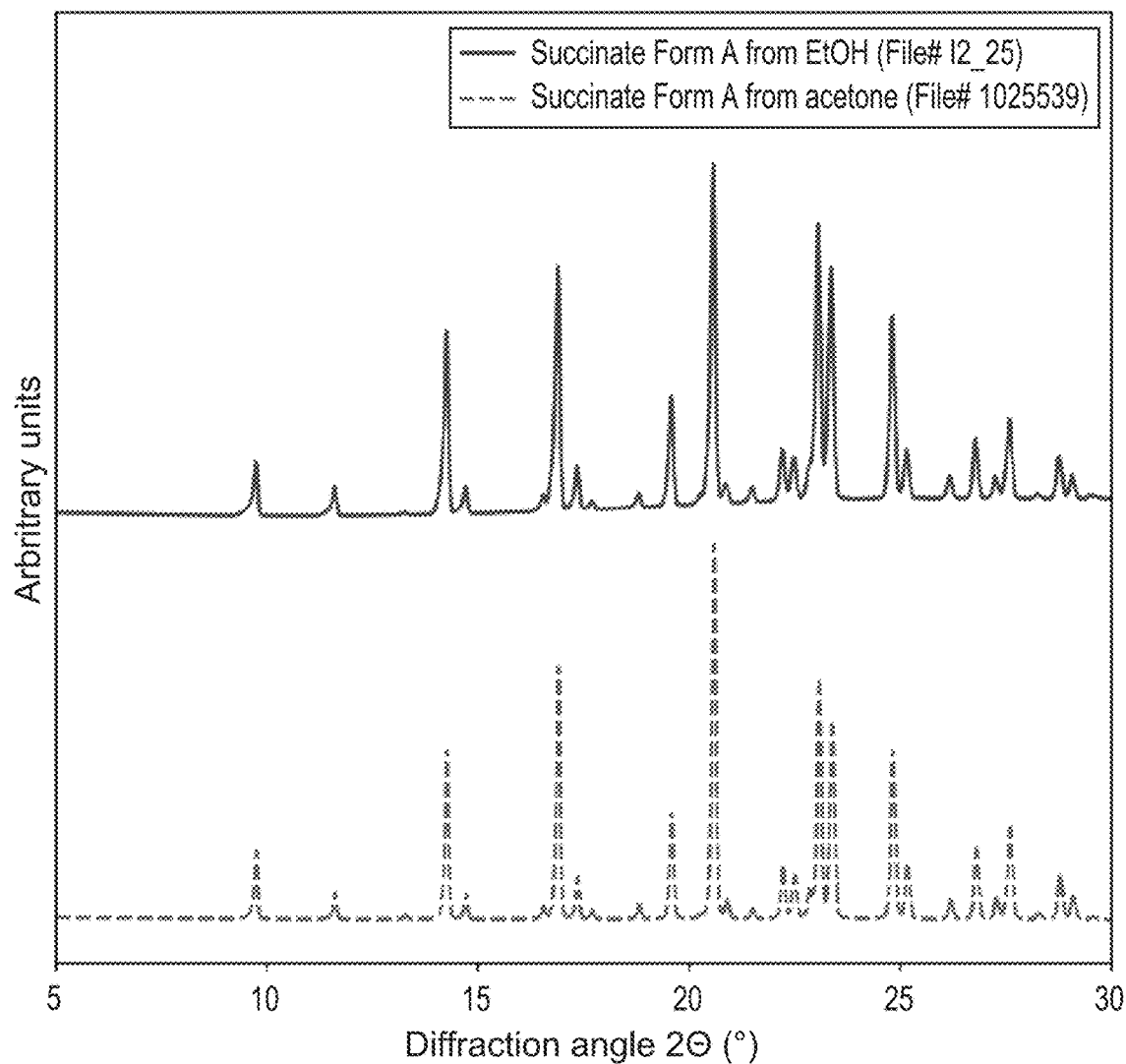
FIG. 16 shows the XRPDs for DMT succinate Form A prepared using ethanol or acetone as solvent.

In a further embodiment, the present disclosure is directed to DMT succinate crystalline Form A characterized in that it provides an XRPD pattern substantially in accordance with FIG. 16.

Figure 17:
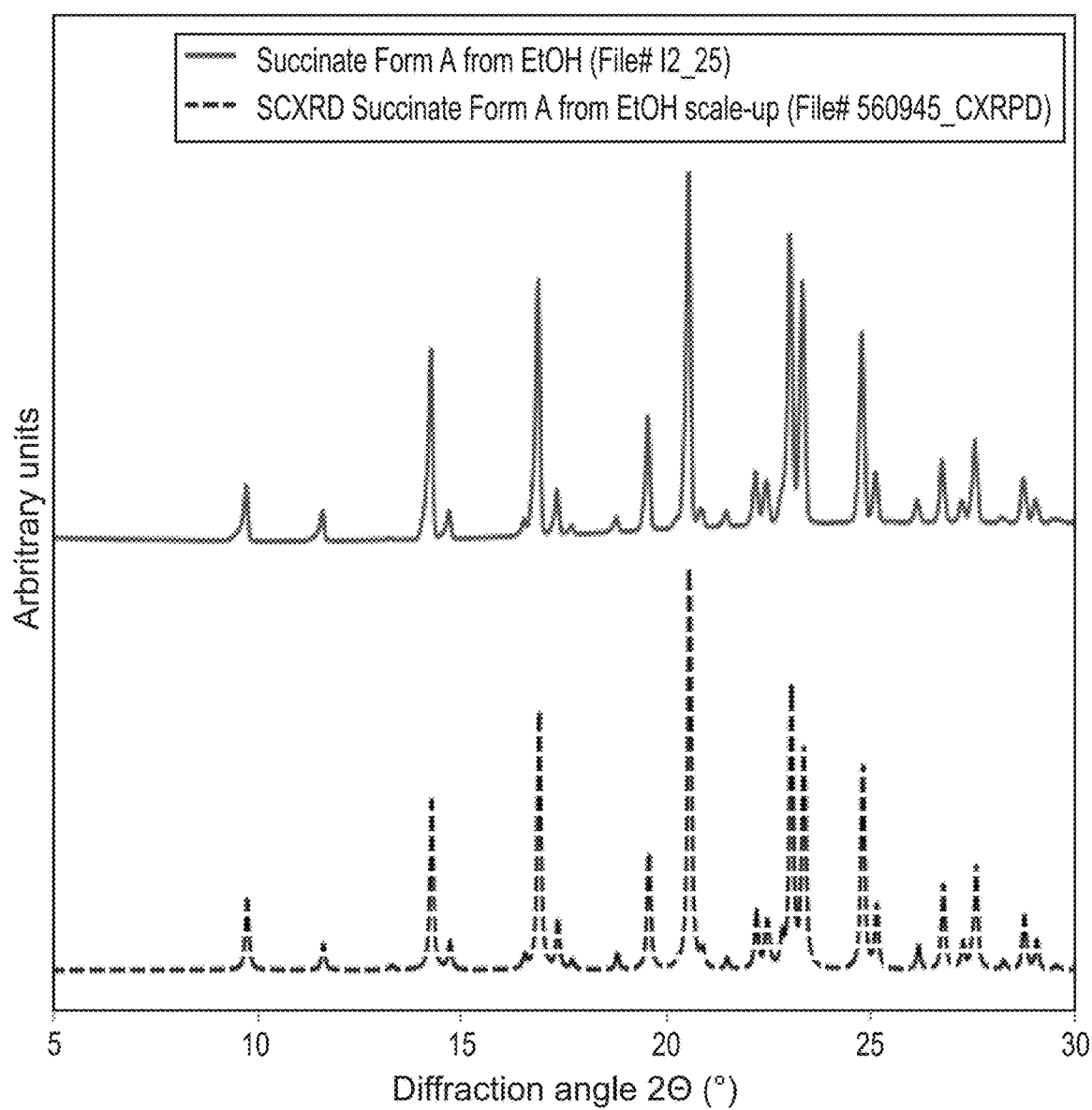
FIG. 17 shows the X-ray diffractions for DMT succinate Form A prepared at milligram scale (XRPD data) or gram scale (Single crystal X-ray diffraction; SCXRD).

In a further embodiment, the present disclosure is directed to DMT succinate crystalline Form A characterized in that it provides an XRPD pattern substantially in accordance with FIG. 17.

In a further embodiment, the present disclosure is directed to DMT succinate crystalline Form A characterized in that it provides an SCXRD pattern substantially in accordance with FIG. 17.

Figure 18:
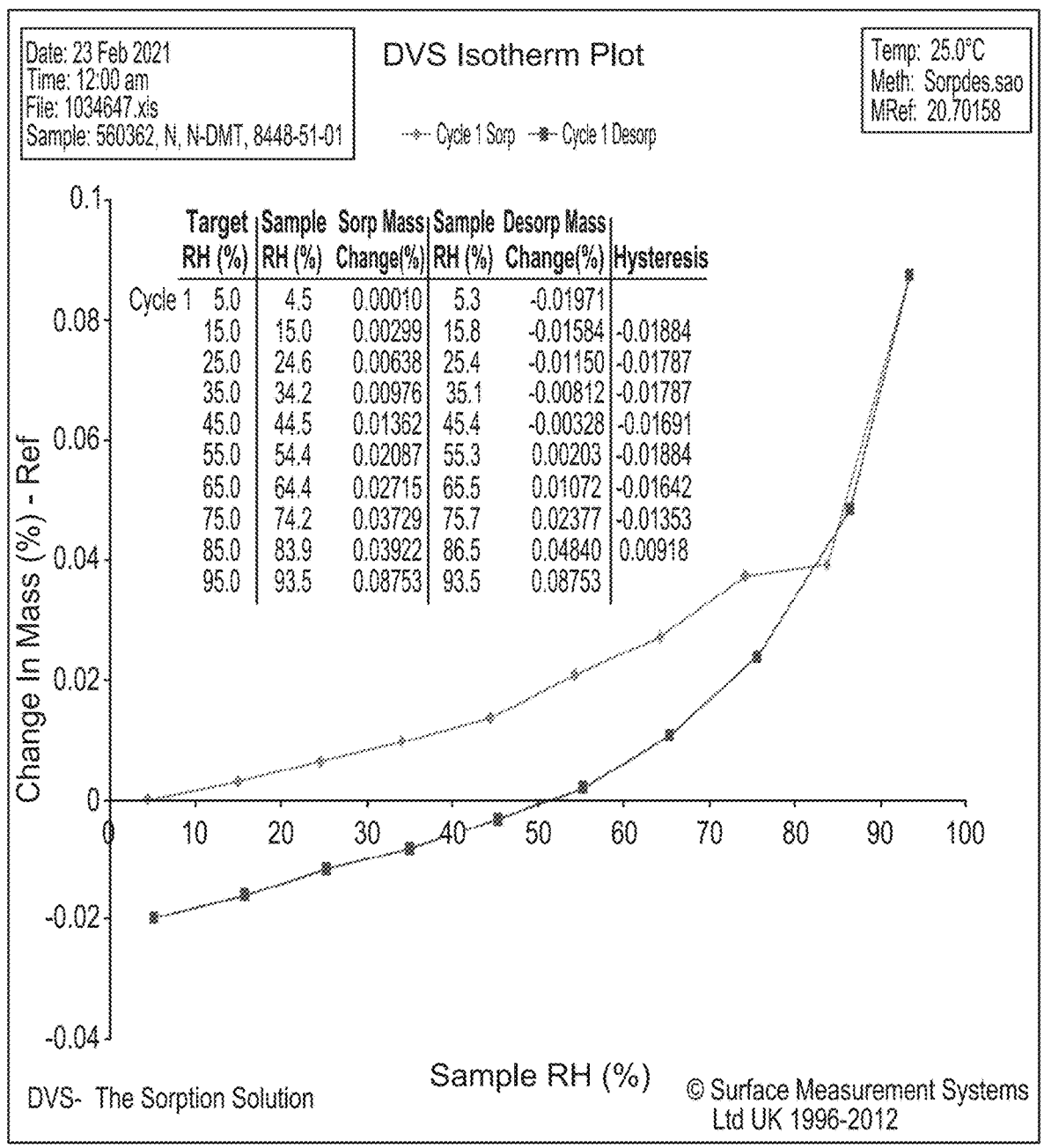
FIG. 18 shows the DVS isotherm for DMT succinate Form A from scale up batch.

In another embodiment, the present disclosure is directed to DMT succinate crystalline Form A characterized in that exhibits a DVS isotherm substantially in accordance with FIG. 18.

Figure 19:
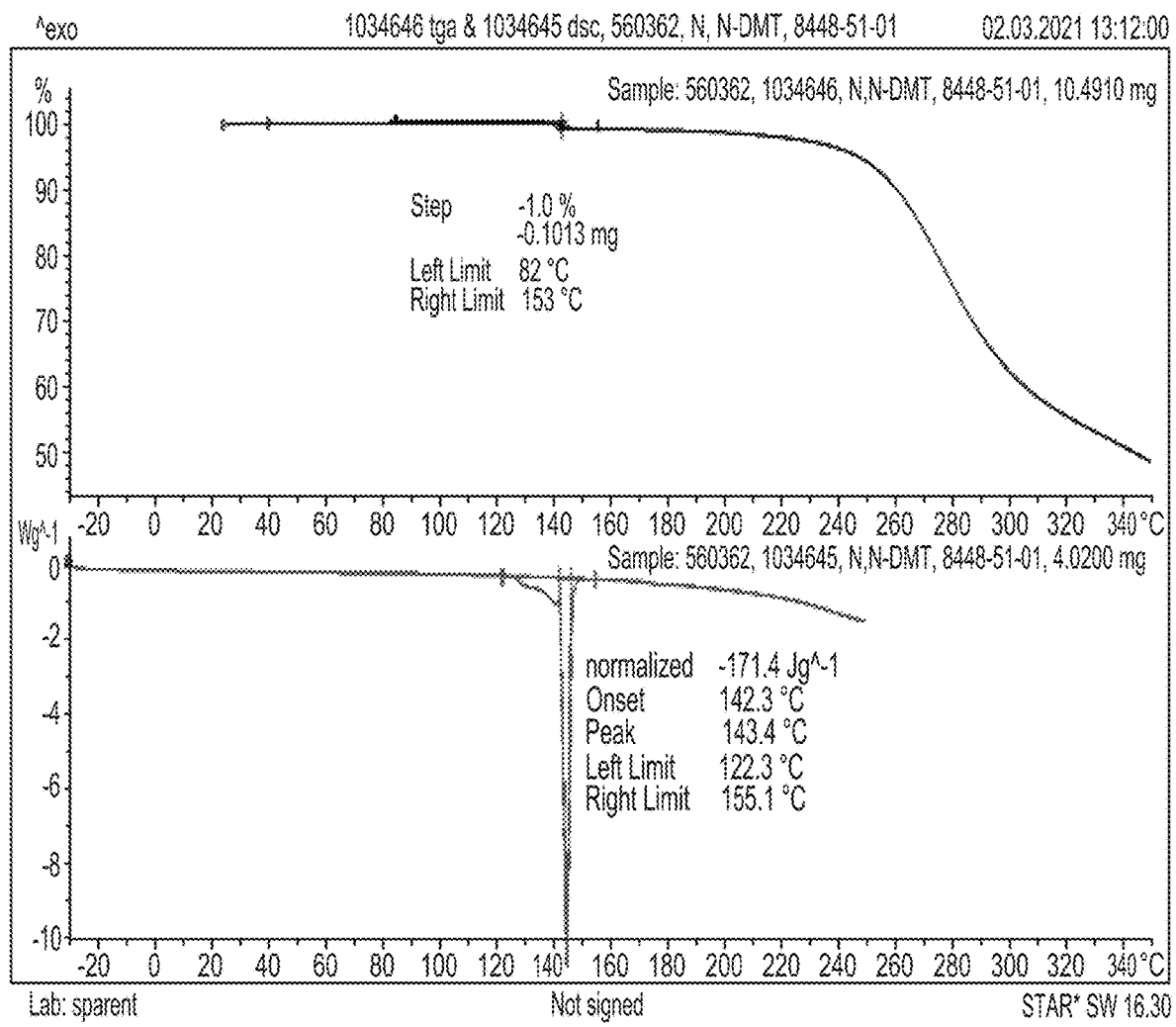
FIG. 19 shows the TGA and DSC thermographs for DMT succinate Form A from scale up batch.

In one embodiment, the present disclosure is directed to DMT succinate crystalline Form A characterized in that exhibits a TGA thermograph substantially in accordance with FIG. 19.

In one embodiment, the present disclosure is directed to DMT succinate crystalline Form A characterized in that exhibits a DSC thermograph substantially in accordance with FIG. 19.

In one embodiment, the present disclosure is directed to DMT succinate crystalline Form A characterized in that it has a melting point of about 141.9° C. when measured under ambient conditions.

In one aspect, the present disclosure is directed to DMT malate crystalline Form A.

In one embodiment, the present disclosure is directed to DMT malate crystalline Form A characterized in that it provides an XRPD pattern comprising peaks (°2θ) at about 9.92, about 13.96, about 16.55, about 19.71, about 20.16, about 22.07, about 22.23, about 22.79, about 23.82, about 25.06 and/or about 29.87.

In another embodiment, the present disclosure is directed to DMT malate crystalline Form A characterized in that it provides an XRPD pattern comprising peaks (°2θ) substantially as set out in Table 10.

In another embodiment, the present disclosure is directed to DMT malate crystalline Form A characterized in that it provides an XRPD pattern comprising peaks (°2θ) substantially as set out in Table 9.

Figure 3:
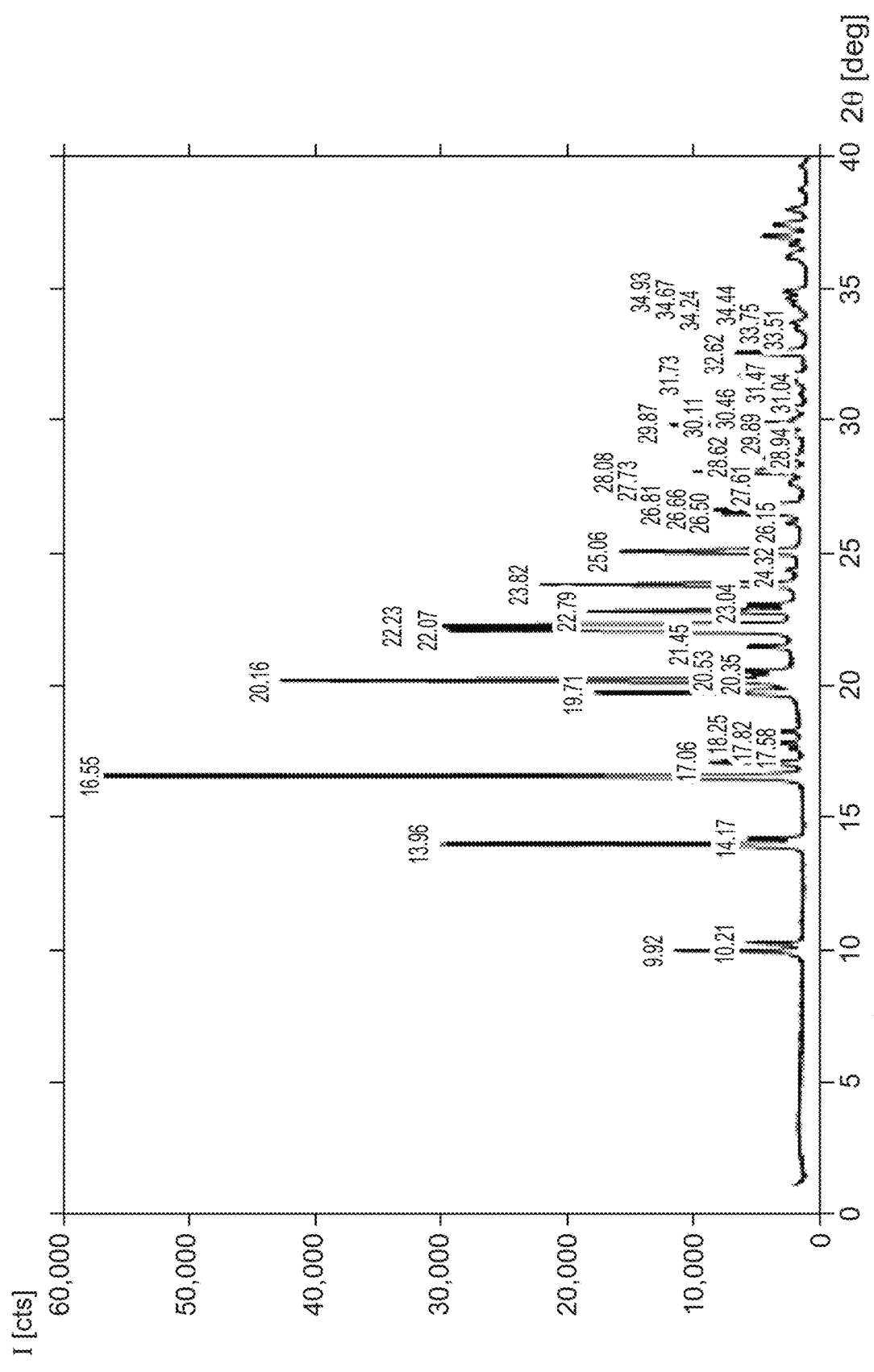
FIG. 3 shows the XRPD for DMT malate Form A, including observed peaks.

In a further embodiment, the present disclosure is directed to DMT malate crystalline Form A characterized in that it provides an XRPD pattern substantially in accordance with FIG. 3.

Figure 9:
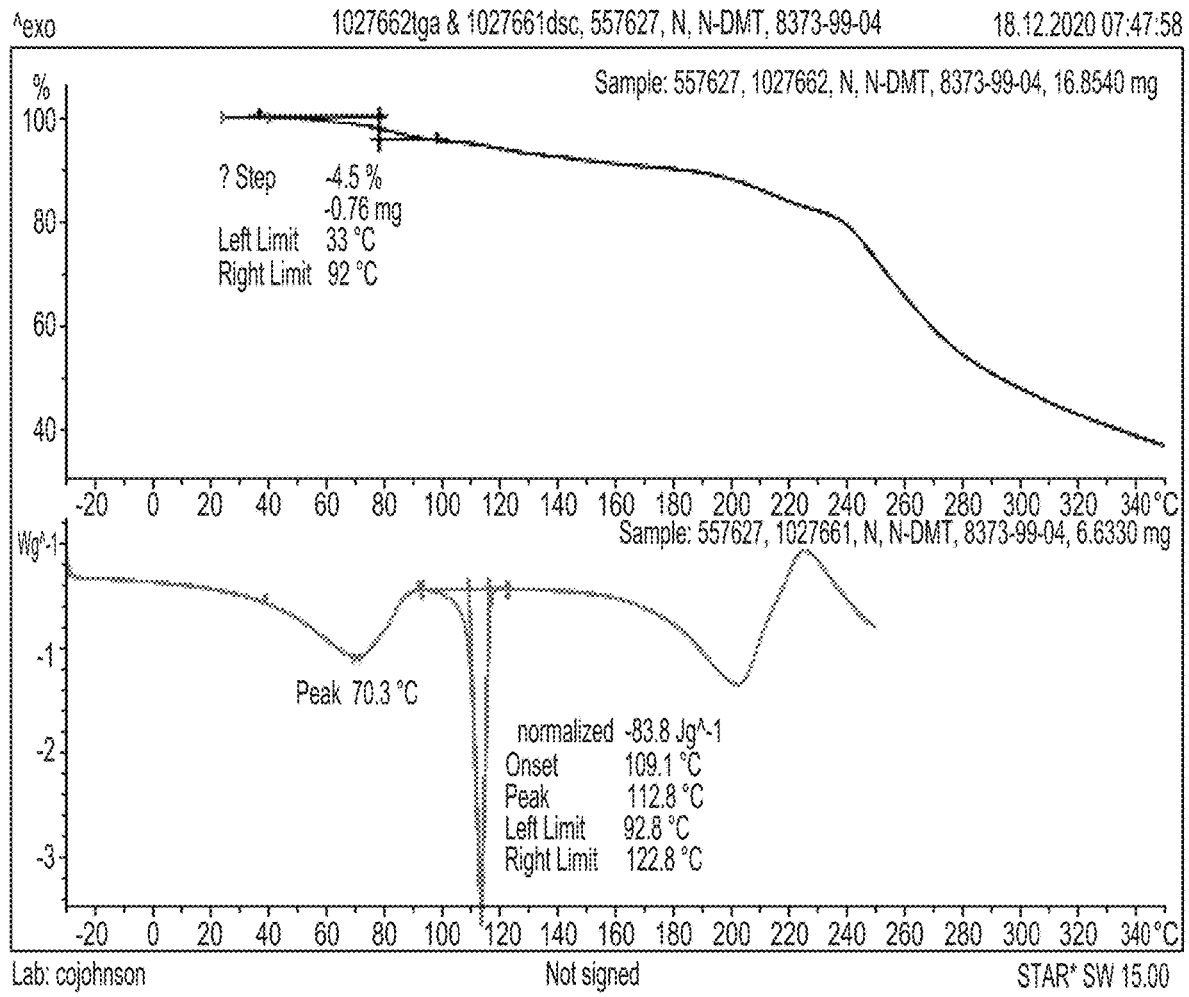
FIG. 9 shows the TGA and DSC thermographs for DMT malate Form A.

In one embodiment, the present disclosure is directed to DMT malate crystalline Form A characterized in that exhibits a TGA thermograph substantially in accordance with FIG. 9.

In one embodiment, the present disclosure is directed to DMT malate crystalline Form A characterized in that exhibits a DSC thermograph substantially in accordance with FIG. 9.

Figure 12:
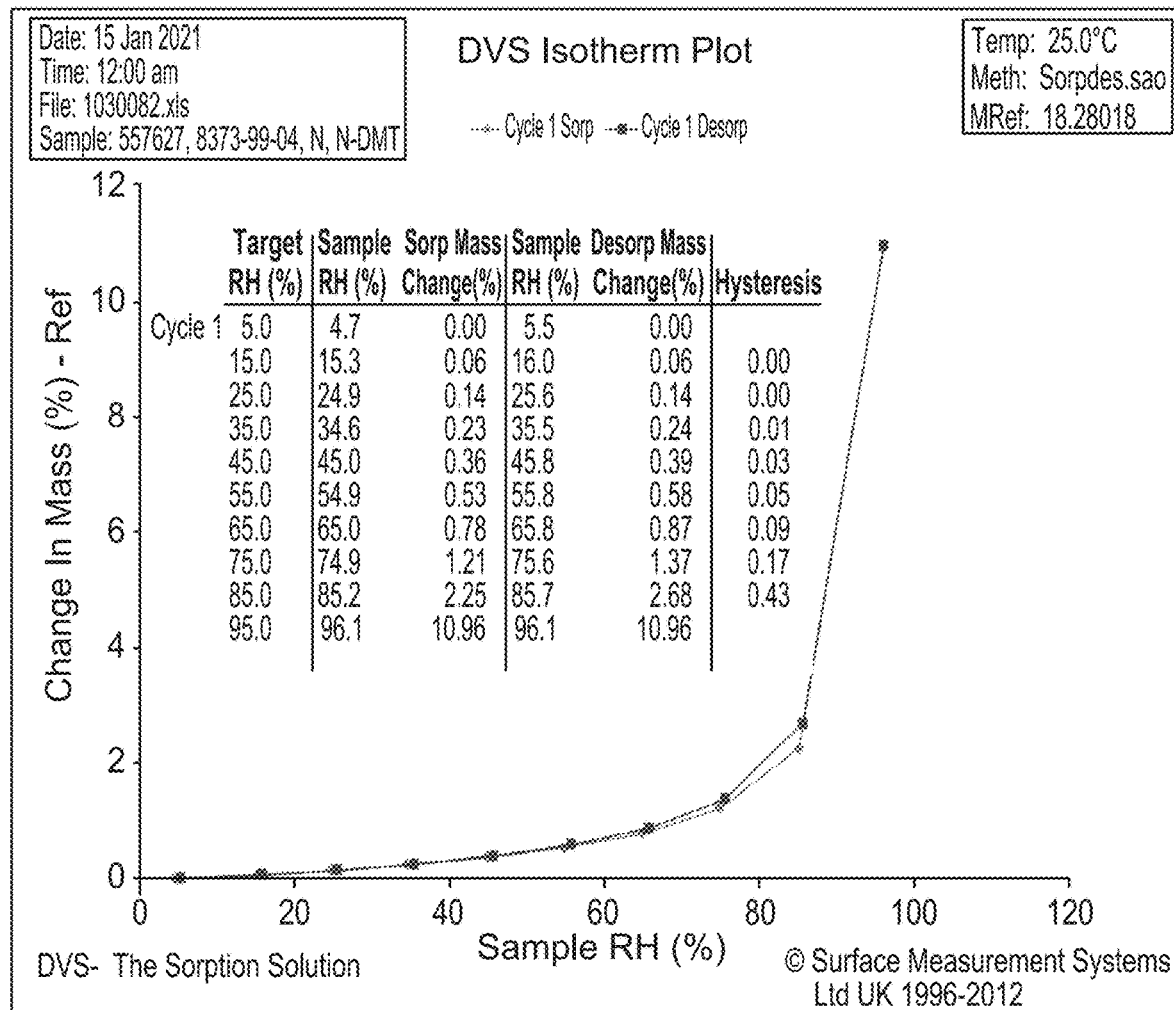
FIG. 12 shows the DVS isotherm for DMT malate Form A.

In one embodiment, the present disclosure is directed to DMT malate crystalline Form A characterized in that exhibits a DVS isotherm substantially in accordance with FIG. 12.

In one embodiment, the present disclosure is directed to DMT malate crystalline Form A characterized in that it has a melting point of about 109.1° C. when measured under ambient conditions.

In one aspect, the present disclosure is directed to DMT sulfate crystalline Form A.

In one embodiment, the present disclosure is directed to DMT sulfate crystalline Form A characterized in that it provides an XRPD pattern comprising peaks (°2θ) at about 11.05, about 15.32, about 15.89, about 16.24, about 19.71, about 19.88, about 22.22, about 23.54, about 23.92, about 24.40, about 25.03 and/or about 25.47.

In another embodiment, the present disclosure is directed to DMT sulfate crystalline Form A characterized in that it provides an XRPD pattern comprising peaks (°2θ) substantially as set out in Table 12.

In another embodiment, the present disclosure is directed to DMT sulfate crystalline Form A characterized in that it provides an XRPD pattern comprising peaks (°2θ) substantially as set out in Table 11.

Figure 4:
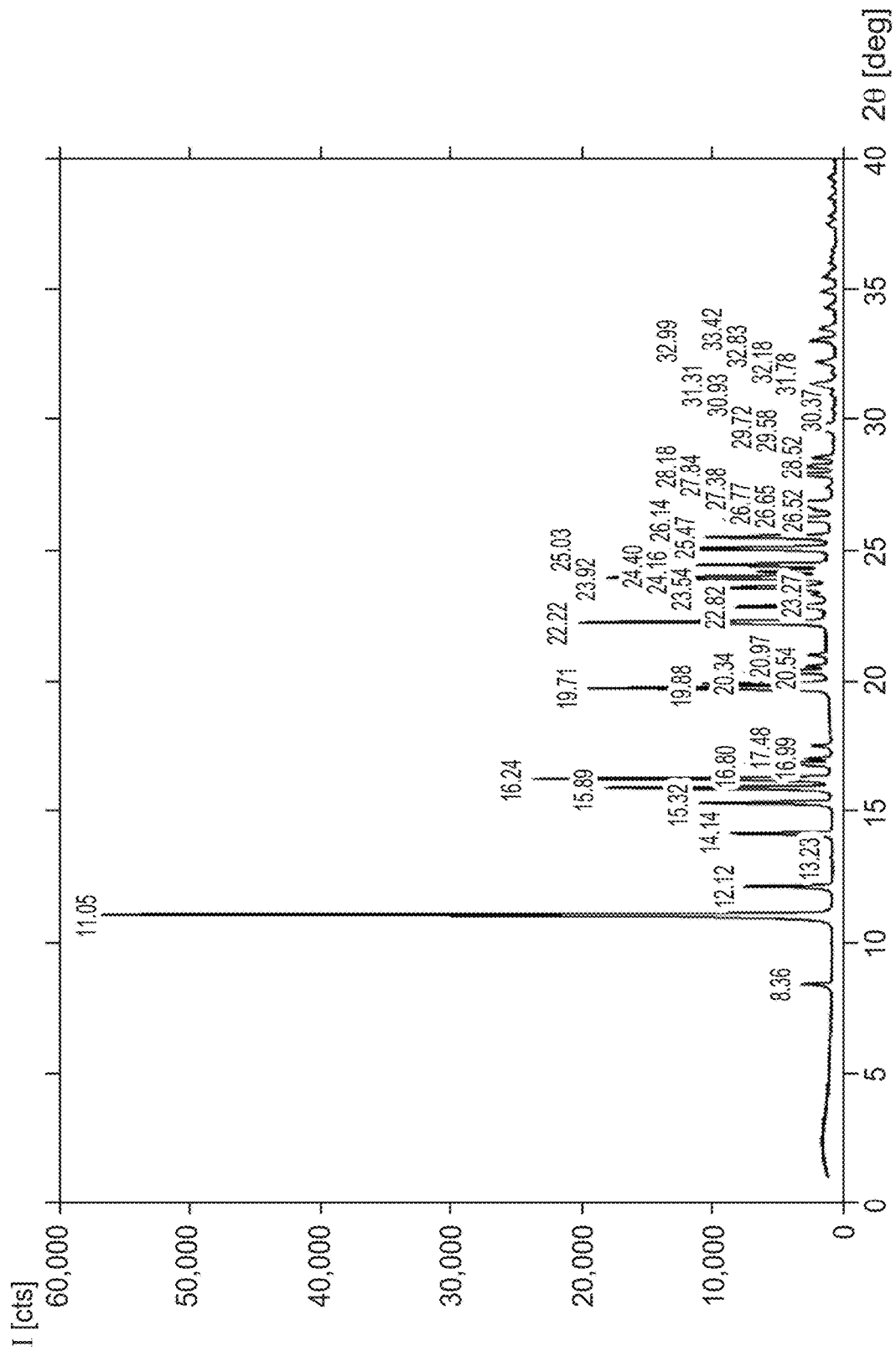
FIG. 4 shows the XRPD for DMT sulfate Form A, including observed peaks.

In a further embodiment, the present disclosure is directed to DMT sulfate crystalline Form A characterized in that it provides an XRPD pattern substantially in accordance with FIG. 4.

Figure 6:
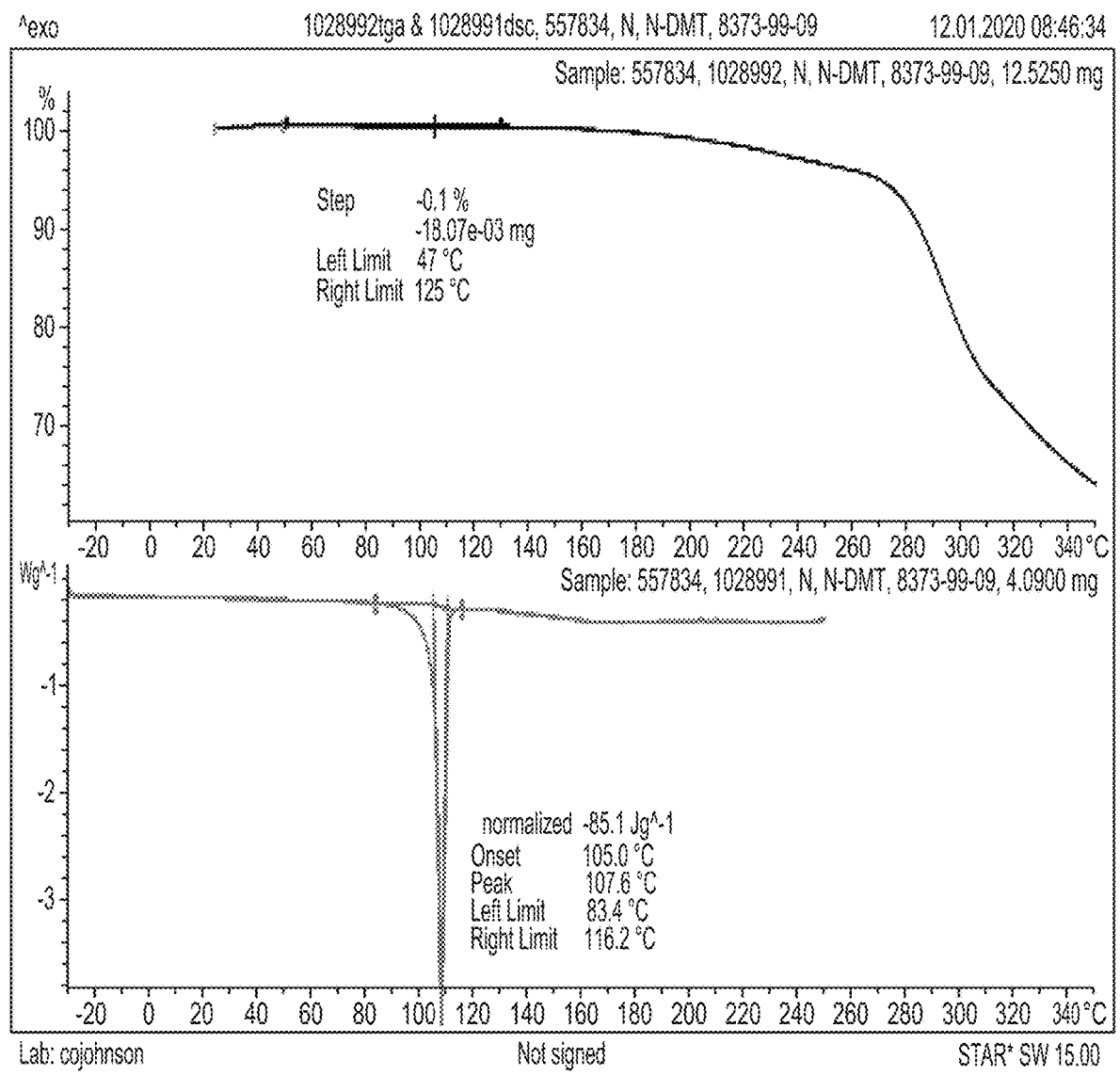
FIG. 6 shows the Thermogravimetric analysis (TGA) and Differential scanning calorimetry (DSC) thermographs for DMT sulfate Form A.

In one embodiment, the present disclosure is directed to DMT sulfate crystalline Form A characterized in that exhibits a TGA thermograph substantially in accordance with FIG. 6.

In one embodiment, the present disclosure is directed to DMT sulfate crystalline Form A characterized in that exhibits a DSC thermograph substantially in accordance with FIG. 6.

In one embodiment, the present disclosure is directed to DMT sulfate crystalline Form A characterized in that it has a melting point of about 105.2° C. when measured under ambient conditions.

In one aspect, the present disclosure is directed to DMT oxalate crystalline Form A.

In one embodiment, the present disclosure is directed to DMT oxalate crystalline Form A characterized in that it provides an XRPD pattern comprising peaks (°2θ) at about 5.86, about 14.63, about 17.60, about 19.26, about 20.32, about 22.03, about 23.57, about 24.34, about 25.78, and/or about 27.51.

In another embodiment, the present disclosure is directed to DMT oxalate crystalline Form A characterized in that it provides an XRPD pattern comprising peaks (°2θ) substantially as set out in Table 14.

In another embodiment, the present disclosure is directed to DMT oxalate crystalline Form A characterized in that it provides an XRPD pattern comprising peaks (°2θ) substantially as set out in Table 13.

Figure 5:
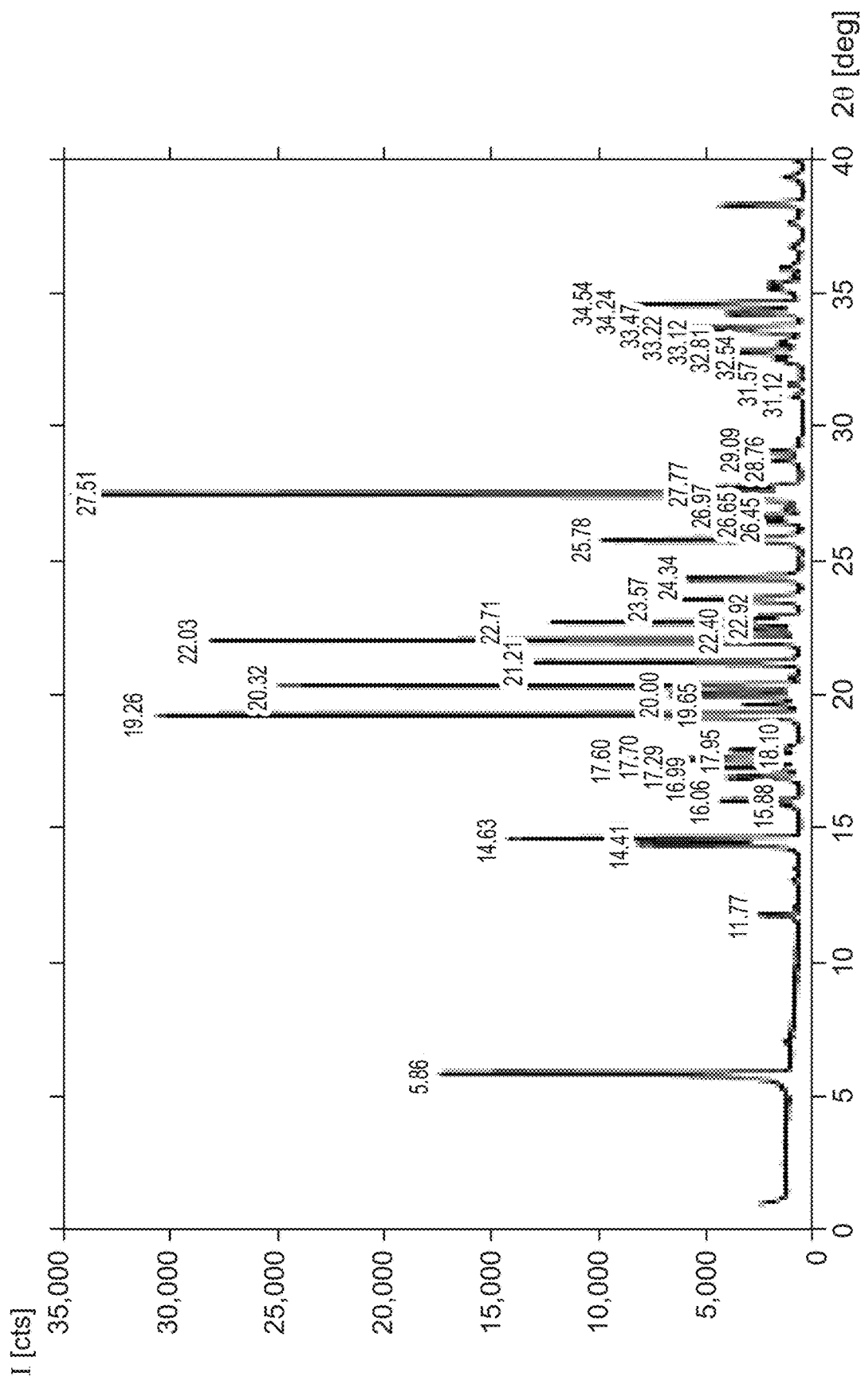
FIG. 5 shows the XRPD for DMT oxalate Form A, including observed peaks.

In a further embodiment, the present disclosure is directed to DMT oxalate crystalline Form A characterized in that it provides an XRPD pattern substantially in accordance with FIG. 5.

Figure 7:
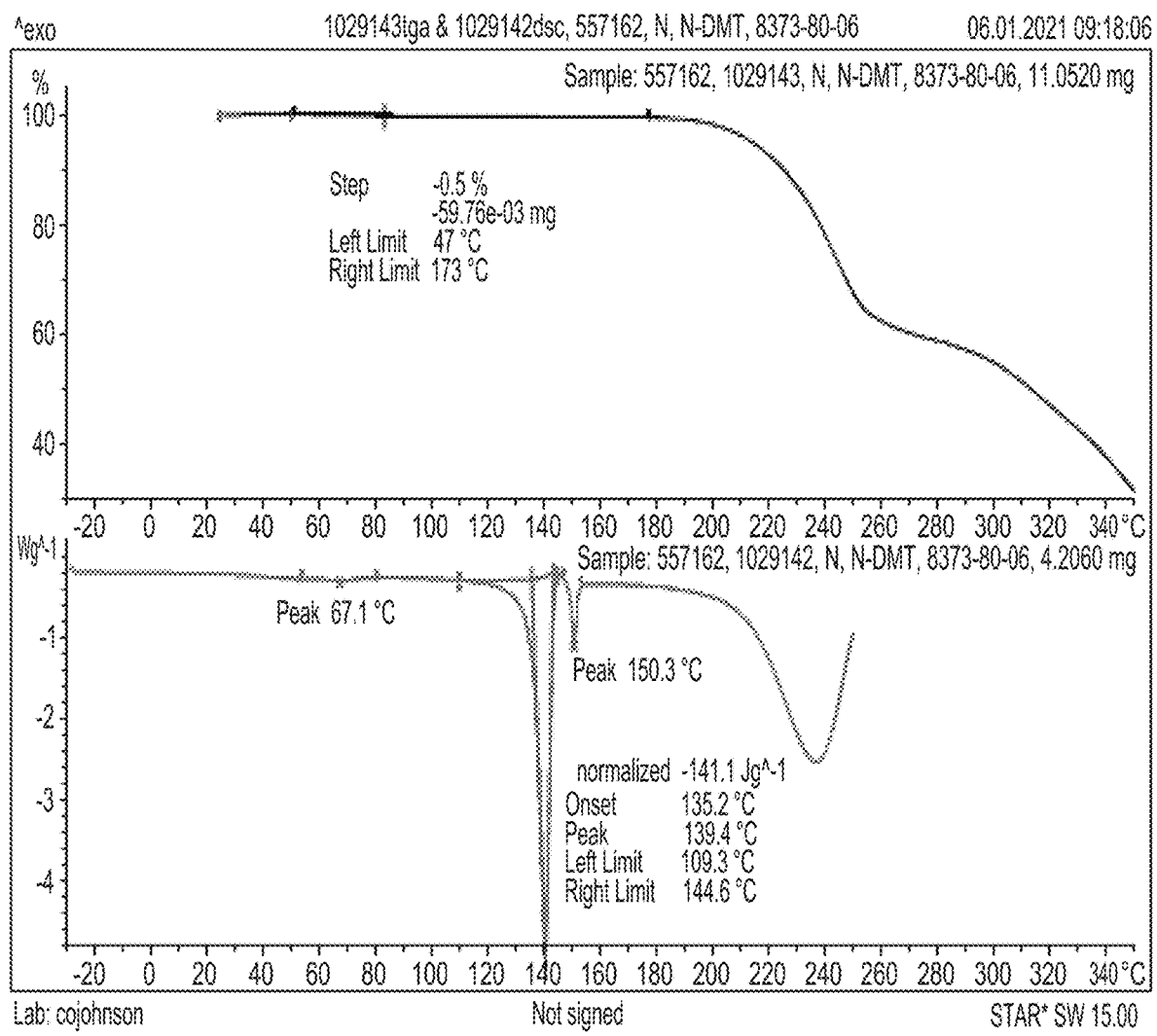
FIG. 7 shows the TGA and DSC thermographs for DMT oxalate Form A.

In one embodiment, the present disclosure is directed to DMT oxalate crystalline Form A characterized in that exhibits a TGA thermograph substantially in accordance with FIG. 7.

In one embodiment, the present disclosure is directed to DMT oxalate crystalline Form A characterized in that exhibits a DSC thermograph substantially in accordance with FIG. 7.

In one embodiment, the present disclosure is directed to DMT oxalate crystalline Form A characterized in that it has a melting point of about 135.2° C. when measured under ambient conditions.

When it is indicated herein that there is a peak in an XRPD pattern at a given value, it is typically meant that the peak is within ±0.2 of the value quoted.

The present disclosure encompasses the salt forms of DMT and the salts of DMT isolated in pure form or when admixed with other materials, for example other salt forms or solvates of DMT.

Thus, in one aspect of the present disclosure, there is provided DMT succinate crystalline Form A in isolated or pure form. "Isolated" or "pure" form refers to a sample in which DMT succinate crystalline Form A is present in an amount of >75%, particularly >90%, more particularly >95% and even more particularly >99% relative to other materials which may be present in the sample.

Terms and Definitions

As used herein the symbols and conventions used in these processes, tables, figures and examples are consistent with those used in the contemporary scientific literature, for example, the Journal of the American Chemical Society or the Journal of Biological Chemistry. Unless otherwise noted, all starting materials were obtained from commercial suppliers and used without further purification. Specifically, the following abbreviations may be used in the examples and throughout the specification:

DMT: N, N-dimethyltryptamine
XRPD: X-ray powder diffraction
TGA: Thermogravimetric analysis
DSC: Differential scanning calorimetry
DVS: Dynamic vapor sorption
SCXRD: Single crystal X-ray diffraction
RH: Relative humidity
RT: Room temperature
EtOH: Ethanol
Sorp: Sorption
Desorp: Desorption
ACN: Acetonitrile
DMF: Dimethylformamide
EtOAc: Ethyl acetate
HFIPA: Hexafluoro-2-propanol
IPA: Isopropyl alcohol
MeOH: Methanol NMP: N-Methyl-2-pyrrolidone
TFE: 2,2,2-Trifluoroethanol
PTFE: Polytetrafluoroethylene
VD: Vapor diffusion
VS: Vapor stressing
FE: Fast evaporation
CC: Crash cooling The term "carrier" refers to a diluent, adjuvant, excipient, or vehicle with which the therapeutic is administered and includes, but is not limited to such liquids and powders that are hydrophilic substances, hydrophobic substances and substances that possess both hydrophilic and hydrophobic properties such as emulsifiers.

The term "effective amount" or "therapeutically effective amount" as used herein, refers to the amount of active agent that elicits the biological or medicinal response in a tissue, system, or individual that is being sought by a researcher, healthcare provider or individual.

The term "neurological disease or condition" as used herein, means a disease or condition selected from: a neuropsychiatric disorder, such as depression (including severe depression such as treatment-resistant depression, major depressive disorder and persistent depressive disorder), catatonic depression, a depressive disorder due to a medical condition, postpartum depression, premenstrual dysphoric disorder, or seasonal affective disorder, anxiety, anxiety disorder, social anxiety disorder, general anxiety disorder (GAD), avolition disorder, bipolar disorder (including bipolar I disorder and bipolar II disorder), post-traumatic stress disorder, body dysmorphic disorder, abnormalities of mood or emotion, including the above conditions, dysthymia, schizoaffective disorder, schizophrenia and other psychotic disorders, panic disorder, traumatic stress disorders, phobic disorders, and personality disorders with abnormal mood, such as borderline personality disorder, schizoid and schizotypal disorders and suicide ideation, or rumination/unproductive repetitive thoughts negatively impacting one's behavior/mood/ability to focus, obsessive-compulsive disorder, addiction (including substance use disorder such as addiction to nicotine, alcohol, cocaine, opioids, amphetamine, methamphetamine, heroin, morphine, phencyclidine, 3,4-methylenedioxy-methamphetamine, as well as other addictive substances), addictive behavior (including eating, gambling, sex, pornography, videogames, work, exercise, spiritual obsession, self-harm, travel and shopping addiction), eating disorder (including anorexia nervosa, bulimia nervosa and binge eating disorder), and pain (including pain associated with migraine or headache or chronic pain).

As used herein, the term "treatment-resistant depression" or "TRD" means a depressive disorder which does not respond satisfactorily to adequate treatment. TRD is a complex phenomenon influenced by variety in depressive subtypes, psychiatric comorbidity, and coexisting medical illnesses. Although TRD episodes are most commonly associated with major depressive disorder (MDD), they are also seen in the depressed phase of bipolar disorder.

The term "about" when used before a numerical designation, e.g., pH, temperature, amount, or concentration, indicates an approximation which may vary by up to (+) or (−) 5%, unless otherwise specifically defined herein.

The singular form "a", "an" and "the" include plural references unless the context clearly dictates otherwise. For example, the term "a pharmaceutically acceptable carrier" may include a plurality of pharmaceutically acceptable carriers, including mixtures thereof.

The term "and/or" is intended to mean either or both of two components of the invention.

The term "subject," "individual" and "patient" are used interchangeably herein, and refers to a human.

The term "device," as used herein, refers to an apparatus or system capable of delivering a drug to a patient in need thereof.

The term "in need of treatment" and the term "in need thereof" when referring to treatment are used interchangeably and refer to a judgment made by a caregiver (e.g. physician, nurse, nurse practitioner) that a patient will benefit from treatment.

The terms "treat" and "treatment" refer herein to therapeutic treatment, including prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition. "Treatment" can also mean prolonging survival as compared to expected survival if not receiving treatment. Those in need of treatment include those already with the disease or condition as well as those prone to having the disease or condition or those in which the disease or condition is to be prevented. "Treatment" can, when concerning depression, also include reducing at least one sign or symptom of depression. Examples of a sign or symptom of depression include depressed mood, diminished interest in activities, weight loss or gain, decrease or increase in appetite, insomnia or hypersomnia, psychomotor agitation or retardation, fatigue or loss of energy, feelings of worthlessness or excessive or inappropriate guilt, diminished ability to concentrate or indecisiveness, or suicidal ideation or behavior.

The term "nasal delivery", "intranasal delivery", "nasal administration" or "intranasal administration" refers to a route of administration wherein the pharmaceutical dosage form is taken to, or through, the nose (e.g., nasal cavity). Similarly, a "nasal delivery device" or an "intranasal delivery device" is intended to mean an apparatus that administers a drug into the nasal cavity. Non-limiting examples of intranasal administration include introduction of a solution or suspension in the form of a nasal spray or drops (direct instillation) or intranasal application of a gel, emulsion or ointment.

The term "buccal delivery" or "buccal administration" refers to a route of administration in which the pharmaceutical dosage form is applied between the patient's cheek and gum (i.e. the buccal cavity).

The term "sublingual delivery" refers to a route of administration in which the pharmaceutical dosage form is applied under the patient's tongue.

Salt and Salt Form Preparation

The present disclosure is also directed to processes for preparing the salts and salt forms of DMT.

In a further aspect, the disclosure provides a process for preparing a salt or crystalline sa Form A of DMT, which comprises contacting DMT free base with a suitable acid such as fumarate acid, succinic acid, L-(−)malic acid, sulfuric acid, oxalic acid, or phosphoric acid in the presence a suitable solvent such as acetone or ethanol which forms a slurry which is preferably stirred for one to five or more days, and collecting the solids formed, e.g. by filtration, such as by using a Swinnex positive pressure filter assembly using a 0.2-μm nylon filter. The process may conveniently be performed between about −20° C. to around room temperature.

The disclosure further provides for recrystallizing the Form A DMT salts from a suitable solvent including ACN, DMF, EtOAc, HFIPA, IPA, MeOH, NMP and TFE at temperatures between −20° C. to 50° C.

DMT free base may be prepared according to known procedures or purchased from commercial suppliers.

Pharmaceutical Compositions and Delivery

In one aspect, the present disclosure provides a pharmaceutical composition comprising a DMT salt selected from DMT succinate, DMT malate, DMT sulfate and DMT phosphate (e.g. DMT succinate) together with one or more carriers and/or excipients.

In one aspect, the present disclosure provides a pharmaceutical composition comprising a DMT salt form selected from DMT fumarate Form A, DMT succinate Form A, DMT malate Form A, DMT oxalate Form A and DMT sulfate Form A (e.g. DMT succinate Form A) together with one or more carriers and/or excipients.

Pharmaceutical compositions comprising DMT salts and salt forms (e.g. DMT succinate crystalline Form A) may be compressed into solid dosage units, such as tablets, or be processed into capsules or suppositories. By means of pharmaceutically suitable liquids, the compounds can also be prepared in the form of a solution, suspension, emulsion, or as a spray. For making dosage units, including tablets, the use of conventional additives such as fillers, colorants, polymeric binders and the like is contemplated. In general, any pharmaceutically acceptable additive can be used. Suitable fillers with which the pharmaceutical compositions can be prepared and administered include lactose, starch, cellulose and derivatives thereof, and the like, or mixtures thereof used in suitable amounts.

For parenteral administration, aqueous suspensions, isotonic saline solutions and sterile injectable solutions comprising DMT salts and salt forms (e.g. DMT succinate crystalline Form A) may be used, containing pharmaceutically acceptable dispersing agents and/or wetting agents, such as propylene glycol or butylene glycol.

The present disclosure also provides a pharmaceutical composition as described herein in combination with packaging material suitable for the composition, the packaging material including instructions for the use of the pharmaceutical composition.

Pharmaceutical compositions comprising DMT salts and salt forms (e.g. DMT succinate crystalline Form A) suitable for intranasal administration include compositions wherein the active ingredient is present in a liquid carrier. In various embodiments, the composition may be in the form of an aqueous or non-aqueous solution, suspension, liposomal dispersion, emulsion, microemulsion or sol-gel. The carrier can contain additives such as solubilizing agents, e.g., propylene glycol, surfactants, absorption enhancers such as lecithin (phosphatidylcholine) or cyclodextrin, mucoadhesives and/or preservatives such as parabens. Methods well known in the art for making intranasal formulations may be found, for example, in Remington, 2000. Further, methods for formulating compounds for intranasal administration, including extending the presence of the active agent in the nasal cavity, combining with agents to enhance solubility, and increasing bioavailability, etc. are well known.

Pharmaceutical compositions comprising DMT salts and salt forms (e.g. DMT succinate crystalline Form A) suitable for buccal and sublingual administration include rapidly dissolving tablets, wafers, films, strips or patches, orodispersible tablets, oral gels, medicated lollipops, sprays, drops, and other formulations that are retained on the buccal or sublingual mucosal surface.

Pharmaceutical compositions comprising DMT salts and salt forms (e.g. DMT succinate crystalline Form A) suitable for subcutaneous administration may be provided in unit dosage forms (e.g., in single-dose ampoules), or in vials containing several doses and in which a suitable preservative may be added (see below). The composition may conveniently be in form of a solution, a suspension or an emulsion, or it may be presented as a dry powder to be reconstituted with water or another suitable vehicle before use. Apart from a DMT salt or salt form (e.g. DMT succinate crystalline Form A), the composition may include suitable parenterally acceptable carriers and/or excipients. Furthermore, the composition may include suspending, solubilizing, stabilizing, pH-adjusting agents, and/or dispersing agents.

Pharmaceutical compositions of the present disclosure may include one or more excipients, diluents, binders, lubricants, glidants, disintegrants, desensitizing agents, emulsifiers, mucosal adhesives, solubilizers, suspension agents, viscosity modifiers, ionic tonicity agents, buffers, carriers, surfactants, or mixtures thereof. Pharmaceutical compositions of the present disclosure may also include components such as permeation enhancers, bioadhesive polymers, and means for providing modified release, such as sustained release, of the active ingredient. The compositions can also include one or more pharmaceutically acceptable flavoring or other taste-masking agent.

The rates of in vivo release and in vivo clearance of DMT may be influenced by means well known in the art. For example, incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Also comprehended herein are compounds modified by the covalent attachment of water-soluble polymers such as polyethylene glycol, copolymers of polyethylene glycol and polypropylene glycol, carboxymethyl cellulose, dextran, polyvinyl alcohol, cyclodextrin, cucurbituril, polyvinylpyrrolidone or polyproline. The modified compounds may exhibit substantially longer half-lives in blood following administration than do the corresponding unmodified compounds.

Depending on the delivery device employed, delivery between about 25% and about 100% of the drug product, i.e., DMT, may be achieved. It is to be understood however, that due to the nature of drug delivery devices, one of ordinary skill in the art will appreciate that not all of the drug will necessarily be delivered as is the amount delivered is dependent on the efficiency of the delivery device employed. Thus, for clarity, it is to be understood that about 25% to about 100% of the drug product delivered is dependent on the selected drug delivery method and/or device. Therefore, 100% of the drug product delivered may not be all of the drug product, but it will be all of the drug product a selected device is capable of delivering.

Intranasal Compositions

Relative to an oral dosage form such as a tablet or capsule, intranasal delivery provides for rapid absorption, faster onset of therapeutic action and avoidance of gut wall or liver first pass metabolism. For patients who have difficulty in swallowing tablets, capsules or other solids or those who have intestinal failure, the intranasal delivery route may be preferred.

The compositions of the present disclosure for nasal administration include a DMT salt or salt form (e.g. DMT succinate crystalline Form A), and optionally can also comprise other ingredients including, but not limited to, carriers and excipients, such as absorption-promoting agents which promote nasal absorption of the active ingredient after nasal administration and agents to improve brain penetration of the drug following nasal administration. Other optional excipients include diluents, binders, lubricants, glidants, disintegrants, desensitizing agents, emulsifiers, mucosal adhesives, solubilizers, suspension agents, viscosity modifiers, ionic tonicity agents, buffers, carriers, flavors and mixtures thereof. In one embodiment, the particle size of the active ingredient is less than or equal to about 60 microns, which can help to ensure uniformity of any blends of the particles with other ingredients, or to provide an adequate dispersion in a liquid vehicle.

The amount of drug absorbed depends on many factors. These factors include the drug concentration, the drug delivery vehicle, mucosal contact time, the venous drainage of the mucosal tissues, the degree that the drug is ionized at the pH of the absorption site, the size of the drug molecule, and its relative lipid solubility. Those of skill in the art can readily prepare an appropriate intranasal composition, which delivers an appropriate amount of the active agent, taking these factors into consideration.

The transport of the active ingredient across normal mucosal surfaces (such as the nasal or buccal mucosa) can be enhanced by optionally combining it with an absorption promoting agent. Examples of these absorption promoting agents include, but are not limited to, cationic polymers, surface active agents, chelating agents, mucolytic agents, cyclodextrin, polymeric hydrogels, combinations thereof, and any other similar absorption promoting agents known to those of skill in the art. Representative absorption promoting excipients include phospholipids, such as phosphatidylglycerol or phosphatidylcholine, lysophosphatidyl derivatives, such as lysophosphatidylethanolamine, lysophosphatidylcholine, lysophosphatidylglycerol, lysophosphatidylserine, or lysophosphatidic acid, polyols, such as glycerol or propylene glycol, fatty acid esters thereof such as glycerides, amino acids, and esters thereof, and cyclodextrins. Gelling excipients or viscosity-increasing excipients can also be used.

The transport of the active ingredient across normal mucosal surfaces can also be enhanced by increasing the time in which the formulations adhere to the mucosal surfaces. Mucoadhesive/bioadhesive polymers, for example, those which form hydrogels, exhibit muco-adhesion and controlled drug release properties and can be included in the intranasal or buccal, compositions described herein. Representative bioadhesive or hydrogel-forming polymers capable of binding to the nasal mucosa are well known to those of skill in the art, and include polycarbophil, polylysine, methylcellulose, sodium carboxymethylcellulose, hydroxypropyl-methylcellulose, hydroxyethyl cellulose, pectin, Carbopol 934P, polyethylene oxide 600K, one or more poloxomers such as Pluronic F127 and/or Pluronic F-68, polyisobutylene (PIB), polyisoprene (PIP), polyvinyl pyrrolidone (PVP), polyvinyl alcohol (PVA), xanthum gum, guar gum, and locust bean gum. Other nasal delivery compositions are chitosan-based and are suitable to increase the residence time of the active ingredient on mucosal surfaces, which results in increasing its bioavailability. Thiolated polymeric excipients that form covalent bonds with the cysteine-rich subdomains of the mucus membrane can also provide mucoadhesion, which prolongs the contact time between the active ingredient and the membrane.

The intranasal compositions can also include one or more preservatives. Representative preservatives include quaternary ammonium salts such as lauralkonium chloride, benzalkonium chloride, benzododecinium chloride, cetyl pyridium chloride, cetrimide, domiphen bromide; alcohols such as benzyl alcohol, chlorobutanol, o-cresol, phenyl ethyl alcohol; organic acids or salts thereof such as benzoic acid, sodium benzoate, potassium sorbate, parabens; or complex forming agents such as EDTA.

The carriers and excipients include ion-exchange microspheres which carry suitable anionic groups such as carboxylic acid residues, carboxymethyl groups, sulphopropyl groups and methylsulphonate groups. Ion-exchange resins, such ascation exchangers, can also be used. Chitosan, which is partially deacetylated chitin, or poly-N-acetyl-D-glucosamine, or a pharmaceutically acceptable salt thereof such as hydrochloride, lactate, glutamate, maleate, acetate, formate, propionate, malate, malonate, adipate, or succinate. Suitable other ingredients for use as non-ion-exchange microspheres include starch, gelatin, collagen and albumin.

The composition can also include other ingredients such as cellulose, microcrystalline cellulose, hydroxypropyl cellulose, starch, hydroxypropylmethyl cellulose, and the like. Excipients to adjust the tonicity of the composition may be added such as sodium chloride, glucose, dextrose, mannitol, sorbitol, lactose, and the like. Acidic or basic buffers can also be added to the intranasal composition to control the pH.

In addition to using absorption enhancing agents, which increase the transport of the active agents through the mucosa, and bioadhesive materials, which prolong the contact time of the active agent along the mucosa, the administration of the active agent can be controlled by using controlled release formulations. There are numerous particulate drug delivery vehicles known to those of skill in the art which can include the active ingredients, and deliver them in a controlled manner. Examples include particulate polymeric drug delivery vehicles, for example, biodegradable polymers, and particles formed of non-polymeric components. These particulate drug delivery vehicles can be in the form of powders, microparticles, nanoparticles, microcapsules, liposomes, and the like. Typically, if the active agent is in particulate form without added components, its release rate depends on the release of the active agent itself. Typically, the rate of absorption is enhanced by presenting the drug in a micronized form, wherein particles are below 20 microns in diameter. In contrast, if the active agent is in particulate form as a blend of the active agent and a polymer, the release of the active agent is controlled, at least in part, by the removal of the polymer, typically by dissolution, biodegradation, or diffusion from the polymer matrix.

Intranasal Delivery

Intranasal delivery devices are known in the art. Thus, any device suitable for delivery of drug to nasal mucosa may be used. Non-limiting examples of devices useful for the administration of liquid compositions include vapor devices (e.g., vapor inhalers), drop devices (e.g., catheters, single-dose droppers, multi-dose droppers, and unit-dose pipettes), mechanical spray pump devices (e.g., squeeze bottles, multi-dose metered-dose spray pumps, and single/duo-dose spray pumps), bi-directional spray pumps (e.g., breath-actuated nasal delivery devices), gas-driven spray systems/atomizers (e.g., single- or multi-dose HFA or nitrogen propellant-driven metered-dose inhalers, including traditional and circumferential velocity inhalers), and electrically powered nebulizers/atomizers (e.g., pulsation membrane nebulizers, vibrating mechanical nebulizers, and hand-held mechanical nebulizers). Non-limiting examples of devices useful for the administration of powder compositions (e.g., lyophilized or otherwise dried pooled compositions) include mechanical powder sprayers (e.g., hand-actuated capsule-based powder spray devices and hand-actuated powder spray devices, hand actuated gel delivery devices), breath-actuated inhalers (e.g., single- or multi-dose nasal inhalers and capsule-based single- or multi-dose nasal inhalers), and insufflators (e.g., breath-actuated nasal delivery devices).

Use of metered sprays for intranasal delivery can also be accomplished by including the active ingredient in a solution or dispersion in a suitable medium which can be administered as a spray. Representative devices of this type are disclosed in the following patents, patent applications, and publications: WO03/026559, WO02/011800, WO00/51672, WO02/068029, WO02/068030, WO02/068031, WO02/068032, WO03/000310, WO03/020350, WO03/082393, WO03/084591, WO03/090812, WO 00/41755, and the pharmaceutical literature (See, Bell, A. Intranasal Delivery Devices, in Drug Delivery Devices Fundamentals and Applications, Tyle P. (ed), Dekker, New York, 1988), Remington's Pharmaceutical Sciences, Mack Publishing Co., 1975, all of which are incorporated herein by reference.

In addition to the foregoing, the salts/salt forms can also be administered intranasally in the form of irrigations and douches, as is known in the art. Nasal irrigation involves regularly flooding the nasal cavity with solution, which includes the drug. Nasal douches are typically used by filling a nasal douche with a solution including the drug, inserting the nozzle from the douche into one nostril, opening one's mouth to breathe, and causing the solution to flow into one nostril, rinse round the septum, and discharge from the other nostril.

Means to deliver drug to the upper portion of the nasal cavity, such as the cribriform, are of particular interest herein. Also of interest is delivery of drug along the trigeminal nerve pathway.

Buccal and Sublingual Compositions and Delivery

Relative to an oral dosage form such as a tablet or capsule, oral transmucosal delivery can, like intranasal delivery, provide for rapid absorption, faster onset of therapeutic action and avoidance of liver or gut wall first pass metabolism. For patients who have difficulty in swallowing tablets, capsules or other solids or those who have intestinal failure, the buccal or sublingual delivery route is preferred.

Compositions for buccal or sublingual administration include a DMT salt or salt form (e.g. DMT succinate crystalline Form A) and at least one excipient to form a solid dosage form. The solid dosage form disintegrates in an oral cavity or under the tongue with minimal liquid exposure and at body temperature, and ideally adheres to the body tissue of the oral cavity or the tissue under the tongue via direct adhesion to tissue or, in the case of buccal administration, entrapment of the dosage form in-between the gum and inner cheek. The solid dosage form disintegrates or melts at body temperature with or without the aid of fluids, salivary fluids, mechanical erosion, or combinations thereof. Alternatively, the dosage form can be sprayed into the oral cavity or under the tongue in the form of a solution spray or a dry powder. Generally, the composition can be adhesive towards the body tissue lining the patient's oral cavity or under the tongue.

The dosage form can be, but is not limited to, tablets, a bioadhesive patch or film, sponges, lozenges, hard candies, wafers, lollipops, sprays, gums, pills, pellets, spheres, combinations thereof, and other forms known to those of skill in the art.

A buccal or sublingual film represents a particularly convenient vehicle for administering a pharmaceutical composition of the present disclosure. Examples of films include, in one aspect, a composition comprising a DMT salt or salt form (e.g. DMT succinate crystalline Form A) in a mucoadhesive polymer. Suitable mucoadhesive polymers include one or more polymers selected from cellulose derivatives, polyacrylic acids, polyacrylates, polyethylene oxides, polyvinyl pyrrolidones, polyvinyl alcohols, tragacanth, alginates, gum (including karaya gum, guar gum, xanthan gum), soluble starch, gelatin, lectin, pectin, and chitosan. In some embodiments, the mucoadhesive polymer comprises one or more polymers selected from a hydrophilic polymer, a polysaccharide and its derivatives, and a hydrogel. In some embodiments, the mucoadhesive polymer comprises one or more polymers selected from polyacrylic acids, polyacrylates, celluloses, e.g., carboxycelluloses (e.g., sodium carboxymethyl cellulose), hydroxyalkyl cellulose (e.g, hydroxypropylcellulose, hydroxyethylcellulose and hydroxyethyl ethyl cellulose), polyvinylpyrrolidone, and polyvinyl alcohol. In some embodiments, the mucoadhesive polymer comprises one or more polymers selected from Carbopol (polyacrylic acid), carboxymethyl cellulose, carboxyethyl cellulose, hydroxypropyl cellulose, hydroxypropylmethyl cellulose, and gum. In some embodiments, the mucoadhesive polymer is water-swellable. Typically, the mucoadhesive polymer is present in an amount of about 15% to about 60% by weight of the film composition.

The film compositions can further include a permeation enhancer and/or an antioxidant. For example, in some embodiments, the film composition comprises a permeation enhancer, e.g., comprising one or more permeation enhancers selected from dimethyl sulfoxide (DMSO), oleic alcohol, oleic acid, oleyl oleate, levulinic acid, propylene glycol, dipropylene glycol, ethanol, and surfactants. In some embodiments, the permeation enhancer is present in an amount of about 5% to about 30% by weight of the film composition. In some embodiments, the film composition comprises an antioxidant, e.g., tocopherol acetate.

In some embodiments, the film compositions can form a bilayer or multilayer film composition. Typically, such a bilayer or multilayer film can provide a bi-phasic release profile, which can be advantageous in certain situations. In some embodiments, a quick-release film layer comprises a water-soluble polymer. In some embodiments, the water-soluble polymer in the quick-release film comprises one or more polymers selected from hydroxypropyl methyl cellulose (HPMC), hydroxylpropyl cellulose (HPC), Povidone, polyvinyl alcohols (PVA), low molecular weight polyethylene oxide (PEO such as Poly Ox N10 supplied by Dow Chemical), and starch-based polymers (Lycoat, manufactured by Roquette). In some embodiments, the quick-release film can also optionally include a permeation enhancer, e.g., one or more permeation enhancers selected from dimethyl sulfoxide (DMSO), oleic alcohol, oleic acid, oleyl oleate, levulinic acid, propylene glycol, dipropylene glycol, ethanol, and surfactants. In some embodiments, the quick-release film can also optionally include an antioxidant, such as tocopherol acetate.

There are numerous compositions and delivery vehicles suitable for buccal or sublingual delivery of the active ingredients. In addition to DMT or a pharmaceutically acceptable salt thereof, other components of dosage forms include, but are not limited to, starch, mannitol, kaolin, calcium sulfate, inorganic salts, such as sodium chloride, powdered cellulose derivatives, dibasic and tribasic calcium phosphate, calcium sulfate, magnesium carbonate, magnesium oxide, poloxamers such as polyethylene oxide, hydroxypropyl methylcellulose, anionic excipients, cationic excipients, zwitterionic excipients, with reference to U.S. Pat. No. 6,436,950, which is incorporated herein by reference with regard to such excipients, polymeric hydrogel, powder microsphere mucoadhesive compositions, thiolated polymeric excipients, polycationic material, chitosan, crosslinked starches, fats, carbohydrates, polyols, buffers, phosphate buffers, acetate buffers, methocel, sodium chloride, water, lactic acid, benzalkonium chloride, demineralized water, cellulose, microcrystalline cellulose, hydroxypropyl cellulose, hydrogenated vegetable oil, flavoring agents, phospholipids, xylitol, cacao, combinations thereof, and other similar excipients known to those of skill in the art.

Permeation enhancers can also be present. Representative permeation enhancers include, without limitation, 23-lauryl ether, aprontinin, azone, benzalkonium chloride, cetylpyridinium chloride, cetyltrimethylammonium bromide, cyclodextrin, dextran sulfate, lauric acid, lysophosphatidylcholine, menthol, sodium methoxysalicylate, methylolearate, oleic acid, phosphatidylcholine, polyoxyethylene, polysorbatc, sodium EDTA, sodium glycocholate, sodium glycodeoxyocholate, sodium lauryl sulfate, sodium salicylate, sodium taurocholate, sodium taurodeoxycholate, sulfoxides, short and medium chain mono-, di- and triglycerides and other polyol esters, and various alkyl glycosides.

Binders can also be present. Suitable binders include substances such as celluloses, including but not limited to cellulose, methylcellulose, ethylcellulose, hydroxypropyl cellulose and hydroxymethylcellulose, polypropylpyrrolidone, polyvinylprrolidone, gelatin, polyethylene glycol, starch, natural gums such as acacia, alginates, guar, and gum arabic) and synthetic gums and waxes.

Subcutaneous Compositions and Delivery

For subcutaneous administration, aqueous suspensions, isotonic saline solutions and sterile injectable solutions may be used, optionally containing pharmaceutically acceptable excipients, which may include dispersing agents and/or wetting agents, such as propylene glycol or butylene glycol. In addition, suspensions of a DMT salt or salt form (e.g. DMT succinate crystalline Form A) may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the salt/salt form to allow for the preparation of highly concentrated solutions. Alternatively, a DMT salt or salt form (e.g. DMT succinate crystalline Form A) may be in powder form for constitution with a suitable vehicle, e.g., sterile pyrogen-free water, before use. The solution or suspension may be administered subcutaneously to the subject by injection using well-known devices and techniques. Any appropriate syringe may conveniently be used, including an autoinjector which may allow self-administration.

Dosing

The dosage amount of a DMT salt or salt form (e.g. DMT succinate crystalline Form A) administered to a patient, as defined herein, with a neurological disease or condition, is typically from about 0.1 mg/kg to about 1 mg/kg. A typical human dose (for an adult weighing 50-80 kg) would equate to a dose of about 5 mg to about 80 mg. In one embodiment, the dose is about 10 mg to about 60 mg, such as about 20-60 mg, about 30-60 mg, about 40-60 mg, or any specific amount therebetween, including 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, and 60 mg. In this disclosure, when ranges are set forth, such as "about 20-60 mg" the inventor contemplates all discrete values within that range, some of which are specifically mentioned, but all of which are not, simply for the purpose of brevity.

In a particular embodiment, a DMT salt or salt form (e.g. DMT succinate crystalline Form A) may be administered to a patient in one or more doses over a 24 hour period, e.g. 1, 2, 3, 4 or 5 doses. However, the total dose administered to the subject should not exceed about 100 mg over a 24 hour period.

Uses

In one aspect, the present disclosure provides a DMT salt selected from DMT succinate, DMT malate, DMT sulfate and DMT phosphate (e.g. DMT succinate) for use in treating a neurological disease or condition.

In one aspect, the present disclosure provides a DMT salt form selected from DMT fumarate Form A, DMT succinate Form A, DMT malate Form A, DMT oxalate Form A and DMT sulfate Form A (e.g. DMT succinate Form A) for use in treating a neurological disease or condition.

In one aspect, the present disclosure provides a method of treating a neurological disease or condition, comprising administering to a subject an effective amount of a DMT salt selected from DMT succinate, DMT malate, DMT sulfate and DMT phosphate (e.g. DMT succinate).

In one aspect, the present disclosure provides a method of treating a neurological disease or condition, comprising administering to a subject an effective amount of a DMT salt form selected from DMT fumarate Form A, DMT succinate Form A, DMT malate Form A, DMT oxalate Form A and DMT sulfate Form A (e.g. DMT succinate Form A).

Any suitable method generally available to administer DMT fumarate may be used to administer a DMT salt or salt form of the present disclosure (e.g. DMT succinate crystalline Form A). Conveniently, a DMT salt or salt form (e.g. DMT succinate crystalline Form A) may be administered orally, parenterally, transmucosally intranasally buccally or sublingually. In one aspect, a DMT salt or salt form (e.g. DMT succinate crystalline Form A) may be administered parenterally, e.g. intravenously or intramuscularly by injection.

In any one of the abovementioned aspects the neurological disease or condition may be, for example, a neuropsychiatric disorder.

Examples of neuropsychiatric disorders which may be treated with a DMT salt or salt form (e.g. DMT succinate crystalline Form A) include depression (e.g. TRD), anxiety, bipolar disorder, post-traumatic stress disorder, abnormalities of mood or emotion, including the above conditions, dysthymia, schizoaffective disorder, schizophrenia and other psychotic disorders, panic disorder, traumatic stress disorders, phobic disorders, eating disorders and personality disorders with abnormal mood, such as borderline personality disorder, schizoid and schizotypal disorders and suicide ideation, or rumination/unproductive repetitive thoughts negatively impacting one's behavior/mood/ability to focus.

In any one of the abovementioned aspects the neurological disease or condition may be, for example, addiction.

Examples of addiction which may be treated with a DMT salt or salt form (e.g. DMT succinate crystalline Form A) include substance use disorder such as addiction to nicotine, alcohol, cocaine, opioids, amphetamine, methamphetamine, heroin, morphine, phencyclidine, 3,4-methylenedioxymethamphetamine, as well as other addictive substances.

In any one of the abovementioned aspects the neurological disease or condition may be, for example, addictive behavior.

Examples of addictive behavior which may be treated with a DMT salt or salt form (e.g. DMT succinate crystalline Form A) include addiction to eating, gambling, sex, pornography, videogames, work, exercise, spiritual obsession, self-harm, travel and shopping.

In a particular embodiment, the present disclosure provides a method of treating depression (including severe depression such as treatment-resistant depression, major depressive disorder and persistent depressive disorder, catatonic depression, a depressive disorder due to a medical condition, or postpartum depression), comprising administering to a subject an effective amount of a DMT salt selected from DMT succinate, DMT malate, DMT sulfate and DMT phosphate (e.g. DMT succinate). In one embodiment, the DMT salt may be administered transmucosally (e.g. buccally, sublingually or intranasally).

In a particular embodiment, the present disclosure provides a method of treating depression (including severe depression such as treatment-resistant depression, major depressive disorder and persistent depressive disorder, catatonic depression, a depressive disorder due to a medical condition, or postpartum depression), comprising administering to a subject an effective amount of a DMT salt form selected from DMT fumarate Form A, DMT succinate Form A, DMT malate Form A, DMT oxalate Form A and DMT sulfate Form A (e.g. DMT succinate Form A). In one embodiment, the DMT salt form may be administered transmucosally (e.g. buccally, sublingually or intranasally).

In a particular embodiment, the present disclosure provides a method of treating depression (including severe depression such as treatment-resistant depression, major depressive disorder and persistent depressive disorder, catatonic depression, a depressive disorder due to a medical condition, or postpartum depression), comprising administering subcutaneously to a subject an effective amount of a DMT salt selected from DMT succinate, DMT malate, DMT sulfate and DMT phosphate (e.g. DMT succinate).

In a particular embodiment, the present disclosure provides a method of treating depression (including severe depression such as treatment-resistant depression, major depressive disorder and persistent depressive disorder, catatonic depression, a depressive disorder due to a medical condition, or postpartum depression), comprising administering subcutaneously to a subject an effective amount of a DMT salt form selected from DMT fumarate Form A, DMT succinate Form A, DMT malate Form A, DMT oxalate Form A and DMT sulfate Form A (e.g. DMT succinate Form A).

Combination Therapy

The methods described herein include administering a DMT salt or salt form (e.g. DMT succinate crystalline Form A) as the sole active ingredient. However, also encompassed within the scope of the present disclosure are methods for treating a neurological disease or condition that comprise administering a DMT salt or salt form (e.g. DMT succinate crystalline Form A) in combination with one or more additional agents.

In one aspect, these additional agents are therapeutic agents appropriate for the disease or disorder that is being treated, as is known in the art. In some embodiments, a DMT salt or salt form (e.g. DMT succinate crystalline Form A) may be administered to the subject in combination with one or more anti-depressant or anti-anxiety drugs, such as SSRIs, tricyclic antidepressants (TCAs), monoamine oxidase inhibitors (MAOIs), or serotonin norepinephrine reuptake inhibitors (SNRIs).

In some embodiments, the disclosure provides a method of reducing anxiety in a subject undergoing treatment with a DMT salt or salt form (e.g. DMT succinate crystalline Form A), the method comprising administering to the subject: i) a DMT salt or salt form (e.g. DMT succinate crystalline Form A) and ii) one or more benzodiazepines.

In some embodiments, the one or more benzodiazepines are administered to the subject at or around the same time as a DMT salt or salt form (e.g. DMT succinate crystalline Form A). In some embodiments, the one or more benzodiazepines are administered to the subject prior to administration of a DMT salt or salt form (e.g. DMT succinate crystalline Form A), such as about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes before administration of the psilocybin or precursor or derivative thereof. In some embodiments, the one or more benzodiazepines are administered to the subject after a DMT salt or salt form (e.g. DMT succinate crystalline Form A), such as about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes after administration of the psilocybin or precursor or derivative thereof.

In some embodiments, the benzodiazepine is selected from the group consisting of adinazolam, alprazolam, bentazepam, bretazenil, bromazepam, bromazolam, brotizolam, camazepam, chlordiazepoxide, cinazepam, cinolazepam, clobazam, clonazepam, clonazolam, clorazepate, clotiazepam, cloxazolam, delorazepam, deschloroetizolam, diazepam, diclazepam, estazolam, ethyl carfluzepate, ethyl loflazepate, etizolam, flualprazolam, flubromazepam, flubromazolam, fluclotizolam, flunitrazepam, flunitrazolam, flurazepam, flutazolam, flutoprazepam, halazepam, ketazolam, loprazolam, lorazepam, lormetazepam, meclonazepam, medazepam, metizolam, mexazolam, midazolam, nifoxipam, nimetazepam, nitemazepam, nitrazepam, nitrazolam, nordiazepam, norflurazepam, oxazepam, phenazepam, pinazepam, prazepam, premazepam, pyrazolam, quazepam, rilmazafone, temazepam, tetrazepam, and triazolam.

In certain embodiments, a patient is administered a DMT salt or salt form (e.g. DMT succinate crystalline Form A) as described herein along with one or more 5-$HT_{2A}$ specific antagonists and/or inverse agonists. In some embodiments, the patient is administered a DMT salt or salt form (e.g. DMT succinate crystalline Form A) and the one or more 5-$HT_{2A}$ specific antagonists and/or inverse agonists at the same time. In other embodiments, the patient is administered one or more 5-$HT_{2A}$ specific antagonists and/or inverse agonists prior to a DMT salt or salt form (e.g. DMT succinate crystalline Form A) administration, such as, but not limited to about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes before a DMT salt or salt form (e.g. DMT succinate crystalline Form A) administration. In some embodiments, the patient is administered one or more 5-HT$_{2A}$ specific antagonists and/or inverse agonists after a DMT salt or salt form (e.g. DMT succinate crystalline Form A) administration, such as, but not limited to about 10 minutes, about 15 minutes, about 20 minutes, about 30 minutes, about 45 minutes, about 60 minutes, about 75 minutes, about 90 minutes, about 105 minutes, about 120 minutes, about 150 minutes, or about 180 minutes after a DMT salt or salt form (e.g. DMT succinate crystalline Form A) administration.

Suitable 5-HT$_{2A}$ antagonists include but are not limited to, trazodone, mirtazapine, metergoline, ketanserin, ritanserin, nefazodone, clozapine, olanzapine, quetiapine, risperidone, asenapine, MDL-100907, cyproheptadine, pizotifen, LY-367,265, 2-alkyl-4-aryl-tetrahydro-pyrimido-azepine, 9-aminomethyl-9,10-dihydroanthracene (AMDA), haloperidol, chlorpromazine, hydroxyzine (atarax), 5-MeO—NBpBrT, niaprazine, altanserin, aripiprazole, etoperidone, setoperone, chlorprothixene, cinaserin, adatanserin, medifoxamine, rauwolscine, phenoxybenzamine, pruvanserin, deramciclane, nelotanserin, lubazodone, mepiprazole, xylamidine, R-(+)-alpha-(2,3-dimethoxyphenyl)-1-[2-(4-fluorophenethyl)]-4-piperidinemethanol (M100907), mianserin, AT 1015, DV 7028, eplivanserin, 4F 4PP, fanaserin, alpha-phenyl-1-(2-phenylethyl)-4-piperidinemethanol (MDL 1 1,939), melperone, mesulergine, paliperidone, 1-[2-(3,4-Dihydro-1/-/-2-benzopyran-1-yl)ethyl]-4-(4-fluorophenyl)piperazine dihydrochloride (PNU 96415E), (2R,4R)-5-[2-[2-[2-(3-methoxyphenyl)ethyl]phenoxy]ethyl]-1-methyl-3-pyrrolidinol(R-96544), sarpogrelate, spiperone, ziprasidone, zotepine, and 7-[[4-[2-(4-fluorophenyl)ethyl]-1-piperazinyl]carbonyl]-1-indole-3-carbonitrile (EMD 281014).

Suitable 5-HT$_{2A}$ reverse agonists include but are not limited to, AC-90179, nelotanserin (APD-125), eplivanserin, pimavanserin (ACP-103), and volinaserin.

In some embodiments, the disclosure provides a method of reducing the negative side effects associated with a traumatic psychedelic experience in a patient undergoing treatment with a DMT salt or salt form (e.g. DMT succinate crystalline Form A). In one aspect the method comprising administering to the patient: i) a DMT salt or salt form (e.g. DMT succinate crystalline Form A), and ii) one or more 5-HT$_{2A}$ specific antagonists and/or inverse agonists. In another aspect, the method comprising administering to the patient: i) a DMT salt or salt form (e.g. DMT succinate crystalline Form A), and ii) one or more cannabinoids or cannabinoid derivatives.

In some embodiments, the cannabinoid is selected from the group consisting of THC (tetrahydrocannabinol), THCA (tetrahydrocannabinolic acid); CBD (cannabidiol); CBDA (cannabidiolic acid); CBN (cannabinol); CBG (cannabigerol); CBC (cannabichromene); CBL (cannabicyclol); CBV (cannabivarin); THCV (tetrahydrocannabivarin); CBDV (cannabidivarin); CBCV (cannabichromevarin); CBGV (cannabigerovarin); CBGM (cannabigerol monomethyl ether); CBE (cannabielsoin); and CBT (cannabicitran). In particular embodiments, the cannabinoid is CBD (cannabidiol).

Dosage regimens may be adjusted to provide the optimum desired response. Treatment dosages may be titrated using routine methods known to those of skill in the art to optimize safety and efficacy.

In a further aspect of the present disclosure, when treating a neuropsychiatric disease or disorder, such as depression (e.g. TRD), anxiety or an addiction, compositions of the present disclosure may be administered in conjunction with psychotherapy, talk therapy, cognitive behavioral therapy, exposure therapy, biofeedback therapy (e.g. EEG-assisted therapy and virtual reality assisted therapy), systematic desensitization, mindfulness, dialectical behavior therapy, interpersonal therapy, eye movement desensitization and reprocessing, social rhythm therapy, acceptance and commitment therapy, family-focused therapy, psychodynamic therapy, light therapy, computer therapy (including digital cognitive behavioral therapy), cognitive remediation, exercise, or other types of therapy such as transcranial magnetic stimulation (TMS). In one embodiment, a DMT salt or salt form (e.g. DMT succinate crystalline Form A) may be administered to treat depression in conjunction with digital cognitive behavioral therapy, for example, using the digital program DEPREXIS®. In one embodiment, a DMT salt or salt form (e.g. DMT succinate crystalline Form A) may be administered (for example, to treat depression or anxiety) in conjunction with therapy using a transdiagnostic approach (cf. J Consult Clin Psychol. 2020 March; 88(3): 179-195).

All references, articles, publications, patents, patent publications, and patent applications cited herein are incorporated by reference in their entireties for all purposes. However, mention of any reference, article, publication, patent, patent publication, and patent application herein is not, and should not, be taken as acknowledgment or any form of suggestion that they constitute valid prior art or form part of the common general knowledge in any country in the world.

In the following Examples, product samples were analyzed according to the following methodologies:

XRPD: XRPD patterns were collected with a PANalytical X'Pert PRO MPD or PANalytical Empyrean diffractometer using an incident beam of Cu radiation produced using a long, fine-focus source. An elliptically graded multilayer mirror was used to focus Cu Kα X-rays through the specimen and onto the detector. Prior to the analysis, a silicon specimen (NIST SRM 640f) was analyzed to verify the observed position of the Si 111 peak is consistent with the NIST-certified position. A specimen of the sample was sandwiched between 3-µm-thick films and analyzed in transmission geometry. A beam-stop, short anti-scatter extension, and anti-scatter knife edge were used to minimize the background generated by air. Soller slits for the incident and diffracted beams were used to minimize broadening and asymmetry from axial divergence. Diffraction patterns were collected using a scanning position-sensitive detector (X'Celerator) located 240 mm from the specimen and Data Collector software v. 5.5. The data acquisition parameters are listed in the image of each pattern displayed herein.

Variable Temperature XRPD: XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Data were collected and analyzed using Data Collector software v. 2.2b. Prior to the analysis, a silicon specimen (NIST SRM 640f) was analyzed to verify the observed position of the Si 111 peak is consistent with the NIST-certified position. A specimen of the sample was packing in a nickel-coated copper well. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 2.2b. The data acquisition parameters for each pattern are displayed herein including the divergence slit (DS) and the incident-beam antiscatter slit (SS). An Anton Paar temperature-humidity chamber (THC) was used to collect in-situ XRPD patterns as a function of temperature. The temperature of the specimen was changed with a Peltier thermoelectric device located directly under the specimen holder and monitored with a platinum-100 resistance sensor located in the specimen holder. The thermoelectric device was powered and controlled by an Anton Paar TCU 50 interfaced with Data Collector.

TGA: TGA was performed using a Mettler-Toledo TGA/DSC3+ analyzer. Temperature and enthalpy adjustments were performed using indium, tin, and zinc, and then verified with indium. The balance was verified with calcium oxalate. The sample was placed in an open aluminum pan. The pan was then inserted into the TG furnace. A weighed aluminum pan configured as the sample pan was placed on the reference platform. The furnace was heated under nitrogen. The sample was analyzed from 25° C. to 350° C. at 10° C./min.

DSC: DSC was performed using a Mettler-Toledo DSC3+ differential scanning calorimeter. A tau lag adjustment is performed with indium, tin, and zinc. The temperature and enthalpy are adjusted with octane, phenyl salicylate, indium, tin and zinc. The adjustment is then verified with octane, phenyl salicylate, indium, tin, and zinc. The sample was placed into a hermetically sealed aluminum DSC pan, the weight was accurately recorded, the lid was pierced, and the sample was inserted into the DSC cell. A weighed aluminum pan configured as the sample pan was placed on the reference side of the cell. The pan lid was pierced prior to sample analysis. The sample was analyzed from −30° C. to 250° C. at 10° C./min.

Cyclic DSC: The sample cell was equilibrated at −30.0° C., then heated under nitrogen at a rate of 10.0° C./min up to 135° C. The sample cell was then allowed to cool and equilibrate at 25.0° C. It was again heated at a rate of 10.0° C. min up to 250.0° C.

DVS: Automated vapor sorption (VS) data were collected on a Surface Measurement System DVS Intrinsic instrument. Samples were not dried prior to analysis. Sorption and desorption data were collected over a range from 5% to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples.

EXAMPLES

A. Fumarate Form A

A slurry containing 49.4 mg of fumaric acid and 79.2 mg of DMT in 1 mL of acetone was stirred at room temperature for 1 day. Solids were collected with a Swinnex® positive pressure filter assembly using a 0.2-µm nylon filter.

B. Succinate Form A

The salt was prepared from either acetone or ethanol and successfully recrystallized from a variety of solvent and solvent mixtures including ACN, DMF, EtOAc, HFIPA, IPA, MeOH, NMP, and TFE.

1) Preparation of Succinate Form A in acetone: A slurry containing 65.1 mg of succinic acid and 98.8 mg of DMT in 1 mL of acetone was stirred at room temperature for 1 day. Solids were collected with a Swinnex® positive pressure filter assembly using a 0.2-µm nylon filter.

2) Preparation of Succinate Form A in ethanol: A slurry containing 57.3 mg of succinic acid and 86.4 mg of DMT in 0.5 mL of ethanol was stirred at room temperature for 2 days. Solids were collected with a Swinnex® positive pressure filter assembly using a 0.2-µm nylon filter.

C. Malate Form A

A slurry containing 63.6 mg of L-(−)-malic acid and 81.0 mg of DMT in 0.5 mL of ethanol was stirred at room temperature for 2 days. Solids were collected with a Swinnex® positive pressure filter assembly using a 0.2-µm nylon filter.

D. Sulfate Form A

A slurry containing 28.5 µL of 95-98% concentrated sulfuric acid and 95.8 mg of DMT in 0.5 mL of ethanol was stirred at −20° C. for 5 days. Solids were collected with a Swinnex® positive pressure filter assembly using a 0.2-µm PTFE filter.

E. Oxalate Form A

A slurry containing 49.5 mg of oxalic acid and 99.4 mg of DMT in 1 mL of acetone was stirred at room temperature for 9 days. A single crystal was culled prior to collecting the remaining solids with a Swinnex® positive pressure filter assembly using a 0.2-µm nylon filter.

F. Phosphate Salt

A slurry containing 27.0 µL of 85% concentrated phosphoric acid and 76.1 mg of DMT in 0.5 mL of ethanol was stirred at room temperature for 2 days. Solids were collected with a Swinnex® positive pressure filter assembly using a 0.2-µm nylon filter.

Processes A. to E. above are summarized in Table 1:

TABLE 1

| Co-former | Conditions | Observations | XRPD Result |
|---|---|---|---|
| fumaric acid 1:1 | 1) DMT solution in acetone was added to fumaric acid 2) stirred, RT, 1 day 3) positive pressure filtration | 1) cloudy solution 2) white slurry 3) white solids: fines & aggregates | Fumarate Form A |
| Succinic acid 1:1 | 1) DMT solution in acetone was added to succinic acid 2) stirred, RT, 1 day 3) positive pressure filtration | 1) cloudy solution 2) off-white slurry 3) white solids: fines & aggregates | Succinate Form A |
| | 1) DMT solution in EtOH was added to succinic acid | 1) clear solution 2) off-white slurry | Succinate Form A |

TABLE 1-continued

| Co-former | Conditions | Observations | XRPD Result |
|---|---|---|---|
| | 2) stirred, RT, 2 days<br>3) positive pressure filtration | 3) white solids: fines & aggregates | |
| L-malic acid 1:1 | 1) DMT solution in EtOH was added to L-malic acid<br>2) stirred, RT, 2 days<br>3) positive pressure filtration | 1) clear solution<br>2) white slurry<br>3) white solids: fines & aggregates | Malate Form A |
| Sulfuric acid 1:1 | 1) sulfuric acid was added to DMT solution in EtOH<br>2) stirred, RT, 2 days<br>3) stirred, −20° C., 5 days<br>4) positive pressure filtration | 1) clear solution<br>2) clear brownish solution<br>3) off-white slurry<br>4) off-white solids: fines & aggregates | Sulfate Form A |
| oxalic acid 1:1 | 1) DMT solution in acetone was added to oxalic acid<br>2) stirred, RT, 1 days<br>3) positive pressure filtration after further 8 days | 1) cloudy solution<br>2) white solids in clear solution<br>3) off-white solids in clear solution: blades & plates | Oxalate Form A |

G. Recrystallization of DMT Succinate Salt in Various Solvents

The methods are summarized in Table 2:

TABLE 2

| Solvent | Conditions | Observations | XRPD |
|---|---|---|---|
| ACN | 1) slurry, 50° C., 7 days<br>2) centrifuge & decant | 1) white slurry<br>2) white fines | Succinate Form A |
| 90:10 ACN/H$_2$O (a$_w$ = 0.87) | 1) slurry, 5° C., 15 days<br>2) centrifuge & decant | 1) solids present<br>2) white fines | Succinate Form A |
| | 1) slurry, RT, 7 days<br>2) centrifuge & decant | 1) white slurry<br>2) white; fines | Succinate Form A |
| DMF | 1) VD (w/acetone), RT, 20 days<br>2) decanted | 1) chunk in clear solution<br>2) white tablets | Succinate Form A |
| EtOAc | VS, RT, 7 days | fines/aggregates | Succinate Form A |
| EtOH | 1) slurry, RT, 7 days<br>2) centrifuge & decant | 1) white slurry<br>2) white fines | Succinate Form A |
| | 1) slurry, 50° C., 7 days<br>2) centrifuge & decant | 1) white slurry<br>2) white fines | Succinate Form A |
| | FE | plates, dendritic | Succinate Form A |
| | 1) CC, 65° C. to −20° C.<br>2) freezing, −20° C., 1 day<br>3) decanted | 1) clear solution<br>2) colorless solids<br>3) tablets | Succinate Form A |
| HFIPA | 1) FE<br>2) scratched w/spatula<br>3) RT, 5 days | 1) clear gel<br>2) some crystallization<br>3) gel; plates, fines | Succinate Form A |
| 95:5 IPA/H$_2$O (a$_w$ = 0.44) | 1) slurry, 5° C., 15 days<br>2) centrifuge & decant | 1) slurry<br>2) white fines | Succinate Form A |
| | 1) slurry, RT, 7 days<br>2) centrifuge & decant | 1) white slurry<br>2) white fines | Succinate Form A |
| MeOH | 1) slurry, 5° C., 15 days<br>2) centrifuge & decant | 1) slurry<br>2) white fines | Succinate Form A |
| | 1) slurry, RT, 7 days<br>2) centrifuge & decant | 1) white slurry<br>2) white fines | Succinate Form A |
| | VD (w/Et$_2$O), RT, 1 day | plates & pyramidal | Succinate Form A[1] |
| | SE | layered hexagonal plates & dendritic | Succinate Form A |
| NMP | 1) slurry, 5° C., 15 days<br>2) centrifuge & decant | 1) slurry<br>2) white fines | Succinate Form A |
| TFE | 1) SE<br>2) scratched w/spatula<br>3) RT, 13 days | 1) clear gel<br>2) —<br>3) spherulites/fines | Succinate Form A |

[1]SCXRD

H. Scale Up Preparation of DMT Succinate Form A

A slurry containing 1.3014 g of succinic acid and 2.0447 g of DMT in 10 mL of ethanol was stirred at room temperature for 4 days. Solids were isolated by water aspirated vacuum filtration and dried at room temperature under vacuum for 1 day. The yield was 95.4% from theoretical.

Process H. above is summarized in Table 3:

TABLE 3

| Conditions | Observations | Yield (%) | XRPD Result |
|---|---|---|---|
| 1) EtOH slurry of 1:1 DMT/succinic acid, RT, 4 days<br>2) vacuum filtration<br>3) vacuum oven, RT, 1 day | 1) off-white slurry<br>2) free flowing off-white solids<br>3) free-flowing off-white solids | 95.4% | Succinate Form A |

I. Preparation of DMT Succinate Form a Single Crystal

A saturated solution of DMT Succinate Form A was generated from succinic acid (1.3014 g) and DMT (2.0447 g) in methanol (10 mL) at room temperature. The solution was filtered with a 0.2-μm nylon syringe filter into a clean 1-dram vial. The 1-dram vial was placed, uncapped, inside a 20-mL vial containing 2 mL of diethyl ether. The 20-mL vial was capped and left at room temperature for 1 day. Single crystals were evident within 1 day. A single crystal was culled and the structure was successfully elucidated (FIG. 17).

A comparison of properties of six new salt forms of DMT prepared according to the above procedures is given in Table 4 below:

TABLE 4

|  | DMT Fumarate Form A | DMT Succinate Form A | DMT Malate Form A | DMT Oxalate Form A | DMT Sulfate Form A | DMT Phosphate Material A |
|---|---|---|---|---|---|---|
| Physical appearance | white solid | white solid | white solid | off-white solid | off-white solid | white/off-white solid, possibly gel |
| Composition [XRPD] | unsolvated 1:1 fumarate salt | dense 1:1 succinate salt | unsolvated 1:1 malate salt | consistent with oxalate A calculated pattern note: SCXRD shows anhydrous 1:1 oxalate salt | unsolvated 1:1 sulfate salt | — |
| Composition [$^1$H NMR] | consistent with 1:1 fumarate salt | consistent with 1:1 succinate salt | consistent with 1:1 malate salt | — | consistent with chemical structure; 0.4 mol/mol EtOH | consistent with chemical structure |
| Melting point (° C.) [DSC] | 151.8; sharp endo with onset at 151.8° C. | 141.9; sharp endo with onset at 141.9° C. | 109.1; broad endo at 70. 3° C. (likely residual water) followed by large sharp endo with onset at 109.1° C. | shallow endo at 67.1° C. followed by large sharp endo with onset at 135.2° C. (likely melt); small sharp endo at 150.3° C. (possibly 2nd form) | 105.0° C.; sharp endo with onset at 105.0° C. | — |
| Aqueous Solubility (mg/mL) [visual estimation] | 50 | 46 | 93 | — | — | — |
| Residual solvent /H$_2$O [TGA] | 0.2% wt. loss over 39° C. to 160° C. | 0.8% wt. loss over 82° C. to 153° C. | 4.5% wt. loss over 33° C. to 92° C. (0.84 mol/mol water) | 0.5% wt. loss over 47° C. to 173° C. (0.02 mol/mol acetone) | 0.1% wt. loss over 47° C. to 125° C. | — |
| Hygroscopicity [DVS] | limited 5% to 95%: 0.573% wt. gain (0.1 mol/mol water) | low 5% to 95%: 0.171% wt. gain (0.03 mol/mol water) | significant 5% to 75%: 1.21% wt. gain (0.4 mol/mol water) 75% to 95%: 9.75% wt. gain | — | — | — |

TABLE 4-continued

| | DMT Fumarate Form A | DMT Succinate Form A | DMT Malate Form A | DMT Oxalate Form A | DMT Sulfate Form A | DMT Phosphate Material A |
|---|---|---|---|---|---|---|
| | 95% to 5%: 0.679% wt. loss some hysteresis | 95% to 5%: 0.175% wt. loss some hysteresis | (1.7 mol/mol water) 95% to 75%: 9.59% wt. loss 75% to 5%: 1.37% wt. loss | | | |
| Hygroscopicity [physical appearance at high RH] | white solid (90% RH, RT, 7 days) | white solid (90% RH, RT, 7 days) * | white solid (90% RH, RT, 7 days) | — | yellow-brown oil/deliquesced (90% RH, RT, 1 day) | wet off-white solids (90% RH, RT, 1d); free-flowing white solids (vacuum oven, 50° C., 3 days) |

* Follow-up study data into the physical stability of DMT succinate Form A at 58%, 75%, & 80% RH at 25.0° C. after 7 days showed no change in Form A.
A weight gain of 0.265% was measured at 80% RH after 24 hours, further confirming the material to be slightly hygroscopic X-ray powder diffraction (XRPD) peak positions for five XRPD patterns of DMT salt forms have been determined. Observed and prominent or representative peaks are included below and in the Figures, while characteristic peaks are not included.

J. DMT Fumarate Form A

One pattern was analyzed; preferred orientation and particle statistic effects were not assessed. Observed peaks are shown in FIG. 1 and Table 5 below, and prominent peaks are listed in Table 6 below. The XRPD pattern of DMT Fumarate Form A was successfully indexed by a single unit cell and provides strong evidence that the pattern is representative of a single crystalline phase. The form has a triclinic unit cell likely containing two fumaric acid anions and two DMT cations. Consequently, the estimated formula unit volume of 404 Å3 calculated from the indexing results would be consistent with an anhydrate.

TABLE 5

| °2θ | d space (Å) | Intensity (%) |
|---|---|---|
| 7.66 ± 0.20 | 11.532 ± 0.301 | 10 |
| 10.19 ± 0.20 | 8.674 ± 0.170 | 13 |
| 10.78 ± 0.20 | 8.200 ± 0.152 | 21 |
| 12.38 ± 0.20 | 7.144 ± 0.115 | 3 |
| 13.45 ± 0.20 | 6.578 ± 0.097 | 14 |
| 14.49 ± 0.20 | 6.108 ± 0.084 | 10 |
| 15.03 ± 0.20 | 5.890 ± 0.078 | 4 |
| 15.38 ± 0.20 | 5.757 ± 0.074 | 18 |
| 15.73 ± 0.20 | 5.629 ± 0.071 | 24 |
| 15.97 ± 0.20 | 5.545 ± 0.069 | 24 |
| 16.37 ± 0.20 | 5.411 ± 0.066 | 8 |
| 16.57 ± 0.20 | 5.346 ± 0.064 | 10 |
| 16.93 ± 0.20 | 5.233 ± 0.061 | 50 |
| 18.33 ± 0.20 | 4.836 ± 0.052 | 67 |
| 18.89 ± 0.20 | 4.694 ± 0.049 | 3 |
| 19.61 ± 0.20 | 4.523 ± 0.046 | 42 |
| 19.75 ± 0.20 | 4.492 ± 0.045 | 29 |
| 20.49 ± 0.20 | 4.331 ± 0.042 | 91 |
| 21.15 ± 0.20 | 4.197 ± 0.039 | 10 |
| 21.68 ± 0.20 | 4.096 ± 0.037 | 7 |
| 22.36 ± 0.20 | 3.973 ± 0.035 | 16 |
| 22.49 ± 0.20 | 3.950 ± 0.035 | 13 |
| 22.73 ± 0.20 | 3.909 ± 0.034 | 6 |
| 23.17 ± 0.20 | 3.836 ± 0.033 | 4 |
| 23.55 ± 0.20 | 3.775 ± 0.032 | 53 |
| 23.91 ± 0.20 | 3.719 ± 0.031 | 62 |
| 24.94 ± 0.20 | 3.567 ± 0.028 | 100 |
| 26.03 ± 0.20 | 3.420 ± 0.026 | 11 |
| 26.65 ± 0.20 | 3.342 ± 0.025 | 3 |
| 27.11 ± 0.20 | 3.287 ± 0.024 | 5 |
| 27.73 ± 0.20 | 3.214 ± 0.023 | 5 |
| 27.81 ± 0.20 | 3.205 ± 0.023 | 5 |
| 28.11 ± 0.20 | 3.172 ± 0.022 | 4 |
| 28.28 ± 0.20 | 3.153 ± 0.022 | 5 |
| 28.76 ± 0.20 | 3.102 ± 0.021 | 4 |
| 29.24 ± 0.20 | 3.052 ± 0.020 | 4 |
| 29.62 ± 0.20 | 3.013 ± 0.020 | 5 |
| 29.81 ± 0.20 | 2.995 ± 0.020 | 9 |
| 30.34 ± 0.20 | 2.944 ± 0.019 | 7 |
| 30.94 ± 0.20 | 2.888 ± 0.018 | 5 |
| 31.20 ± 0.20 | 2.864 ± 0.018 | 5 |
| 32.29 ± 0.20 | 2.770 ± 0.017 | 4 |
| 33.09 ± 0.20 | 2.705 ± 0.016 | 2 |
| 33.47 ± 0.20 | 2.675 ± 0.016 | 12 |
| 34.16 ± 0.20 | 2.623 ± 0.015 | 4 |
| 34.86 ± 0.20 | 2.572 ± 0.014 | 10 |

TABLE 6

| °2θ | d space (Å) | Intensity (%) |
|---|---|---|
| 10.78 ± 0.20 | 8.200 ± 0.152 | 21 |
| 15.38 ± 0.20 | 5.757 ± 0.074 | 18 |
| 15.73 ± 0.20 | 5.629 ± 0.071 | 24 |
| 15.97 ± 0.20 | 5.545 ± 0.069 | 24 |
| 16.93 ± 0.20 | 5.233 ± 0.061 | 50 |
| 18.33 ± 0.20 | 4.836 ± 0.052 | 67 |
| 19.61 ± 0.20 | 4.523 ± 0.046 | 42 |
| 19.75 ± 0.20 | 4.492 ± 0.045 | 29 |
| 20.49 ± 0.20 | 4.331 ± 0.042 | 91 |
| 23.55 ± 0.20 | 3.775 ± 0.032 | 53 |
| 23.91 ± 0.20 | 3.719 ± 0.031 | 62 |
| 24.94 ± 0.20 | 3.567 ± 0.028 | 100 |

K. DMT Succinate Form A

One pattern was analyzed, and preferred orientation and particle statistic effects were assessed through comparison to the calculated XRPD pattern from the single crystal structure and determined to be negligible. Observed peaks are shown in FIG. 2 and Table 7 below, and representative peaks are listed in Table 8 below. The crystal system is orthorhombic and the space group is P212121. The cell parameters and calculated volume are: a=8.50595(7) Å, b=10.69563(10) Å, c=16.96938(14) Å, α=90°, β=90°, γ=90°, V=1543.82(2) Å3.

TABLE 7

| °2θ | d space (Å) | Intensity (%) |
|---|---|---|
| 9.75 ± 0.20 | 9.064 ± 0.185 | 20 |
| 11.61 ± 0.20 | 7.616 ± 0.131 | 8 |
| 13.28 ± 0.20 | 6.662 ± 0.100 | 2 |
| 14.27 ± 0.20 | 6.202 ± 0.086 | 46 |
| 14.72 ± 0.20 | 6.013 ± 0.081 | 8 |
| 16.55 ± 0.20 | 5.352 ± 0.064 | 5 |
| 16.90 ± 0.20 | 5.242 ± 0.062 | 68 |
| 17.36 ± 0.20 | 5.104 ± 0.058 | 13 |
| 17.71 ± 0.20 | 5.004 ± 0.056 | 4 |
| 18.82 ± 0.20 | 4.711 ± 0.050 | 5 |
| 19.58 ± 0.20 | 4.530 ± 0.046 | 29 |
| 20.30 ± 0.20 | 4.371 ± 0.043 | 3 |
| 20.58 ± 0.20 | 4.312 ± 0.041 | 100 |
| 20.90 ± 0.20 | 4.247 ± 0.040 | 6 |
| 21.51 ± 0.20 | 4.128 ± 0.038 | 4 |
| 22.23 ± 0.20 | 3.996 ± 0.035 | 15 |
| 22.50 ± 0.20 | 3.948 ± 0.035 | 13 |
| 22.86 ± 0.20 | 3.887 ± 0.034 | 10 |
| 23.08 ± 0.20 | 3.850 ± 0.033 | 64 |
| 23.39 ± 0.20 | 3.800 ± 0.032 | 53 |
| 24.83 ± 0.20 | 3.583 ± 0.028 | 45 |
| 25.17 ± 0.20 | 3.535 ± 0.028 | 16 |
| 26.19 ± 0.20 | 3.400 ± 0.026 | 6 |
| 26.79 ± 0.20 | 3.325 ± 0.024 | 20 |
| 27.27 ± 0.20 | 3.268 ± 0.024 | 7 |
| 27.60 ± 0.20 | 3.229 ± 0.023 | 25 |
| 28.28 ± 0.20 | 3.153 ± 0.022 | 3 |
| 28.79 ± 0.20 | 3.098 ± 0.021 | 13 |
| 29.09 ± 0.20 | 3.067 ± 0.021 | 8 |
| 29.58 ± 0.20 | 3.017 ± 0.020 | 2 |
| 30.89 ± 0.20 | 2.892 ± 0.018 | 15 |
| 31.16 ± 0.20 | 2.868 ± 0.018 | 2 |
| 31.44 ± 0.20 | 2.843 ± 0.018 | 19 |
| 31.97 ± 0.20 | 2.797 ± 0.017 | 2 |
| 32.76 ± 0.20 | 2.731 ± 0.016 | 4 |
| 32.95 ± 0.20 | 2.716 ± 0.016 | 3 |
| 33.23 ± 0.20 | 2.694 ± 0.016 | 2 |
| 33.76 ± 0.20 | 2.653 ± 0.015 | 9 |
| 34.45 ± 0.20 | 2.601 ± 0.015 | 6 |

TABLE 8

| °2θ | d space (Å) | Intensity (%) |
|---|---|---|
| 9.75 ± 0.20 | 9.064 ± 0.185 | 20 |
| 14.27 ± 0.20 | 6.202 ± 0.086 | 46 |
| 16.90 ± 0.20 | 5.242 ± 0.062 | 68 |
| 19.58 ± 0.20 | 4.530 ± 0.046 | 29 |
| 20.58 ± 0.20 | 4.312 ± 0.041 | 100 |
| 23.08 ± 0.20 | 3.850 ± 0.033 | 64 |
| 23.39 ± 0.20 | 3.800 ± 0.032 | 53 |
| 24.83 ± 0.20 | 3.583 ± 0.028 | 45 |
| 26.79 ± 0.20 | 3.325 ± 0.024 | 20 |
| 27.60 ± 0.20 | 3.229 ± 0.023 | 25 |

TABLE 9

| °2θ | d space (Å) | Intensity (%) |
|---|---|---|
| 9.92 ± 0.20 | 8.909 ± 0.179 | 20 |
| 10.21 ± 0.20 | 8.657 ± 0.169 | 10 |
| 13.96 ± 0.20 | 6.339 ± 0.090 | 51 |
| 14.17 ± 0.20 | 6.245 ± 0.088 | 10 |
| 16.55 ± 0.20 | 5.352 ± 0.064 | 100 |
| 17.06 ± 0.20 | 5.193 ± 0.060 | 15 |
| 17.58 ± 0.20 | 5.041 ± 0.057 | 4 |
| 17.82 ± 0.20 | 4.973 ± 0.055 | 6 |
| 18.25 ± 0.20 | 4.857 ± 0.053 | 6 |
| 19.71 ± 0.20 | 4.501 ± 0.045 | 31 |
| 20.16 ± 0.20 | 4.401 ± 0.043 | 73 |
| 20.35 ± 0.20 | 4.360 ± 0.042 | 9 |
| 20.53 ± 0.20 | 4.323 ± 0.042 | 13 |
| 21.45 ± 0.20 | 4.139 ± 0.038 | 10 |
| 22.07 ± 0.20 | 4.024 ± 0.036 | 51 |
| 22.23 ± 0.20 | 3.996 ± 0.035 | 55 |
| 22.79 ± 0.20 | 3.899 ± 0.034 | 31 |
| 23.04 ± 0.20 | 3.857 ± 0.033 | 10 |
| 23.82 ± 0.20 | 3.733 ± 0.031 | 38 |
| 24.37 ± 0.20 | 3.650 ± 0.029 | 5 |
| 25.06 ± 0.20 | 3.551 ± 0.028 | 27 |
| 26.15 ± 0.20 | 3.405 ± 0.026 | 5 |
| 26.50 ± 0.20 | 3.361 ± 0.025 | 13 |
| 26.66 ± 0.20 | 3.341 ± 0.025 | 15 |
| 26.81 ± 0.20 | 3.323 ± 0.024 | 12 |
| 27.61 ± 0.20 | 3.228 ± 0.023 | 4 |
| 27.73 ± 0.20 | 3.215 ± 0.023 | 4 |
| 28.08 ± 0.20 | 3.175 ± 0.022 | 17 |
| 28.62 ± 0.20 | 3.116 ± 0.021 | 9 |
| 28.94 ± 0.20 | 3.082 ± 0.021 | 3 |
| 29.49 ± 0.20 | 3.026 ± 0.020 | 7 |
| 29.87 ± 0.20 | 2.989 ± 0.020 | 20 |
| 30.11 ± 0.20 | 2.965 ± 0.019 | 4 |
| 30.46 ± 0.20 | 2.932 ± 0.019 | 6 |
| 31.04 ± 0.20 | 2.879 ± 0.018 | 3 |
| 31.47 ± 0.20 | 2.840 ± 0.018 | 4 |
| 31.73 ± 0.20 | 2.818 ± 0.017 | 11 |
| 32.62 ± 0.20 | 2.743 ± 0.016 | 12 |
| 33.51 ± 0.20 | 2.672 ± 0.015 | 4 |
| 33.75 ± 0.20 | 2.654 ± 0.015 | 4 |
| 34.24 ± 0.20 | 2.617 ± 0.015 | 3 |
| 34.44 ± 0.20 | 2.602 ± 0.015 | 4 |
| 34.67 ± 0.20 | 2.585 ± 0.014 | 5 |
| 34.93 ± 0.20 | 2.567 ± 0.014 | 5 |

TABLE 10

| °2θ | d space (Å) | Intensity (%) |
|---|---|---|
| 9.92 ± 0.20 | 8.909 ± 0.179 | 20 |
| 13.96 ± 0.20 | 6.339 ± 0.090 | 51 |
| 16.55 ± 0.20 | 5.352 ± 0.064 | 100 |
| 19.71 ± 0.20 | 4.501 ± 0.045 | 31 |
| 20.16 ± 0.20 | 4.401 ± 0.043 | 73 |
| 22.07 ± 0.20 | 4.024 ± 0.036 | 51 |
| 22.23 ± 0.20 | 3.996 ± 0.035 | 55 |
| 22.79 ± 0.20 | 3.899 ± 0.034 | 31 |
| 23.82 ± 0.20 | 3.733 ± 0.031 | 38 |
| 25.06 ± 0.20 | 3.551 ± 0.028 | 27 |
| 29.87 ± 0.20 | 2.989 ± 0.020 | 20 |

L. DMT Malate Form A

One pattern was analyzed; preferred orientation and particle statistic effects were not assessed. Observed peaks are shown in FIG. 3 and Table 9 below, and prominent peaks are listed in Table 10 below. Note that none of the peaks are known to be representative or characteristic of this material since the state of preferred orientation in this sample is not known. The crystal system is orthorhombic and the space group is P2$_1$2$_1$2$_1$. The cell parameters and calculated volume are: a=8.50595(7) Å, b=10.69563(10) Å, c=16.96938(14) Å, α=90°, β=90°, γ=90°, V=1543.82(2) Å3.

M. DMT Sulfate Form A

One pattern was analyzed; and preferred orientation and particle statistic effects were not assessed. Observed peaks are shown in FIG. 4 and Table 11 below, and prominent peaks are listed in Table 12 below. Note that none of the peaks are known to be representative or characteristic of this material since the state of preferred orientation in this sample is not known. The XRPD pattern of DMT sulfate Form A was successfully indexed by a single unit cell and provides strong evidence that the pattern is representative of a single crystalline phase. The form has a primitive orthorhombic unit cell likely containing four sulfate anions and four DMT cations. Consequently, the estimated formula unit volume of 354 Å 3 calculated from the indexing results would be consistent with an anhydrate.

TABLE 11

| °2θ | d space (Å) | Intensity (%) |
|---|---|---|
| 8.36 ± 0.20 | 10.568 ± 0.252 | 6 |
| 11.05 ± 0.20 | 8.001 ± 0.144 | 100 |
| 12.12 ± 0.20 | 7.297 ± 0.120 | 13 |
| 13.23 ± 0.20 | 6.687 ± 0.101 | 2 |
| 14.14 ± 0.20 | 6.258 ± 0.088 | 15 |
| 15.32 ± 0.20 | 5.779 ± 0.075 | 19 |
| 15.89 ± 0.20 | 5.573 ± 0.070 | 31 |
| 16.24 ± 0.20 | 5.454 ± 0.067 | 40 |
| 16.80 ± 0.20 | 5.273 ± 0.062 | 13 |
| 16.99 ± 0.20 | 5.214 ± 0.061 | 5 |
| 17.48 ± 0.20 | 5.069 ± 0.058 | 4 |
| 19.71 ± 0.20 | 4.501 ± 0.045 | 34 |
| 19.88 ± 0.20 | 4.462 ± 0.044 | 18 |
| 20.34 ± 0.20 | 4.363 ± 0.042 | 13 |
| 20.54 ± 0.20 | 4.321 ± 0.042 | 5 |
| 20.97 ± 0.20 | 4.233 ± 0.040 | 5 |
| 22.22 ± 0.20 | 3.998 ± 0.036 | 35 |
| 22.82 ± 0.20 | 3.894 ± 0.034 | 14 |
| 23.27 ± 0.20 | 3.819 ± 0.032 | 4 |
| 23.54 ± 0.20 | 3.776 ± 0.032 | 19 |
| 23.92 ± 0.20 | 3.717 ± 0.031 | 32 |
| 24.16 ± 0.20 | 3.681 ± 0.030 | 12 |
| 24.40 ± 0.20 | 3.645 ± 0.029 | 20 |
| 25.03 ± 0.20 | 3.555 ± 0.028 | 25 |
| 25.47 ± 0.20 | 3.494 ± 0.027 | 19 |
| 26.14 ± 0.20 | 3.406 ± 0.026 | 16 |
| 26.52 ± 0.20 | 3.358 ± 0.025 | 4 |
| 26.65 ± 0.20 | 3.342 ± 0.025 | 8 |
| 26.77 ± 0.20 | 3.328 ± 0.024 | 8 |
| 27.38 ± 0.20 | 3.255 ± 0.023 | 2 |
| 27.84 ± 0.20 | 3.202 ± 0.023 | 8 |
| 28.18 ± 0.20 | 3.164 ± 0.022 | 7 |
| 28.52 ± 0.20 | 3.127 ± 0.021 | 4 |
| 29.58 ± 0.20 | 3.017 ± 0.020 | 6 |
| 29.72 ± 0.20 | 3.004 ± 0.020 | 5 |
| 30.37 ± 0.20 | 2.941 ± 0.019 | 2 |
| 30.93 ± 0.20 | 2.888 ± 0.018 | 2 |
| 31.31 ± 0.20 | 2.855 ± 0.018 | 6 |
| 31.78 ± 0.20 | 2.814 ± 0.017 | 2 |
| 32.18 ± 0.20 | 2.779 ± 0.017 | 4 |
| 32.83 ± 0.20 | 2.726 ± 0.016 | 2 |
| 32.99 ± 0.20 | 2.713 ± 0.016 | 5 |
| 33.42 ± 0.20 | 2.679 ± 0.016 | 3 |

TABLE 12

| °2θ | d space (Å) | Intensity (%) |
|---|---|---|
| 11.05 ± 0.20 | 8.001 ± 0.144 | 100 |
| 15.32 ± 0.20 | 5.779 ± 0.075 | 19 |
| 15.89 ± 0.20 | 5.573 ± 0.070 | 31 |
| 16.24 ± 0.20 | 5.454 ± 0.067 | 40 |
| 19.71 ± 0.20 | 4.501 ± 0.045 | 34 |
| 19.88 ± 0.20 | 4.462 ± 0.044 | 18 |
| 22.22 ± 0.20 | 3.998 ± 0.036 | 35 |
| 23.54 ± 0.20 | 3.776 ± 0.032 | 19 |
| 23.92 ± 0.20 | 3.717 ± 0.031 | 32 |
| 24.40 ± 0.20 | 3.645 ± 0.029 | 20 |
| 25.03 ± 0.20 | 3.555 ± 0.028 | 25 |
| 25.47 ± 0.20 | 3.494 ± 0.027 | 19 |

N. DMT Oxalate Form A

One pattern was analyzed and preferred orientation and particle statistic effects were assessed through comparison to the calculated XRPD pattern from the single crystal structure. Preferred orientation affects are noted in the experimental XRPD pattern and only the prominent peaks consistent between both patterns are listed as representative. Observed peaks are shown in FIG. 5 and Table 13 below, and representative peaks are listed in Table 14. The crystal system is monoclinic and the space group is P21/c. The cell parameters and calculated volume are: a=15.01660(18) Å, b=8.37069(10) Å, c=11.03060(13) Å, α=90°, β=91.9039 (11)°, γ=90°, V=1385.77(3) Å3.

TABLE 13

| °2θ | d space (Å) | Intensity (%) |
|---|---|---|
| 5.86 ± 0.20 | 15.062 ± 0.513 | 48 |
| 11.77 ± 0.20 | 7.512 ± 0.127 | 7 |
| 14.41 ± 0.20 | 6.141 ± 0.085 | 24 |
| 14.63 ± 0.20 | 6.050 ± 0.082 | 41 |
| 15.85 ± 0.20 | 5.587 ± 0.070 | 4 |
| 16.06 ± 0.20 | 5.515 ± 0.068 | 13 |
| 16.93 ± 0.20 | 5.234 ± 0.061 | 12 |
| 17.29 ± 0.20 | 5.124 ± 0.059 | 14 |
| 17.60 ± 0.20 | 5.035 ± 0.057 | 26 |
| 17.70 ± 0.20 | 5.006 ± 0.056 | 12 |
| 17.95 ± 0.20 | 4.937 ± 0.055 | 11 |
| 18.10 ± 0.20 | 4.898 ± 0.054 | 3 |
| 19.26 ± 0.20 | 4.606 ± 0.047 | 88 |
| 19.65 ± 0.20 | 4.515 ± 0.046 | 9 |
| 20.00 ± 0.20 | 4.436 ± 0.044 | 19 |
| 20.32 ± 0.20 | 4.367 ± 0.043 | 72 |
| 21.21 ± 0.20 | 4.185 ± 0.039 | 38 |
| 22.03 ± 0.20 | 4.032 ± 0.036 | 81 |
| 22.40 ± 0.20 | 3.966 ± 0.035 | 12 |
| 22.71 ± 0.20 | 3.913 ± 0.034 | 35 |
| 22.92 ± 0.20 | 3.877 ± 0.033 | 7 |
| 23.57 ± 0.20 | 3.772 ± 0.032 | 21 |
| 24.34 ± 0.20 | 3.654 ± 0.030 | 17 |
| 25.78 ± 0.20 | 3.453 ± 0.026 | 29 |
| 26.45 ± 0.20 | 3.367 ± 0.025 | 6 |
| 26.65 ± 0.20 | 3.342 ± 0.025 | 9 |
| 26.97 ± 0.20 | 3.303 ± 0.024 | 4 |
| 27.51 ± 0.20 | 3.240 ± 0.023 | 100 |
| 27.77 ± 0.20 | 3.210 ± 0.023 | 13 |
| 28.76 ± 0.20 | 3.102 ± 0.021 | 5 |
| 29.09 ± 0.20 | 3.067 ± 0.021 | 6 |
| 31.12 ± 0.20 | 2.871 ± 0.018 | 3 |
| 31.57 ± 0.20 | 2.832 ± 0.017 | 5 |
| 32.54 ± 0.20 | 2.749 ± 0.016 | 5 |
| 32.81 ± 0.20 | 2.728 ± 0.016 | 12 |
| 33.12 ± 0.20 | 2.703 ± 0.016 | 5 |
| 33.22 ± 0.20 | 2.695 ± 0.016 | 4 |
| 33.67 ± 0.20 | 2.660 ± 0.015 | 18 |
| 34.24 ± 0.20 | 2.617 ± 0.015 | 12 |
| 34.58 ± 0.20 | 2.592 ± 0.015 | 24 |

TABLE 14

| °2θ | d space (Å) | Intensity (%) |
|---|---|---|
| 5.86 ± 0.20 | 15.062 ± 0.513 | 48 |
| 14.63 ± 0.20 | 6.050 ± 0.082 | 41 |
| 17.60 ± 0.20 | 5.035 ± 0.057 | 26 |
| 19.26 ± 0.20 | 4.606 ± 0.047 | 88 |
| 20.32 ± 0.20 | 4.367 ± 0.043 | 72 |
| 22.03 ± 0.20 | 4.032 ± 0.036 | 81 |
| 23.57 ± 0.20 | 3.772 ± 0.032 | 21 |
| 24.34 ± 0.20 | 3.654 ± 0.030 | 17 |
| 25.78 ± 0.20 | 3.453 ± 0.026 | 29 |
| 27.51 ± 0.20 | 3.240 ± 0.023 | 100 |

Thermal analysis of five DMT salt forms have been determined and the results are presented in FIGS. 6-10. Water sorption isotherms of three DMT salt forms have been determined and the results are presented in FIGS. 11-13. The DVS of DMT Oxalate Form A was not acquired because the salt exhibited two endotherms in the DSC indicative of two physical forms. The DVS of the DMT Sulfate Form A was not acquired because the salt deliquesced under 90% RH, RT after 1 day.

Further analysis of DMT succinate Form A, prepared according to the methods described above, were conducted.

Figure 20:
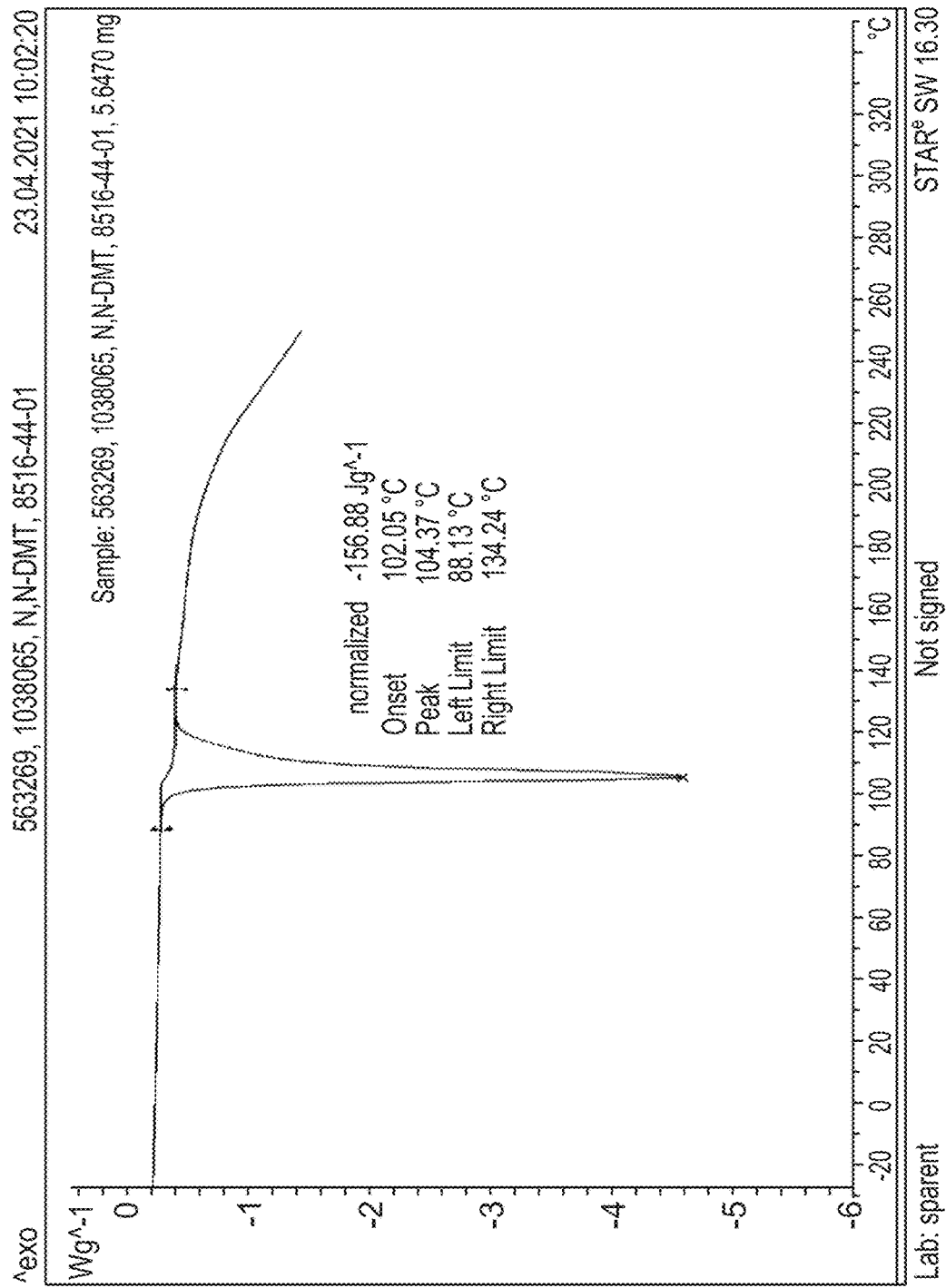
FIG. 20 shows the DSC isotherm for a physical mixture of DMT succinate Form A and succinic acid at an overall composition of 0.34 mole fraction of DMT
Figure 21:
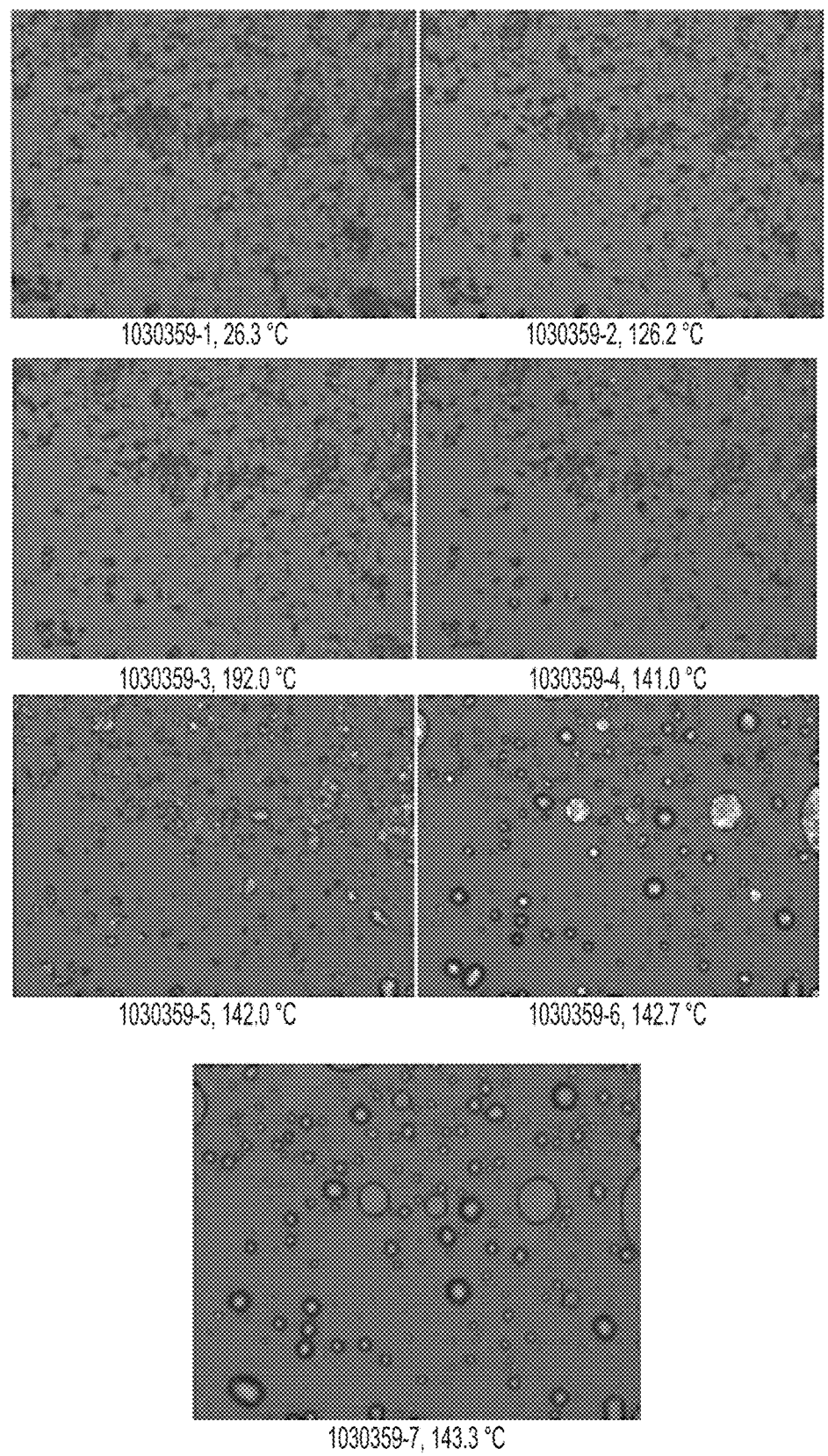
FIG. 21 shows the hot stage micrographs of DMT succinate Form A prepared from acetone (small-scale) confirming melt at 142° C.
Figure 22:
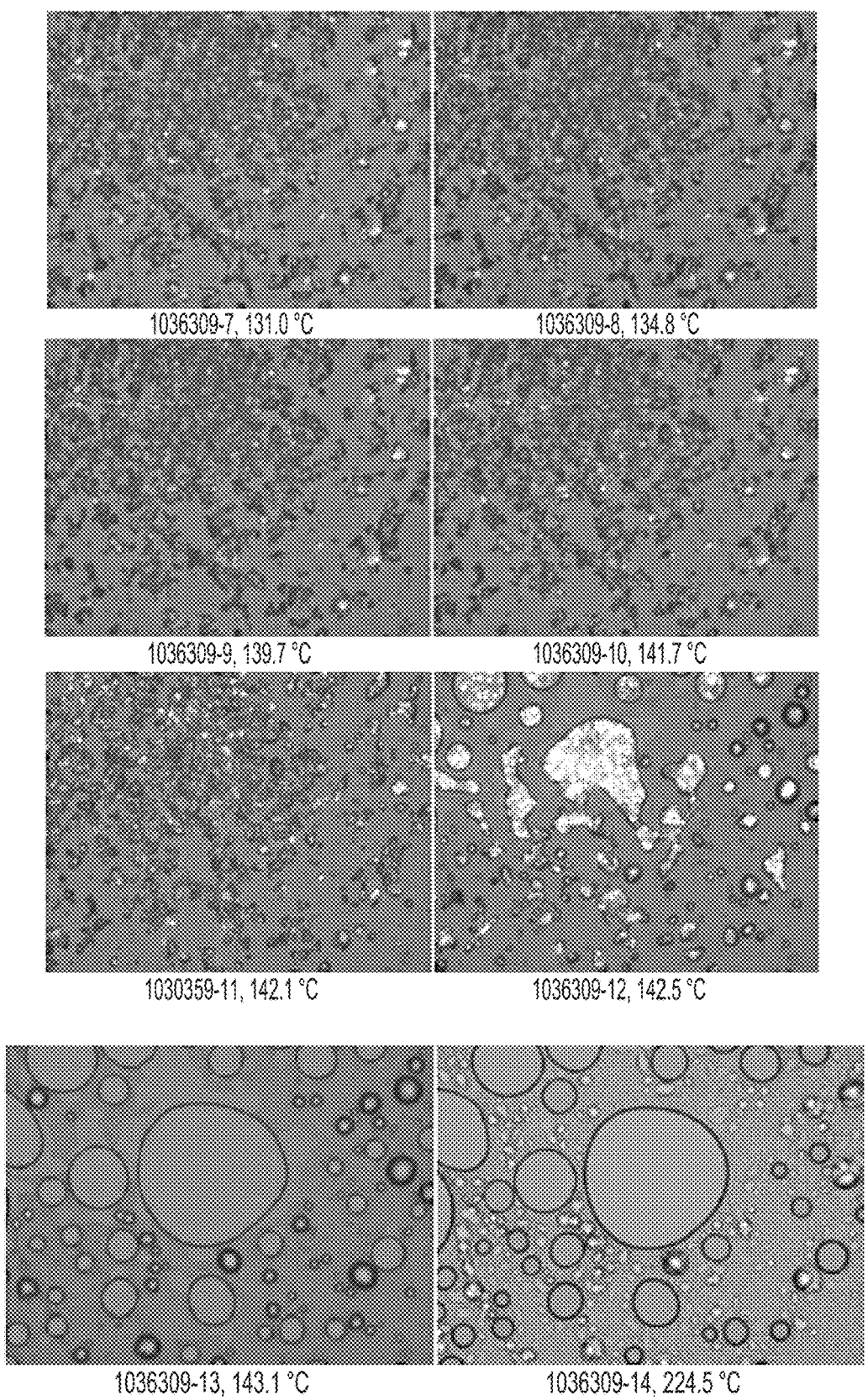
FIG. 22 shows the hot stage micrographs of DMT succinate Form A prepared from ethanol (large-scale)

The results are presented in FIGS. 14-22. Thus, DMT succinate Form A was further analyzed by variable temperature XRPD to see if a form change could be seen. The sample was held at 25° C., 105° C., and 133° C. during heating and X-ray patterns were obtained. The sample was then held at 105° C. during cooling. X-ray patterns were obtained during cooling at 105° C. and 25° C. No form changes were observed at any point during the experiment (FIG. 14). The succinate salt was also prepared on a larger laboratory (gram) scale and characterized further (DVS in FIG. 18, DSC/TGA in FIG. 19). The endotherms with an onset near 142° C. are due to the melt of DMT succinate Form A (FIGS. 21 and 22). The remaining events, such as the minor endotherm near 102° C. and the endothermic shoulder sometimes observed prior to the melt of the salt, are due to the eutectic that is formed with physical mixtures of succinic acid and DMT succinate Form A. The peak onset of the eutectic melt will always be observed at one temperature while the temperatures at which the peak maxima for the broad endotherms are observed are dependent on the overall mixture composition. A physical mixture of succinic acid and DMT succinate Form A at an overall composition of 0.34 mole fraction of DMT was analyzed by DSC to confirm the events observed above (FIG. 20). The composition of 0.34 mole fraction of DMT was arbitrarily selected as the best approximation for the eutectic composition. As expected, the resulting DSC thermogram exhibits a sharp and well-defined endotherm for the eutectic melt with an onset at 102° C. The well-defined shape of the endotherm suggests the overall composition of the mixture is not far from the true eutectic composition. The small endothermic shoulder immediately to the right of eutectic melt represents the completion of the melt of either remaining component at the liquidus boundary.

A representative XRPD pattern for DMT phosphate material, prepared as described above, is presented in FIG. 23.

Figure 23:
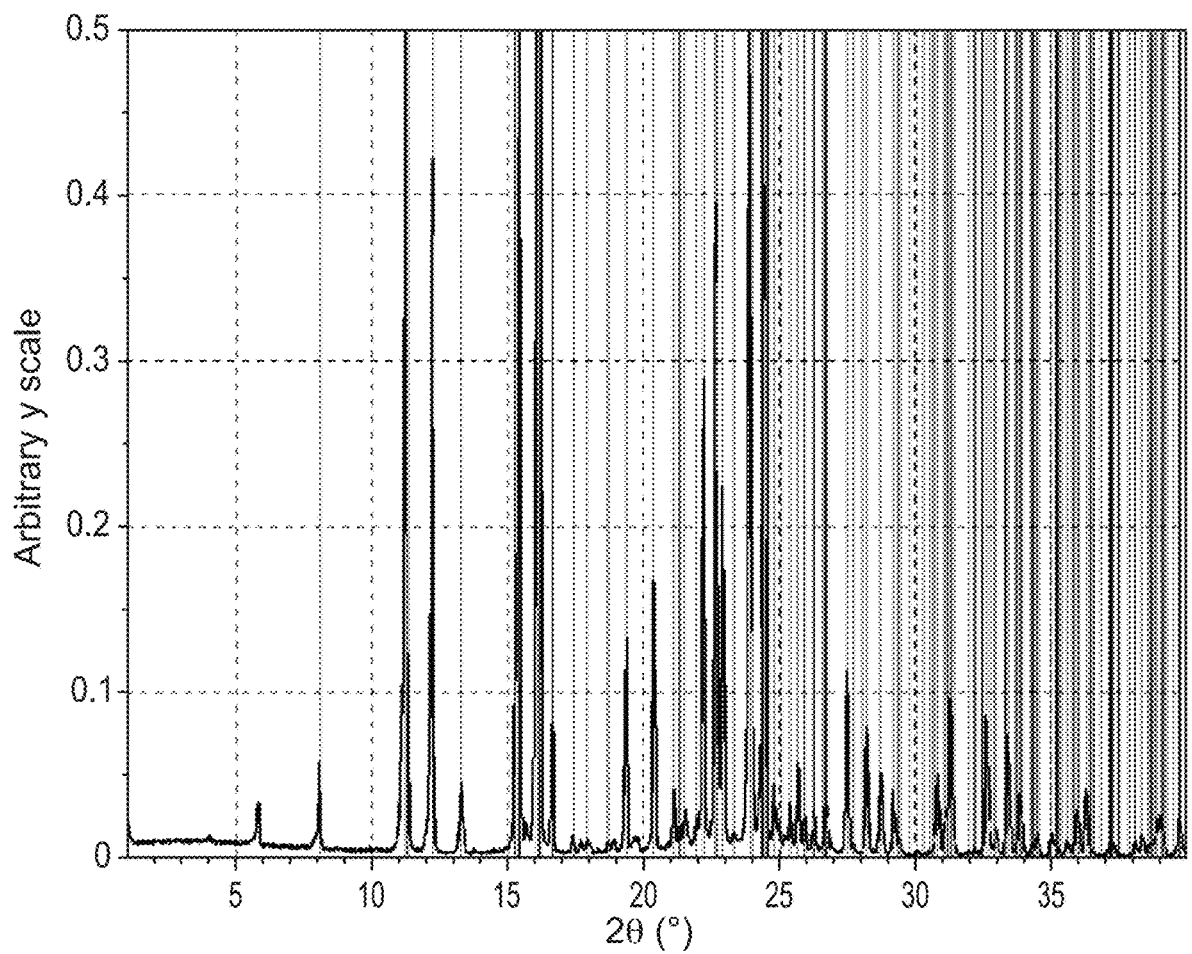
FIG. 23 shows the XRPD for DMT phosphate.
Figure 24:
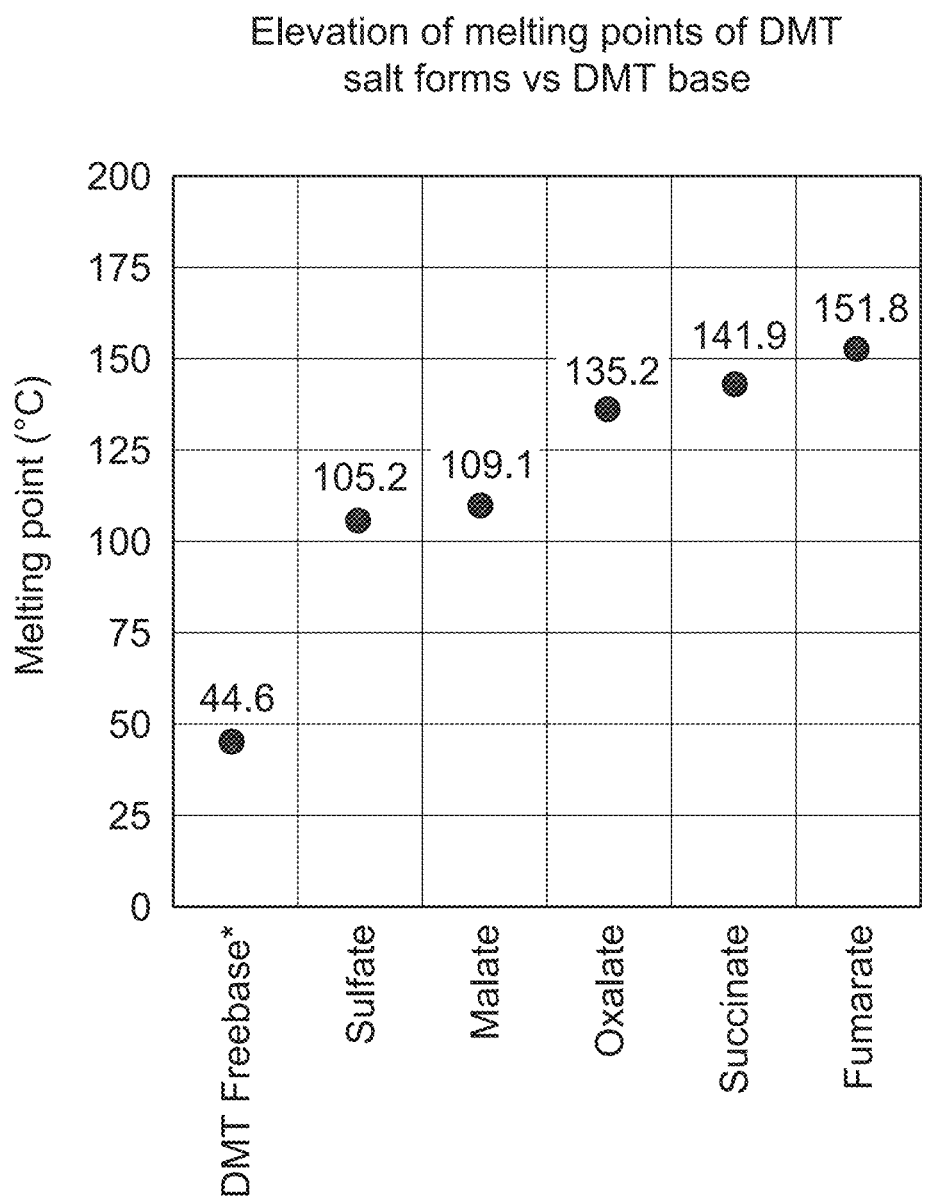
FIG. 24 shows the melting points of five salt forms of DMT compared to DMT free base.

A chart demonstrating the elevated melting points of five DMT salt forms of the present disclosure compared to that of DMT free base is presented in FIG. 23.

The aqueous solubility of DMT fumarate Form A, DMT succinate Form A and DMT malate Form A were determined to be between 20-100 mg/mL. The results are shown in Table 15 below.

TABLE 15

| Initial Form | Aqueous solubility (mg/mL) |
|---|---|
| Fumarate A | 50 |
| Malate A | 93 |
| Succinate A | 46 |

The hygroscopicity of DMT fumarate Form A, DMT succinate Form A and DMT malate Form A was also determined, and the results are shown in Table 16 below.

TABLE 16

| Initial Form | DVS results |
|---|---|
| Fumarate A | Limited hygroscopicity<br>5% to 95%: 0.573% wt. gain (0.1 mol/mol $H_2O$)<br>95% to 5%: 0.679% wt. loss some hysteresis |
| Malate A | Significant hygroscopicity<br>5% to 75%: 1.21% wt. gain (0.4 mol/mol $H_2O$)<br>75% to 95%: 9.75% wt. gain (1.7 mol/mol $H_2O$)<br>95% to 75%: 9.59% wt. loss<br>75% to 5%: 1.37% wt loss |
| Succinate A | Low hygroscopicity<br>5% to 95%: 0.171% wt. gain (0.03 mol/mol $H_2O$)<br>95% to 5%: 0.175% wt. loss some hysteresis |

DMT succinate Form A was found to be least hygroscopic of the three salt forms tested. Other favorable characteristics of DMT succinate Form A are its high melting point, high crystallinity, and preservation of the physical form after water absorption and upon heating and cooling.

The invention claimed is:

1. A N,N-dimethyltryptamine (DMT) succinate crystalline Form A, characterized by an XRPD pattern having peaks at 16.90±0.2, 20.58±0.2, and 23.08±0.2°2θ.

2. The DMT succinate crystalline Form A of claim 1, wherein the crystalline Form A is further characterized by at least one peak selected from 9.75±0.2, 14.27±0.2, 19.58±0.2, 23.39±0.2, 24.83±0.2, 26.79±0.2, and 27.6±0.2°2θ.

3. The DMT succinate crystalline Form A of claim 1, wherein the crystalline Form A is further characterized by at least one peak selected from 9.75±0.2, 11.61±0.2, 13.28±0.2, 14.27±0.2, 14.72±0.2, 16.55±0.2, 17.36±0.2, 17.71±0.2, 18.82±0.2, 19.58±0.2, 20.30±0.2, 20.90±0.2, 21.51±0.2, 22.23±0.2, 22.50±0.2, 22.86±0.2, 23.39±0.2, 24.83±0.2, 25.17±0.2, 26.19±0.2, 26.79±0.2, 27.27±0.2, 27.60±0.2, 28.28±0.2, 28.79±0.2, 29.09±0.2, 29.58±0.2, 30.89±0.2, 31.16±0.2, 31.44±0.2, 31.97±0.2, 32.76±0.2, 32.95±0.2, 33.23±0.2, 33.76±0.2, and 34.45±0.2°2θ.

4. The DMT succinate crystalline Form A of claim 1, wherein the crystalline Form A provides an XRPD pattern substantially in accordance with FIG. 2.

5. The DMT succinate crystalline Form A of claim 1, wherein the crystalline Form A exhibits a TGA thermograph substantially in accordance with FIG. 10.

6. The DMT succinate crystalline Form A of claim 1, wherein the crystalline Form A exhibits a DSC thermograph substantially in accordance with FIG. 10.

7. The DMT succinate crystalline Form A of claim 1, wherein the crystalline Form A exhibits a DVS isotherm substantially in accordance with FIG. 13.

8. The DMT succinate crystalline Form A of claim 1, wherein the crystalline Form A provides a variable temperature XRPD pattern substantially in accordance with FIG. 14.

9. The DMT succinate crystalline Form A of claim 1, wherein the crystalline Form A exhibits a DSC isotherm substantially in accordance with FIG. 15.

10. The DMT succinate crystalline Form A of claim 1, wherein the crystalline Form A provides an XRPD pattern substantially in accordance with FIG. 16.

11. The DMT succinate crystalline Form A of claim 1, wherein the crystalline Form A provides an XRPD pattern substantially in accordance with FIG. 17.

12. The DMT succinate crystalline Form A of claim 1, wherein the crystalline Form A provides a single crystal X-ray diffraction (SCXRD) pattern substantially in accordance with FIG. 17.

13. The DMT succinate crystalline Form A of claim 1, wherein the crystalline Form A exhibits a DVS isotherm substantially in accordance with FIG. 18.

14. The DMT succinate crystalline Form A of claim 1, wherein the crystalline Form A exhibits a TGA thermograph substantially in accordance with FIG. 19.

15. The DMT succinate crystalline Form A of claim 1, wherein the crystalline Form A exhibits a DSC thermograph substantially in accordance with FIG. 19.

16. The DMT succinate crystalline Form A of claim 1, wherein the crystalline Form A has a melting point of about 141.9° C. when measured under ambient conditions.

\* \* \* \* \*